(12) United States Patent
Bryan et al.

(10) Patent No.: US 8,109,901 B2
(45) Date of Patent: Feb. 7, 2012

(54) BREAST PUMP

(75) Inventors: Raymond G. Bryan, Reno, NV (US); Patricia S. Ruby, Truckee, CA (US); Megan E. Oehlert, Reno, NV (US); Jimi Francis, Sparks, NV (US)

(73) Assignee: Simplisse, Inc., St. Louis, MO (US)

( * ) Notice: Subject to any disclaimer, the term of this patent is extended or adjusted under 35 U.S.C. 154(b) by 75 days.

(21) Appl. No.: 12/613,955

(22) Filed: Nov. 6, 2009

(65) Prior Publication Data

US 2010/0121265 A1    May 13, 2010

Related U.S. Application Data

(60) Provisional application No. 61/112,444, filed on Nov. 7, 2008.

(51) Int. Cl.
*A61M 1/06* (2006.01)

(52) U.S. Cl. .......................... 604/74; 604/313

(58) Field of Classification Search .................... 604/74, 604/75, 313–316

See application file for complete search history.

(56) References Cited

U.S. PATENT DOCUMENTS

| | | |
|---|---|---|
| 2,542,505 A | 2/1951 | Gascoigne |
| 4,190,021 A | 2/1980 | Reisgies |
| 4,391,221 A | 7/1983 | Hoefelmayr et al. |
| 4,583,970 A | 4/1986 | Kirchner |
| 4,584,992 A | 4/1986 | Liu |
| 4,607,596 A | 8/1986 | Whittlestone et al. |
| D288,004 S | 1/1987 | Blachly |
| 4,680,028 A | 7/1987 | Stuart |
| 4,740,196 A | 4/1988 | Powell |
| 4,772,262 A | 9/1988 | Grant et al. |
| 4,886,494 A | 12/1989 | Morifuji |
| 5,007,899 A | 4/1991 | Larsson |
| 5,049,126 A | 9/1991 | Larsson |
| 5,141,403 A | 8/1992 | Guo et al. |
| 5,218,924 A | 6/1993 | Thompson et al. |
| 5,284,180 A | 2/1994 | Guo et al. |
| 5,419,768 A * | 5/1995 | Kayser .......................... 604/119 |
| 5,520,613 A | 5/1996 | Copelan |
| D372,975 S | 8/1996 | Meyers et al. |
| 5,542,921 A | 8/1996 | Meyers et al. |

(Continued)

FOREIGN PATENT DOCUMENTS

AU          200149040 B2     7/2001

(Continued)

OTHER PUBLICATIONS

Zoppou et al., "Comparing Breastfeeding and Breast Pumps Using a Computer Model", J Hum Lact, 13(3), pp. 195-202, 1997.

(Continued)

*Primary Examiner* — Jackie Ho
*Assistant Examiner* — Gerald Landry, II
(74) *Attorney, Agent, or Firm* — Armstrong Teasdale LLP

(57) ABSTRACT

A breast pump has at least one collection assembly for engaging at least a portion of a breast surrounding a nipple and a vacuum pump for applying a vacuum to the collection assembly and thereby to at least the nipple of the breast. A controller is operable to cyclically operate the vacuum pump between a maximum vacuum pressure in the range of about 70 mm Hg to about 150 mm Hg and a latching pressure of about 30 mm Hg.

26 Claims, 60 Drawing Sheets

U.S. PATENT DOCUMENTS

| | | | |
|---|---|---|---|
| D375,357 S | 11/1996 | Silver | |
| 5,571,084 A * | 11/1996 | Palmer | 604/74 |
| 5,601,531 A | 2/1997 | Silver | |
| D383,536 S | 9/1997 | Bachman et al. | |
| 5,749,850 A | 5/1998 | Williams et al. | |
| 5,776,098 A | 7/1998 | Silver et al. | |
| 5,797,875 A | 8/1998 | Silver | |
| 5,810,772 A | 9/1998 | Niederberger | |
| 5,843,029 A | 12/1998 | Bachman et al. | |
| 5,885,246 A | 3/1999 | Ford | |
| 5,902,267 A | 5/1999 | Medo | |
| 5,954,690 A | 9/1999 | Larsson | |
| 6,045,529 A | 4/2000 | Nuesch | |
| 6,090,065 A | 7/2000 | Giles | |
| 6,139,521 A | 10/2000 | Larsson | |
| 6,152,896 A | 11/2000 | Bachman et al. | |
| D446,852 S | 8/2001 | Johansen et al. | |
| D446,853 S | 8/2001 | Johansen et al. | |
| 6,273,868 B1 | 8/2001 | Nordvik | |
| 6,379,327 B2 | 4/2002 | Lundy | |
| 6,383,163 B1 | 5/2002 | Kelly et al. | |
| 6,383,164 B1 | 5/2002 | Johansen et al. | |
| 6,497,677 B2 | 12/2002 | Silver | |
| 6,547,756 B1 | 4/2003 | Greter et al. | |
| 6,663,587 B2 | 12/2003 | Silver et al. | |
| 6,673,036 B1 | 1/2004 | Britto | |
| 6,673,037 B1 | 1/2004 | Silver | |
| 6,676,631 B1 | 1/2004 | Greter | |
| 6,699,213 B1 | 3/2004 | Annis et al. | |
| 6,706,012 B2 | 3/2004 | McKendry et al. | |
| 6,712,785 B2 | 3/2004 | Morton et al. | |
| 6,723,066 B2 | 4/2004 | Larsson et al. | |
| D496,097 S | 9/2004 | Rosnak et al. | |
| 6,808,517 B2 | 10/2004 | Greter et al. | |
| D500,551 S | 1/2005 | Lantz et al. | |
| 6,840,918 B1 * | 1/2005 | Britto et al. | 604/74 |
| 6,899,696 B2 | 5/2005 | Morton et al. | |
| 6,921,379 B2 | 7/2005 | Greter et al. | |
| 6,932,790 B2 | 8/2005 | McKendry et al. | |
| 6,964,651 B1 | 11/2005 | McKendry | |
| 6,974,439 B1 | 12/2005 | McKendry | |
| 7,029,454 B2 | 4/2006 | Watanabe | |
| 7,101,350 B2 | 9/2006 | Ytteborg | |
| 7,128,877 B2 | 10/2006 | Quay et al. | |
| 7,166,087 B2 | 1/2007 | Silver et al. | |
| 7,201,735 B2 | 4/2007 | Atkin et al. | |
| 7,223,255 B2 | 5/2007 | Myers et al. | |
| D564,656 S | 3/2008 | Matsutori et al. | |
| 7,354,418 B2 | 4/2008 | Lee et al. | |
| 7,381,197 B2 | 6/2008 | Kelly et al. | |
| 7,396,339 B2 | 7/2008 | Britto et al. | |
| 2001/0044593 A1 * | 11/2001 | Lundy | 604/74 |
| 2002/0032404 A1 | 3/2002 | Silver | |
| 2002/0072702 A1 | 6/2002 | Quay | |
| 2002/0193731 A1 | 12/2002 | Myers et al. | |
| 2003/0004459 A1 | 1/2003 | McKendry et al. | |
| 2003/0069536 A1 | 4/2003 | Greter et al. | |
| 2003/0139702 A1 | 7/2003 | Renz et al. | |
| 2003/0149398 A1 | 8/2003 | Renz et al. | |
| 2003/0153869 A1 | 8/2003 | Ytteborg | |
| 2003/0236491 A1 * | 12/2003 | McKendry et al. | 604/74 |
| 2004/0024351 A1 | 2/2004 | Greter et al. | |
| 2004/0024352 A1 | 2/2004 | Renz et al. | |
| 2004/0039330 A1 | 2/2004 | Silver | |
| 2004/0127845 A1 | 7/2004 | Renz et al. | |
| 2004/0158199 A1 | 8/2004 | McKendry et al. | |
| 2004/0215138 A1 | 10/2004 | Greter et al. | |
| 2005/0020971 A1 | 1/2005 | McKendry et al. | |
| 2005/0043677 A1 * | 2/2005 | Kelly et al. | 604/74 |
| 2005/0085768 A1 | 4/2005 | Greter et al. | |
| 2005/0101908 A1 * | 5/2005 | Atkin et al. | 604/74 |
| 2005/0154349 A1 | 7/2005 | Renz et al. | |
| 2005/0165350 A1 | 7/2005 | Greter et al. | |
| 2005/0222536 A1 | 10/2005 | Silver | |
| 2005/0245860 A1 | 11/2005 | Britto et al. | |
| 2005/0251089 A1 | 11/2005 | Lee et al. | |
| 2005/0256449 A1 | 11/2005 | Tashiro | |
| 2006/0111664 A1 | 5/2006 | Samson et al. | |
| 2006/0111665 A1 | 5/2006 | Gillan | |
| 2006/0157065 A1 | 7/2006 | Rohrig | |
| 2007/0088250 A1 | 4/2007 | Silver et al. | |
| 2007/0219486 A1 | 9/2007 | Myers et al. | |
| 2008/0009815 A1 | 1/2008 | Grabenkort et al. | |
| 2008/0033352 A1 | 2/2008 | Annis et al. | |
| 2008/0045887 A1 | 2/2008 | Larsson et al. | |
| 2008/0077082 A1 | 3/2008 | Geddes | |
| 2008/0097290 A1 | 4/2008 | Geddes | |
| 2008/0177224 A1 | 7/2008 | Kelly et al. | |
| 2008/0243059 A1 | 10/2008 | Yamashita et al. | |
| 2008/0255503 A1 | 10/2008 | Quackenbush et al. | |
| 2008/0262420 A1 | 10/2008 | Dao et al. | |
| 2010/0130921 A1 * | 5/2010 | Kobayashi et al. | 604/74 |

FOREIGN PATENT DOCUMENTS

| | | |
|---|---|---|
| AU | 2005201595 A1 | 5/2005 |
| CA | 2115824 A1 | 8/1994 |
| CA | 2594129 A1 | 7/2001 |
| CA | 2480672 A1 | 10/2003 |
| CA | 2495380 A1 | 3/2004 |
| CA | 2451171 C | 6/2008 |
| DE | 540934 C | 12/1931 |
| DE | 2451953 A1 | 5/1976 |
| DE | 2807646 A1 | 8/1978 |
| DE | 3328725 A1 | 2/1984 |
| DE | 00993020 T1 | 8/2005 |
| EP | 0123269 A2 | 10/1984 |
| EP | 0466462 A1 | 1/1992 |
| EP | 0733376 A2 | 9/1996 |
| EP | 0611578 B1 | 1/1998 |
| EP | 0604070 B1 | 7/1998 |
| EP | 1034807 A1 | 9/2000 |
| EP | 1468705 A2 | 10/2004 |
| EP | 0631468 B2 | 12/2006 |
| FR | 599054 A | 1/1926 |
| GB | 168234 A | 9/1921 |
| GB | 271857 A | 10/1927 |
| GB | 762701 A | 12/1956 |
| GB | 2082920 A | 3/1982 |
| GB | 2127293 A | 4/1984 |
| MX | PA04009579 A | 5/2005 |
| MX | PA05002063 A | 6/2005 |
| SE | 158976 C | 5/1954 |
| WO | 9207593 A1 | 5/1992 |
| WO | 9951882 A1 | 10/1999 |
| WO | 0041744 A1 | 7/2000 |
| WO | 0041745 A1 | 7/2000 |
| WO | 0057934 A1 | 10/2000 |
| WO | 0147577 A3 | 12/2001 |
| WO | 03082378 A1 | 10/2003 |
| WO | 2004018018 A2 | 3/2004 |
| WO | 2005084729 A1 | 9/2005 |
| WO | 2008034193 A1 | 3/2008 |
| WO | 2008127991 A1 | 10/2008 |

OTHER PUBLICATIONS

Zoppou et al., "Dynamics of Human Milk Extraction: A Comparative Study of Breast Feeding and Breast Pumping", Bulletin of Mathematical Biology, vol. 59, No. 5, pp. 953-973, Sep. 19, 1997.

"Breast Pumps", http://www.mybirthcare.com/expresserstudy.asp, 3 pages.

Philips, Avent, "Twin Electronic Breast Pump User Manual", pp. 1-65.

Tommee Tippee, "Electric Breast Pump User Manual", 21 pages.

Hygeia, "EnDeare Electric Breastpump User Manual", 22 pages.

"Stimulating the Milk—Ejection Reflex", Breastfeeding and Human Lactation, pp. 324-328, 2005.

Carmen Acosta Johnson, Ph.D., "An Evaluation of Breast Pumps Currently Available on the American Market", Clinical Pediatrics, vol. 22, No. 1, pp. 40-45, 1983.

Newton et al., "Relation of the Let-Down Reflex to the Ability to Breast Feed," Pediatrics, Abstract, vol. 5, No. 4, pp. 726-733, Apr. 1950.

Michael W. Woolridge, "The 'Anatomy' of Infant Sucking," Midwifery, 2(4), pp. 164-171, Dec. 1986.

MC Neville et al, Studies in human lactation: milk volumes in lactating women during the onset of lactation and full lactation, American Journal of Clinical Nutrition, Abstract, vol. 48, pp. 1375-1386, 1988.

Kelly et al., "Measuring Breathing and Swallowing Coordination in Human Infants Using the Kay Elemetrics Swallowing Workstation," pp. 1-9.

Mitoulas et al., "Efficacy of Breast Milk Expression Using an Electric Breast Pump," Journal of Human Lactation, Abstract, vol. 18, No. 4, 344-352, 2002.

Kent et al., "Response of Breasts to Different Stimulation Patterns of an Electric Breast Pump," Journal of Human Lactation, vol. 19, No. 2, 179-186, 2003.

Mitoulas et al., "Effect of Vacuum Profile on Breast Milk Expression Using an Electric Breast Pump," Journal of Human Lactation, Abstract, vol. 18, No. 4, 353-360, 2002.

Zinaman et al., "Acute Prolactin and Oxytocin Responses and Milk Yield to Infant Suckling and Artificial Methods of Expression in Lactating Women," Pediatrics, vol. 89, pp. 437-440, 1992.

Qureshi et al., "Changes in rhythmic suckle feeding patterns in term infants in the first month of life," Developmental Medicine & Child Neutology, vol. 44, pp. 34-39, 2002.

Mizuno et al., "Effects of Different Fluids on the Relationship between Swallowing and breathing during Nutritive Suckling in Neonates," Biology of the Neonate, 81, pp. 45-50, 2002.

Wolff et al., "Nonnutritive Sucking and Response Thresholds in Young Infants," Child Development, 38(3), pp. 631-638, Sep. 1967.

Levin et al., "Nonnutritive Suckling by Human Neonates," Child Develpment, 35, pp. 749-758, 1964.

Lappi et al., "Effects of nutritive and non-nutritive sucking on infant heart rate variability during the first 6 months of life," Infant Behavior and Development, vol. 30, Issue 4, 17 pages, 2007.

Boiron et al., "Effects of oral stimulation and oral support on non-nutritive sucking and feeding performance in preterm infants," Developmental Medicine & Child Neurology, 49, pp. 439-444, 2007.

Nyqvist et al., "Early oral behaviour in preterm infants during breastfeeding: an electromyographic study," Acta Paediatrica, vol. 90, Issue 6, pp. 658-663, 2001.

Lau et al., "Coordination of suck-swallow and swallow respiration in preterm infants," Acta Paediatrica, vol. 92 Issue 6, pp. 721-727, 2003.

Mary-Scovill Elder, "The Effects of Temperature and Position on the Sucking Pressure of Newborn Infants," Child Dev., 41(1), pp. 95-102, Mar. 1970.

Vice et al., "Respiratory patterns and strategies during feeding in preterm infants," Developmental Medicine & Child Neurology, 50, pp. 467-472, 2008.

Ruth A. Lawrence, "Breast-Feeding," Pediatrics in Review, 11, pp. 163-171, Dec. 1989.

Ramsey et al., "Ultrasound Imaging of Milk Ejection in the Breast of Lactating Women," Pediatrics, vol. 113, No. 2, pp. 361-367, Feb. 2004.

Ramsey et al., "The Use of Ultrasound to Characterize Milk Ejection in Women Using an Electric Breast Pump," Journal of Human Lactation, 21(4), pp. 421-428, 2005.

International Search Report and Written Opinion regarding PCT/US2009/063521, dated Feb. 26, 2010, 15 pages.

* cited by examiner

BREAST PUMP

CROSS-REFERENCE TO RELATED APPLICATION

This application claims the benefit of U.S. Provisional Application No. 61/112,444, filed Nov. 7, 2008, which is incorporated herein by reference in its entirety.

BACKGROUND

The field of this disclosure relates generally to breast pumps and more particularly to a breast pump that mimics the suckling of a nursing infant thereby providing an efficient and comfortable pump for nursing mothers.

Breast pumps, whether electric or manually operated, typically include at least one breast cup configured for sealing placement over a nursing mother's breast. A vacuum pump is operatively connected to the breast cup for applying a vacuum to the mother's breast within the cup. More specifically, commonly configured breast cups have a central passage for receiving at least the mother's nipple and more typically some adjacent portion of the mother's breast, allowing vacuum pressure to be applied to the mother's nipple for extracting milk. During use, the vacuum pressure is often applied in pulses, with the central passage being sometimes vented between pulses. A bottle or other suitable receptacle is usually in fluid connection with the breast cup to collect the extracted milk.

When a baby is placed at the breast to be fed, a cascade of events occurs. The baby places their mouth and tongue (latches) with a negative pressure of approximately 30 mm Hg to the nipple/areola and stimulates milk ejection through a series of quick, shallow sucks referred to as non-nutritive suckling. Non-nutritive suckling consists of stable lengths of sucking bursts and duration of pauses. The average pressure of non-nutritive suckling is approximately 70 to 90 mm Hg. As the baby non-nutritive suckles, the mother's brain recognizes the stimulation at the breast and a reflex arc occurs. This reflex arc causes an oxytocin release from the posterior pituitary, which ultimately leads to milk ejection. Oxytocin is a hormone that acts on the myoepithelial cells eliciting a contraction of the smooth muscle cells around the alveolus in the breast. The contraction of these cells actively pushes the milk into the ducts toward the nipple, where the milk is ejected. The baby acts as a milk collector by means of nutritive suckling with strong, even draws. During nutritive suckling the movement of the tongue, jaw, and swallowing facilitates milk flow. The average pressure for nutritive suckling is approximately 75-100 mm Hg.

Vacuum pressure needed to extract milk using a conventional breast pump is substantially higher than that of a suckling infant. For example, the vacuum pressure applied to the mother's breast by conventional breasts pump is often 200 mm Hg (millimeters of mercury) and greater. Over the full transfer period, such high vacuum pressure can often be painful to the mother and in some cases can irritate or damage the mother's breast tissue. Moreover, applying pulses of vacuum pressure to the mother's breast does not adequately simulate the peristaltic movements of an infant's mouth and tongue during breastfeeding to apply oral pressure to the mother's breast.

There is a need, therefore, for a breast pump that is more comfortable to a nursing mother and more effectively simulates the oral pressure and movement of an infant during feeding.

SUMMARY

In one aspect, a breast pump generally comprises at least one collection assembly for engaging at least a portion of a breast surrounding a nipple and a vacuum pump for applying a vacuum to the collection assembly and thereby to at least the nipple of the breast. A controller is operable to cyclically operate the vacuum pump between a maximum vacuum pressure in the range of about 70 mm Hg to about 150 mm Hg and a latching pressure of about 30 mm Hg.

In another aspect, a breast pump further comprises at least one collection assembly including a cup assembly, a container for receiving milk expressed from a nipple of a breast, and a coupler for fluidly connecting the breast cup to the container. The cup assembly has a support member and a liner mounted on the support member. The liner comprises an outer flange portion and a longitudinal portion extending outward from the flange portion. The outer flange portion of the liner is generally planar and adapted to engage the portion of the breast surrounding the nipple during use of the breast cup. The longitudinal portion of the liner is generally tubular and adapted to receive the nipple of the breast therein. A vacuum pump is able to apply a vacuum to the longitudinal portion of the liner and thereby to the nipple. A positive pressure pump is able for pressurize the outer flange portion of the liner to thereby apply a force against the breast at a location spaced from the nipple.

DETAILED DESCRIPTION OF THE DRAWINGS

Figure 1:
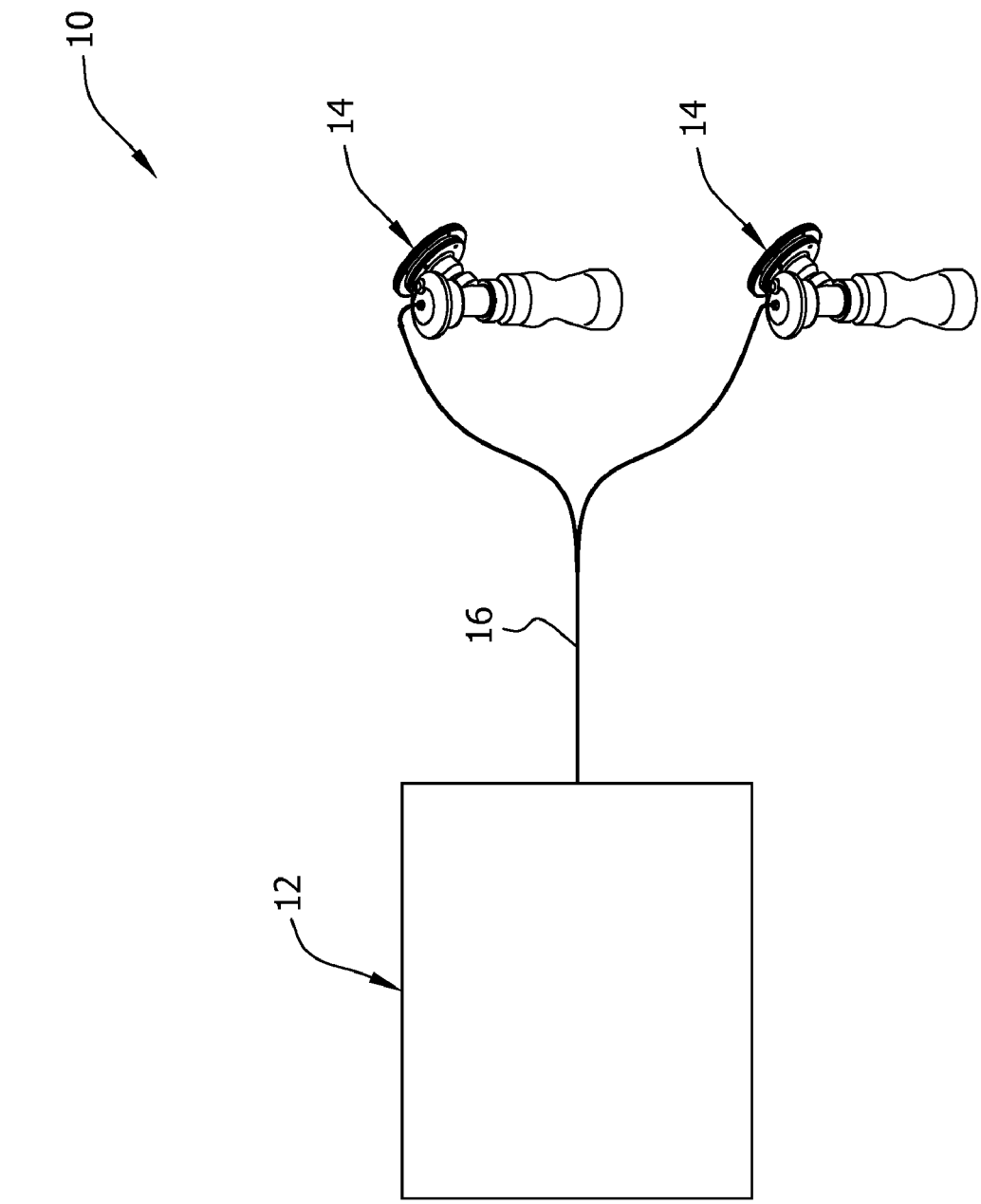
FIG. 1 is a schematic of one embodiment of an electric breast pump.

With reference now to the accompanying drawings, and specifically to FIG. 1, an electric breast pump according to one embodiment is schematically illustrated and is indicated generally at 10. The breast pump 10 includes a suitable housing, indicated generally at 12, for housing various working components such as pumps, a controller, and other components as will be described later herein. The breast pump 10 also comprises a pair of collection assemblies, indicated generally at 14, and flexible tubing or conduits 16 pneumatically connecting the collection assemblies to the housing. The housing 12 can be any suitable housing sized and configured for containing various components of the breast pump as described in more detail below. The illustrated breast pump 10 includes a pair of collection assemblies 14 for expressing milk from each of a nursing mother's breast, either simultaneously or independent of each other. It is contemplated that the collection assemblies 14 can be sufficiently independently operable so that a nursing mother can use only one of the two collection assemblies to express milk from a single breast. It is also contemplated that the breast pump 10 can be provided with a single collection assembly 14 for expressing milk from each of the nursing mother's breasts separately.

Figure 2:
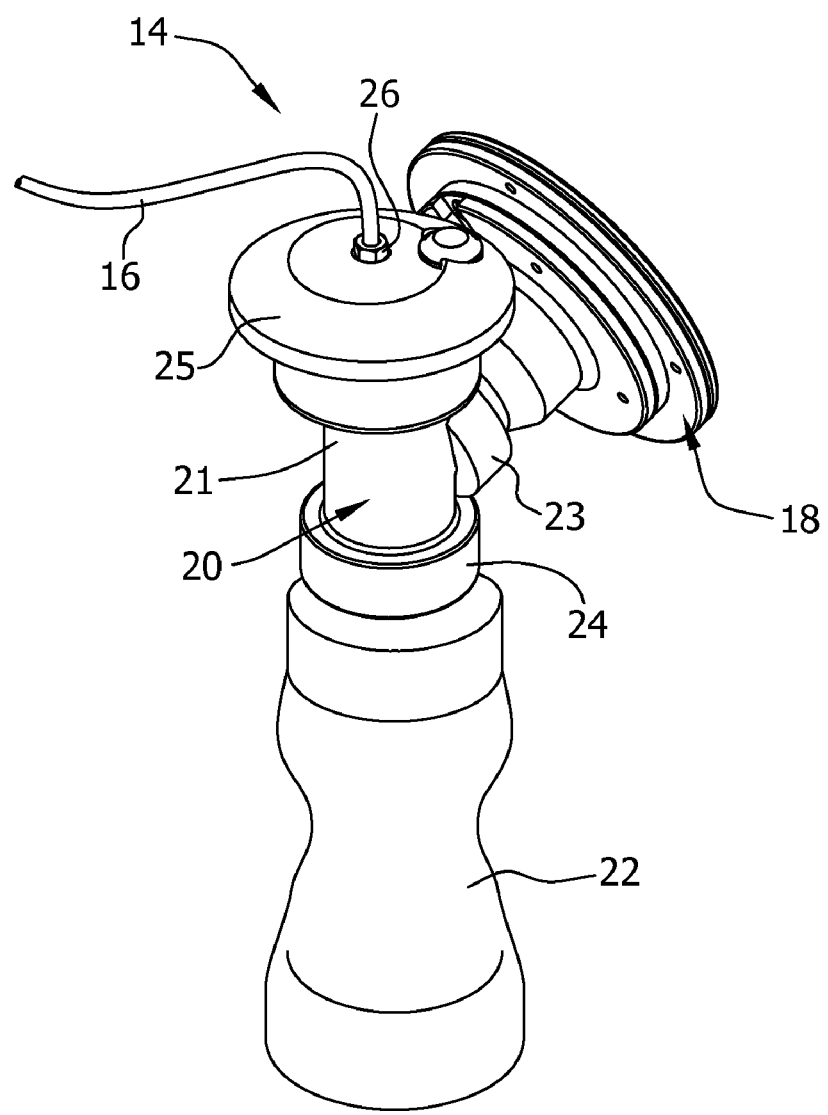
FIG. 2 is an enlarged perspective of one collection assembly of the breast pump of FIG. 1.
Figure 3:
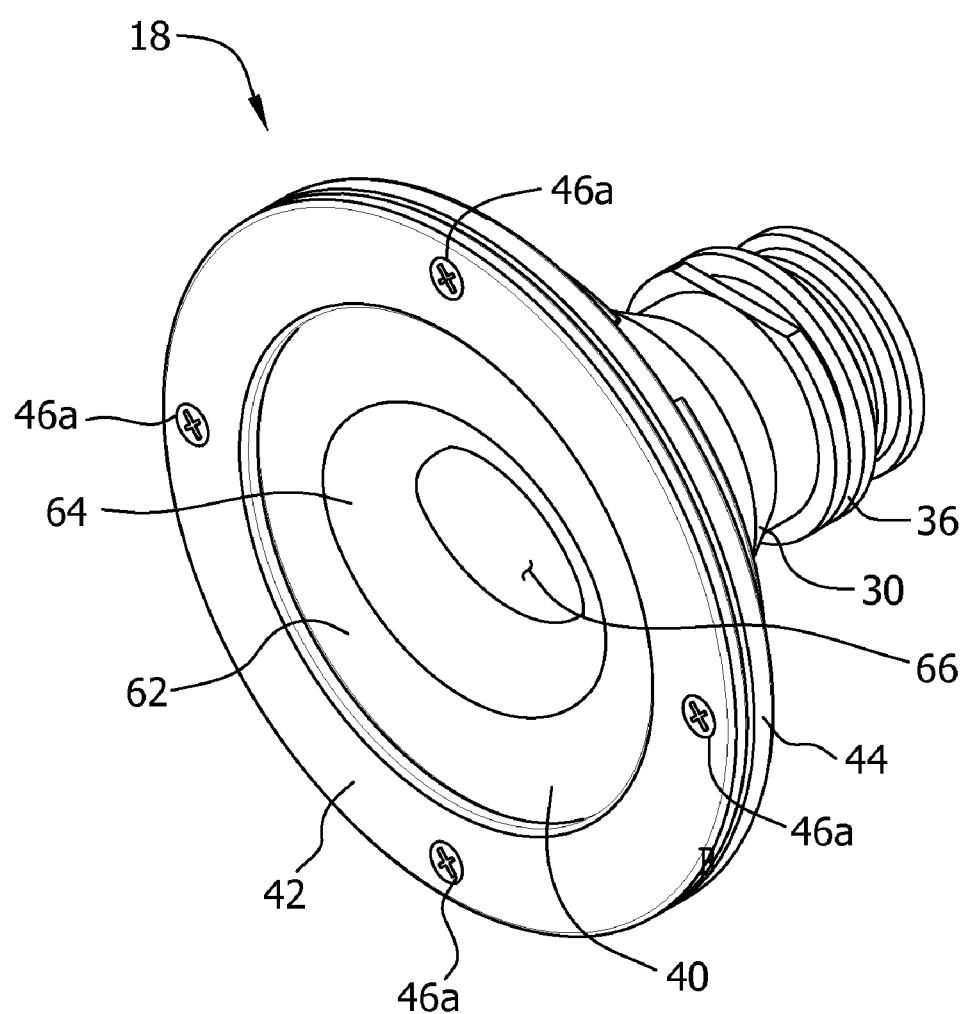
FIG. 3 is a perspective of a cup assembly of the collection assembly of FIG. 2.
Figure 4:
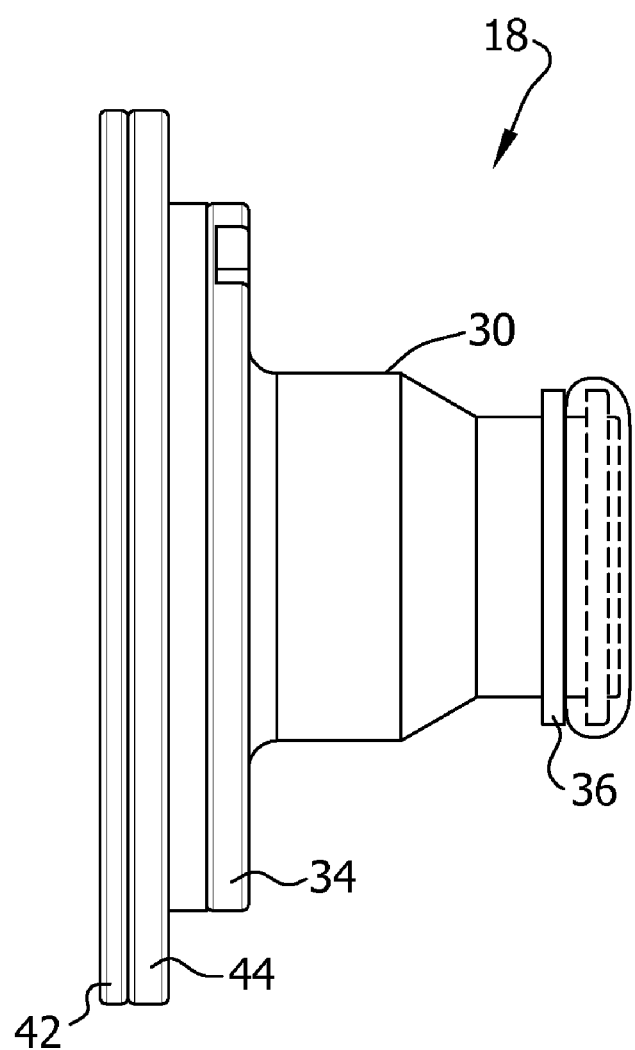
FIG. 4 is a side elevation of the cup assembly.

As illustrated in FIG. 2, each of the collection assemblies 14 comprises a cup assembly, indicated generally at 18, a coupler 20 (broadly defining a manifold), and a container 22 for receiving milk expressed from the nursing mother's breast. In the illustrated embodiment, the container 22 is a conventional nursing bottle. It is understood, however, that other types of bottles and containers can be used to collect the expressed breast milk. For example, the container 22 can be a dedicated storage bottle.

The illustrated coupler 20 is configured to have a primary tubular segment 21 defining a primary channel (not shown) oriented vertically in the drawings (e.g., to simulate the general orientation of the collection assembly in use), and a secondary tubular segment 23 extending outward from the primary segment at an angle relative thereto and defining a secondary channel (not shown) within the coupler. The coupler 20 includes a threaded lower socket 24, e.g., at the lower end of the primary segment 21, for threaded connection with the container 22 to couple the container to the coupler. A lid or cap 25 is mounted (e.g., by suitable threading, by snap fit, or other suitable mounting arrangement) on the coupler 20 at the top of the primary segment 21 to sealingly close the upper end of the primary channel. A port 26 in the cap 25 receives the conduit 16 to pneumatically connect the collection assembly 14 and more particularly the coupler 20 to the housing 12 (i.e., to a vacuum pump therein). The cup assembly 18 is mounted on the coupler 20 at the distal end of the secondary segment 23 to provide pneumatic communication between the cup assembly and the housing, and fluid communication between the cup assembly and the container via the coupler. It is understood that couplers having other shapes and configurations can be used without departing from the scope of this invention. It is also understood that the coupler 20 may connect to the conduit 16, the cup assembly 18, and/or container 22 in any suitable manner, such as, threads, and snap-fits, or other connection.

With reference to FIGS. 3-8, each cup assembly 18 is sized and shaped for receiving and forming a seal with the nursing mother's breast, particularly at the mother's nipple. Specifically, each cup assembly 18 comprises a generally tubular, and more particularly funnel-shaped, support member 30 having an interior or central passage 32 extending longitudinally therethrough. The support member 30 may be constructed of any suitable material but in a particularly suitable embodiment is sufficiently resistant to deformation in response to positive or negative pressure applied thereto at the operating pressures of the breast pump. For example, the support member 30 may be suitably constructed of a generally rigid plastic. The support member 30 has a flanged longitudinally outer end 34 and a pair of external, annular shoulders 36 for snap-fit connection with the coupler 20 to releasably connect the cup assembly to the coupler.

The cup assembly 18 further comprises a pair of expandable liners, referred to herein as inner liner 38 and outer liner 40. A pair of annular mounting collars or rings (e.g., an outer ring 42 and an inner ring 44 each of which is shaped generally in the form of a large washer) sealingly mount the inner and outer liners 38, 40 on the support member 30 of the cup assembly. Suitable fasteners 46a, 46b (e.g., bolts, screws, rivets) are used to secure the mounting rings 42, 44 to the flanged outer end 34 of the support member 30. It is understood, however, that the inner and outer liners 38, 40 may be mounted on the support member 30 of the cup assembly 18 in another suitable manner without departing from the scope of this invention.

Each of the liners 38, 40 is suitably constructed of an elastic material to allow the liners to expand or stretch upon the application of pressure thereto, and then return to a less expanded or undeformed condition upon the removal of such pressure. For example, one suitable material from which the liners 38, 40 can be constructed is silicone. It is understood that the liners 38, 40 can be constructed of different materials and remain with the scope of this invention.

Figure 6:
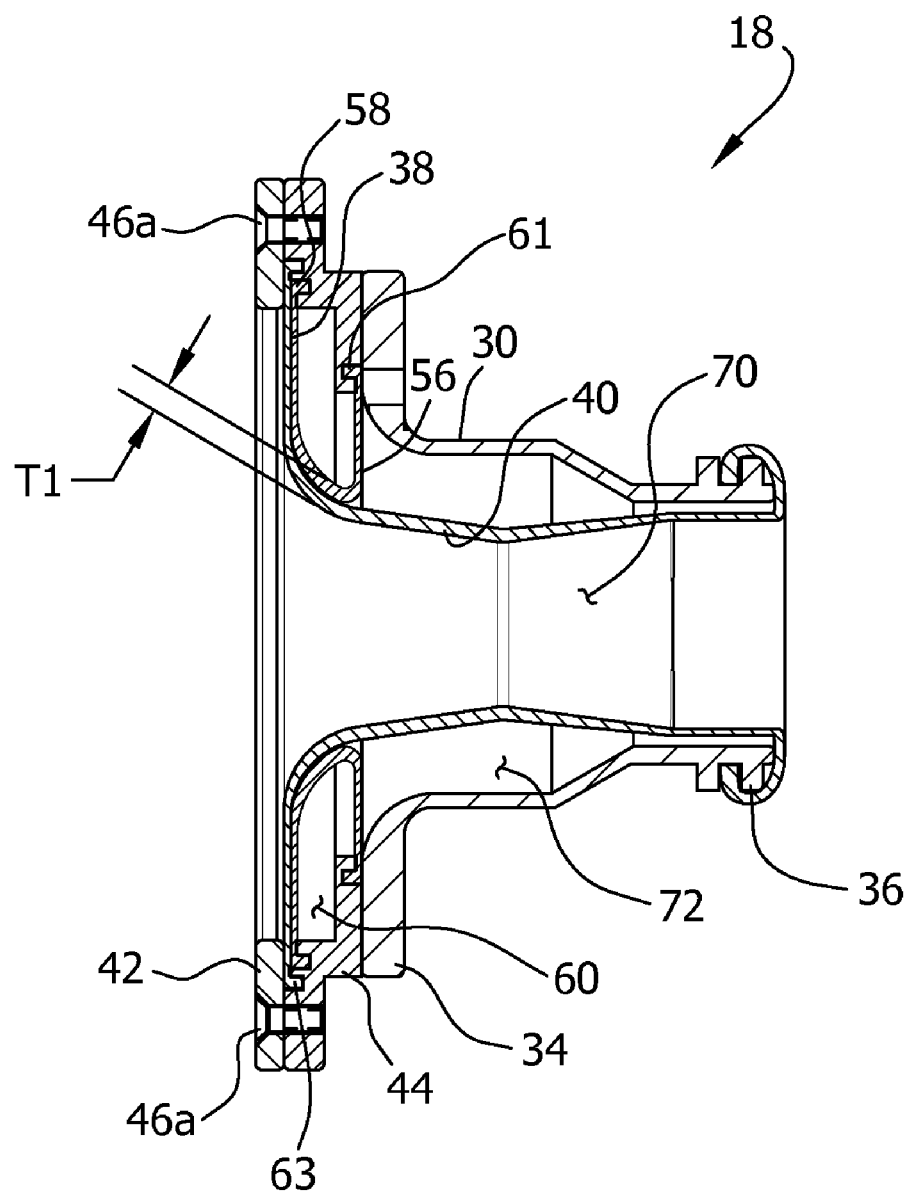
FIG. 6 is a cross-section taken along line 6-6 of FIG. 5A.
Figure 7:
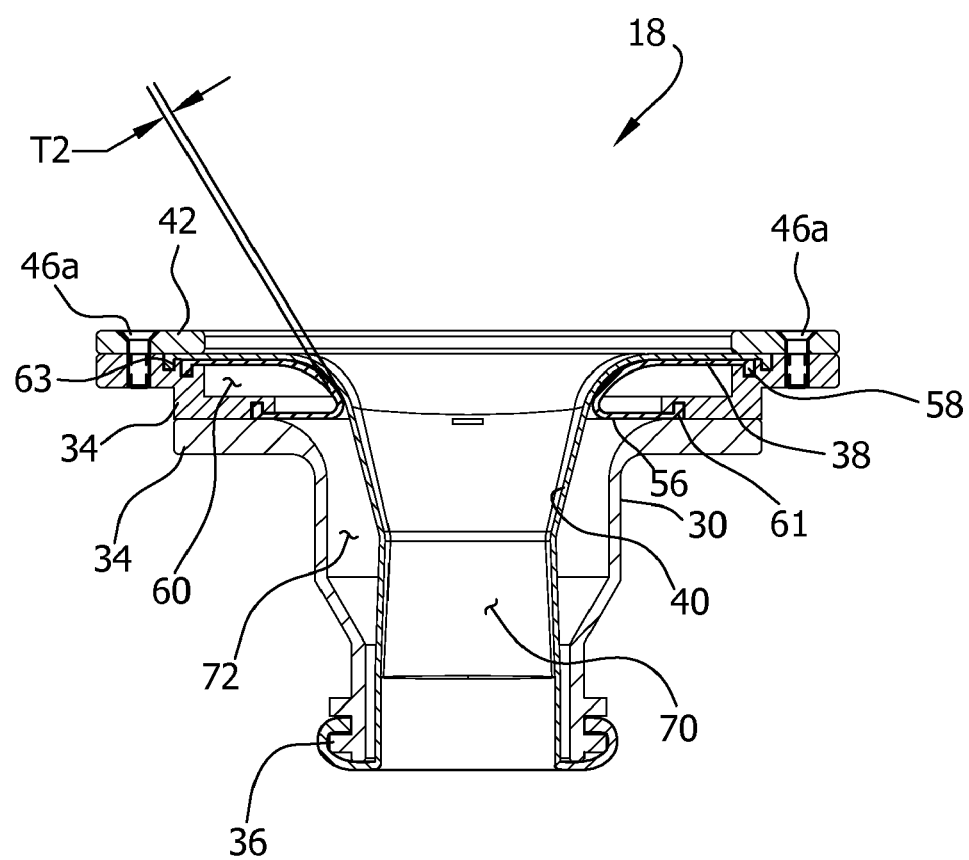
FIG. 7 is a cross-section taken along line 7-7 of FIG. 5A.
Figure 8:
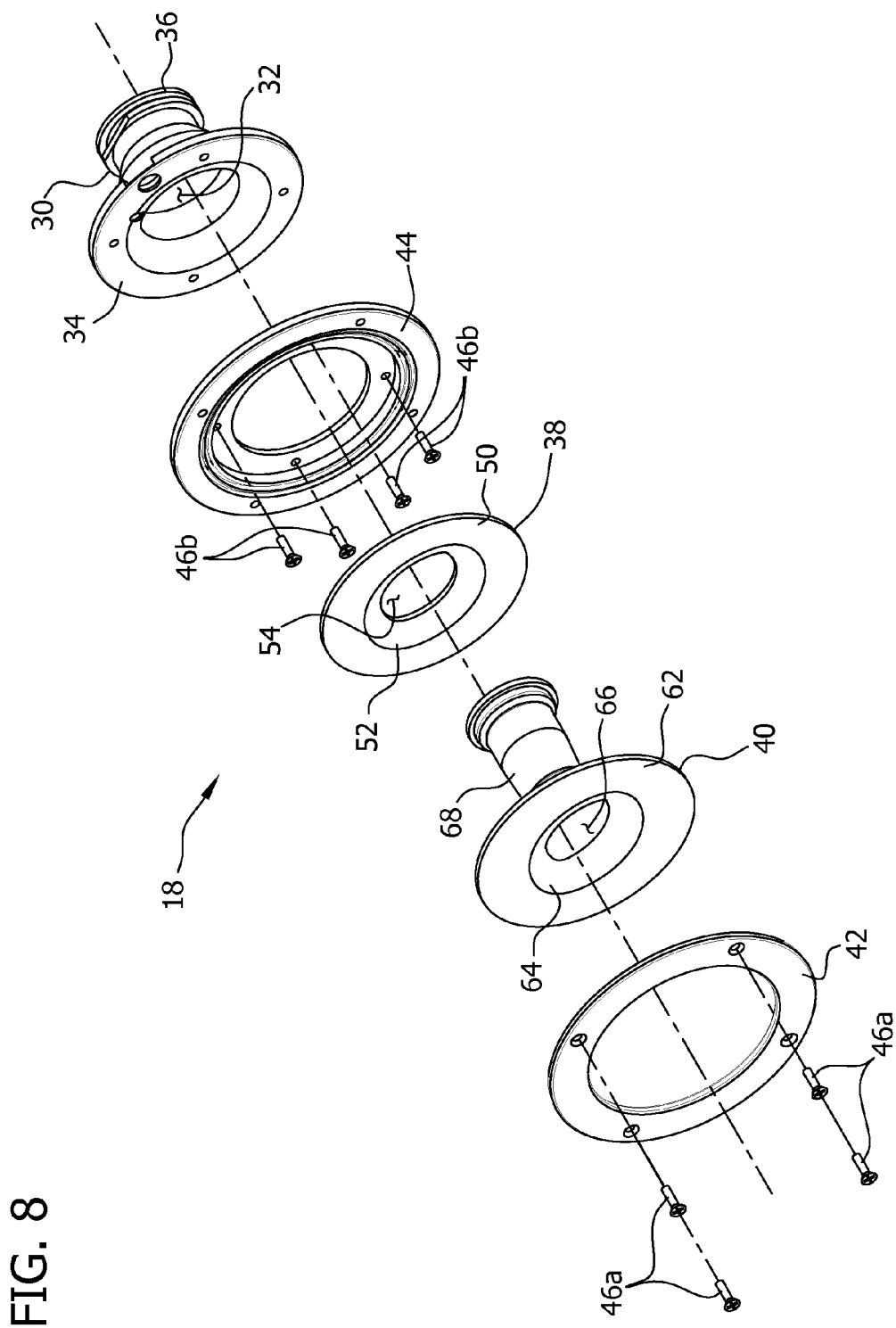
FIG. 8 is an exploded perspective of the cup assembly.

With reference to FIGS. 6-8, the inner liner 38 is generally disc-shaped or annular having a generally U-shaped cross-section defining a first or outer flange portion 50, a second or inner flange portion 56 generally opposed to and spaced from the outer flange portion, and a tapered web portion 52 extending inward from and interconnecting the inner and outer flange portions. The inner liner 38 further defines a generally elliptical central opening 54, e.g., as defined by the tapered web portion 52 of the inner liner 38. As illustrated in FIGS. 6 and 7, the outer flange portion 50 of the inner liner 38 has an annular rib 58 depending therefrom for being received in a corresponding annular locating groove in the outer surface of the inner mounting ring 44. The inner flange portion 56 has an annular rib 61 upstanding therefrom for being received in a corresponding annular locating groove in the inner surface of the inner mounting ring 44. In this manner, the inner liner 38 and the inner mounting ring 44 cooperatively define a first pressure chamber 60 of the cup assembly 18. At least one port (not shown) is formed in the inner mounting ring 44 for providing pneumatic communication between the first pressure chamber 60 and one or more pressure pumps within the housing 16.

With reference again to FIG. 8, the outer liner 40 is generally tubular and more suitably funnel shaped to define an outer flange portion 62, a tapered central portion 64 extending from the outer flange portion, and longitudinal portion 68 extending longitudinally within the support member 30 from the tapered central portion of the outer liner to a terminal inner end of the outer liner adjacent the inner end of the support member 30. The outer liner 40 has a generally elliptical entry opening 66 defined by the outer flange portion 62 and tapered central portion 64, and a longitudinal channel 70 defined by the longitudinal portion and thus defining a vacuum channel of the cup assembly 18 in pneumatic communication with the secondary channel of the coupler 20.

As illustrated in FIGS. 6 and 7, the outer flange portion 62 includes an annular rib 63 depending therefrom for being received in an annular locating groove in the inner mounting ring 44. The outer mounting ring secures to the inner mounting ring in opposed relationship to sealingly clamp the outer flange portion 50 of the inner liner 38 and the outer flange portion 62 of the outer liner 40 between the mounting rings. In this manner, the outer liner 40 and the support member 30 together define a second pressure chamber 72. In the illustrated embodiment, the outer liner 40 overlays the inner liner 38 so that the inner liner is generally enclosed between the support member 30 and the outer liner. It is understood, however, that the inner liner 38 may be disposed exterior of the outer liner without departing from the scope of this invention. It is also contemplated that the first and second pressure chambers 60, 72 may instead be formed from a single liner that is configured and/or secured to the support member so as to define two separate pressure chambers.

With reference to FIGS. 5-8, the elliptical openings 54, 66 in the inner and outer liners 38, 40 are aligned coaxially with each other. The elliptical opening 66 in the outer liner 40 defines the entry opening into which the mother's breast is inserted into the cup assembly and has a major axis MAJ and minor axis MIN. In one particularly suitable embodiment, the thickness of at least one of and more suitably each of the inner and outer liners 38, 40 is reduced at the ends of the major axis MAJ of the elliptical openings 54, 66. For example, the inner and outer liners 38, 40 may have a first combined thickness T1 when viewed in cross-section along a line that includes the minor axes MIN of the openings 54, 66 (FIG. 6), and a second combined thickness T2 when viewed in cross-section along a line that includes the major axes MAJ of the openings (FIG. 7). The first combined thickness T1 is greater than the second combined thickness T2. As one example, the thickness of the outer liner 40 generally at the ends of the major axis MAJ of the opening 66 is approximately 0.030 inches while the thickness of the outer liner about the remainder of the opening is approximately 0.075. For the inner liner 38, the thickness generally at the ends of the major axis of the opening 54 is approximately 0.030 while the thickness of the inner liner about the remainder of the opening is approximately 0.075.

Figure 5A:
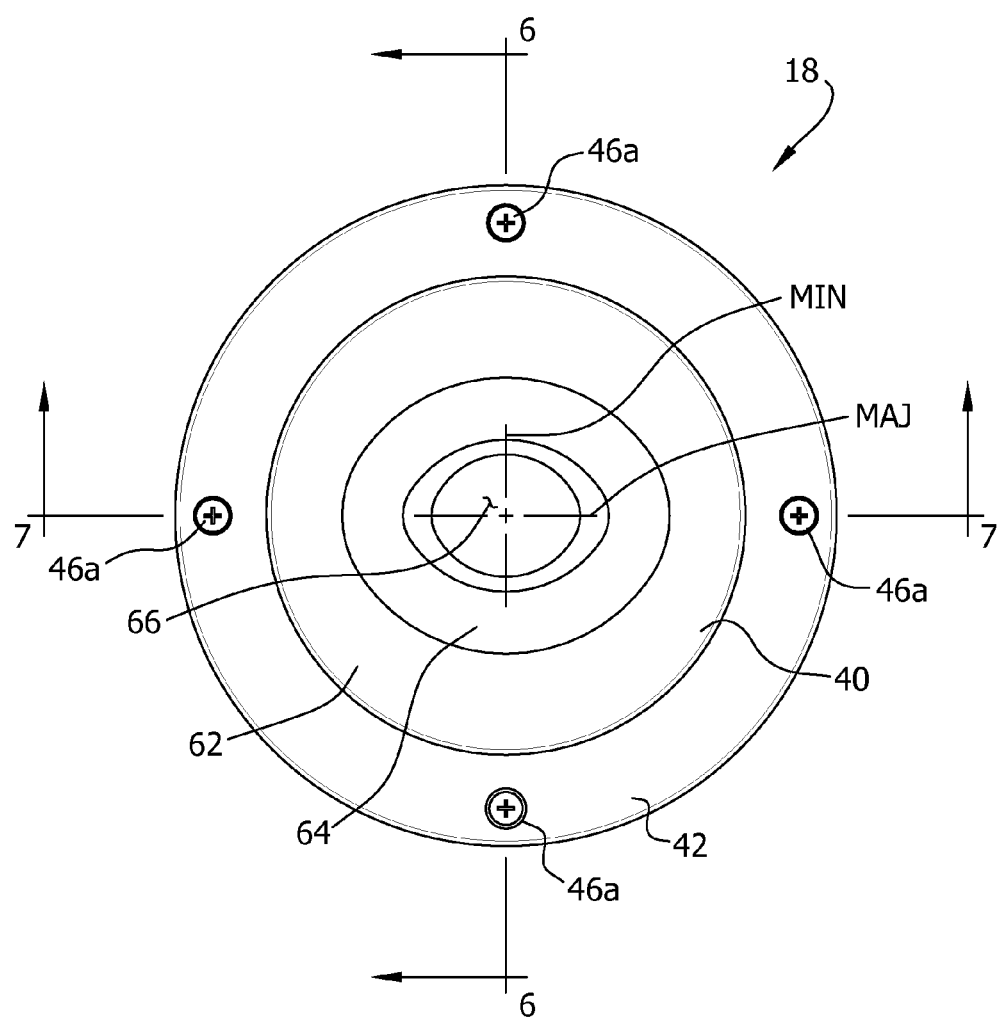
FIG. 5A is a plan view of the cup assembly with inner and outer liners of the cup assembly in an initial, or undeformed configuration.
Figure 5B:
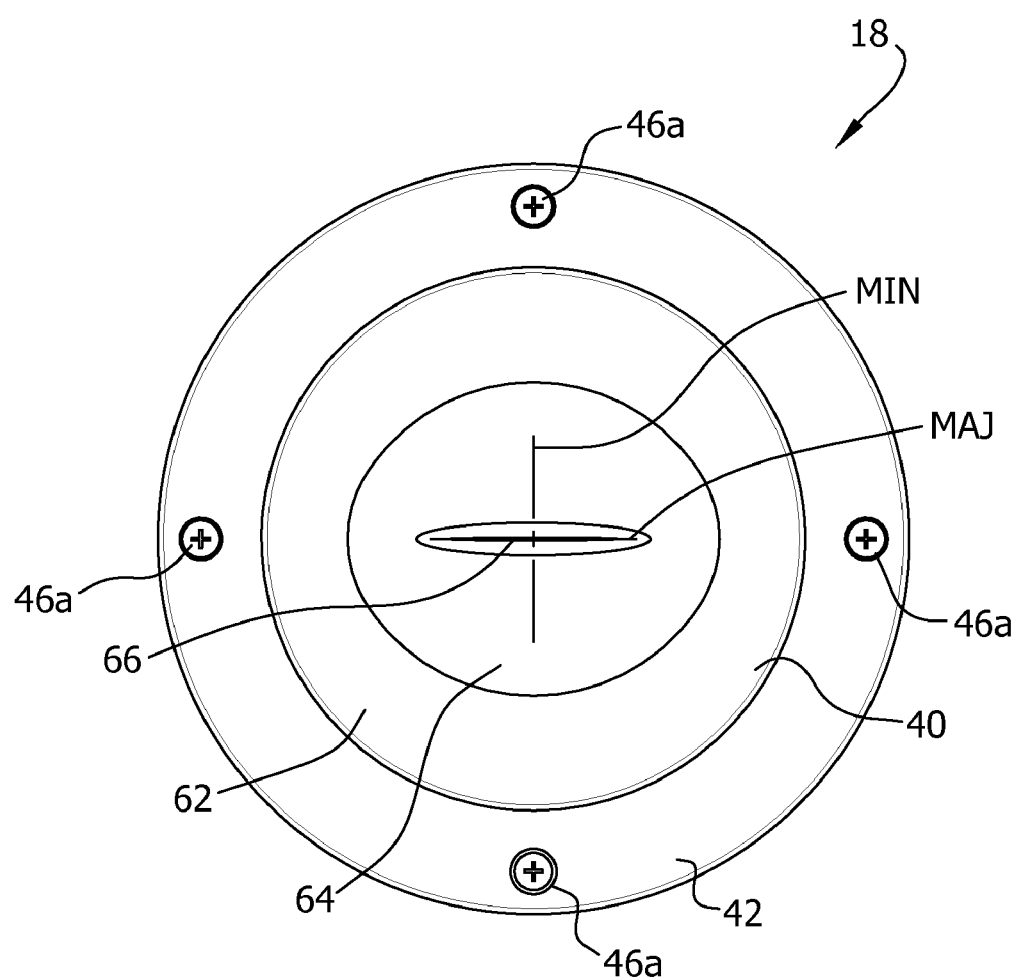
FIG. 5B is plan similar to FIG. 5A with the inner and outer liners of the cup assembly hingedly moved to a generally collapsed configuration.

This thickness differential (i.e., thinning of the inner and/or outer liners 38, 40 generally at the ends of the major axes MAJ of openings 54, 66) creates a living hinge to facilitate a hinged movement of the liners generally about the major axis MAJ of the opening 66 between the fully opened configuration illustrated in FIG. 5A and a collapsed configuration (illustrated in FIG. 5B without a mother's breast therein) in response to pressure applied to the liners (e.g., vacuum pressure in the central passage of the outer liner and/or positive pressure applied to the first and second pressure chambers). This hinged movement more accurately simulates the oral movements applied by a suckling infant to the mother's breast. It is understood that the hinged movement of the inner and outer liners 38, 40 may be created or facilitated in a manner other than by or in addition to varying the thickness of the liners.

Figure 9:
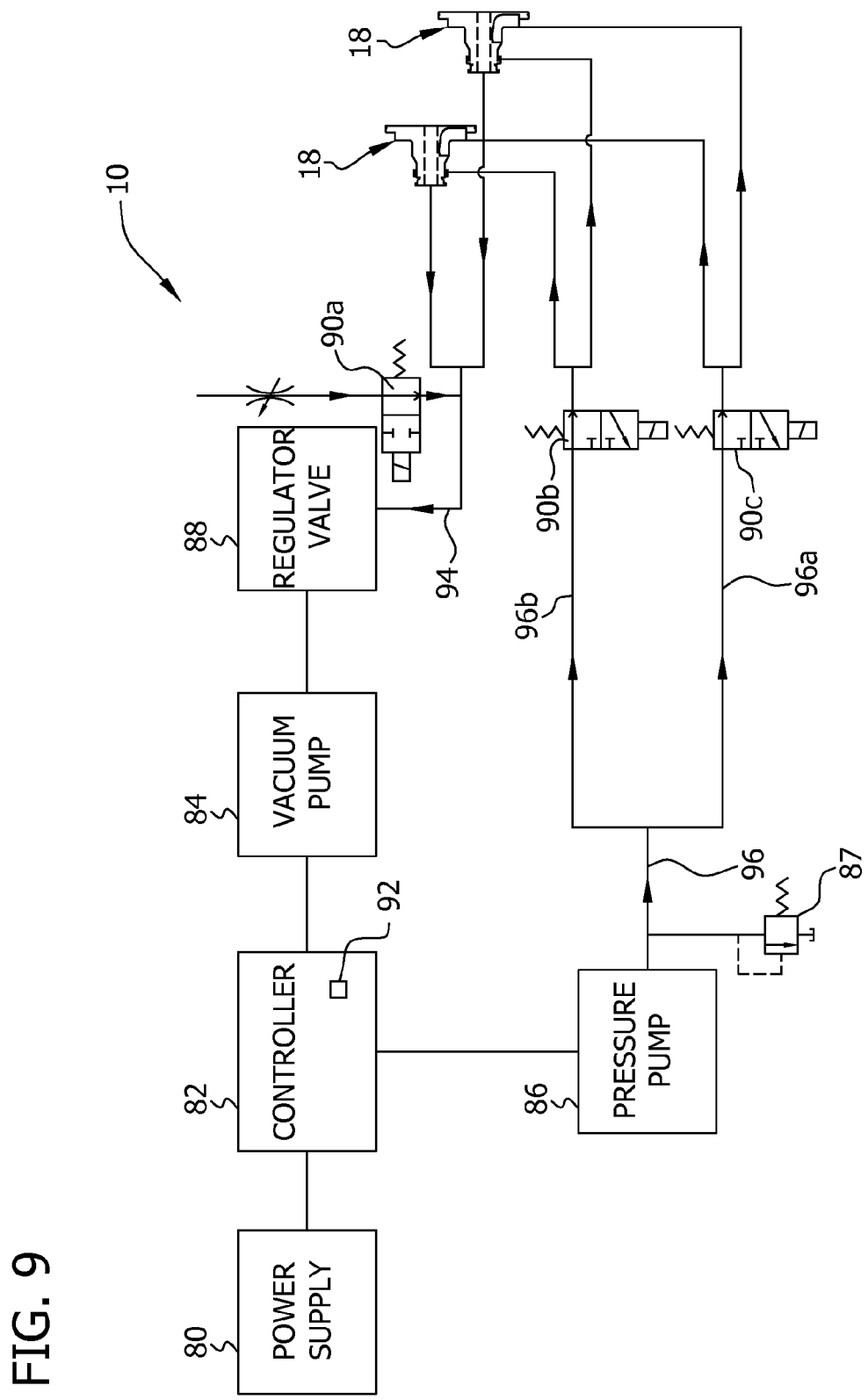
FIG. 9 is a schematic illustrating the interconnection of the various components of the electric breast pump.

With reference now to FIG. 9, the breast pump 10 also comprises a power supply 80, a controller 82, a vacuum pump 84, and a positive pressure pump 86. A regulator valve 88 (e.g., otherwise referred to as a relief valve may be suitably constructed in the manner of a screw-type adjustable valve) is in pneumatic communication with the vacuum pump 84 for adjusting the maximum operating (suction) vacuum pressure that can be applied by the vacuum pump to the mother's breast. Solenoid valves 90a-90c (e.g., three being illustrated in FIG. 9) are provided to regulate the timing of positive pressure and vacuum pressure applied to the cup assemblies 18 by the pressure pump 86 and vacuum pump 84, respectively. In one suitable embodiment, the power supply 80, the controller 82, the vacuum pump 84, the positive pressure pump 86, the regulator valve 88, and the solenoid valves 90a-90c are disposed in the housing 12.

In the illustrated embodiment, the power supply 80 provides sufficient power to operate the controller 82, the vacuum pump 84, the positive pressure pump 86, and the solenoid valves 90a-90c. The power supply 80 can be any suitable power source including an internal source (e.g., a rechargeable battery, one or more disposable batteries) or an external source (e.g., a standard 110 volt outlet, a power outlet in an automobile). In one suitable embodiment, the controller 82 is a programmable logic controller (PLC) that is specifically programmed to turn on and off the vacuum pump 84 and positive pressure pump 86 and to individually open and close each of the solenoid valves 90a-90c. The controller 82 includes an on/off switch 92 for allowing the nursing mother to selectively turn the breast pump 10 on and off.

The conduit 16, as illustrated in FIG. 1, comprises a vacuum conduit 94 pneumatically connecting the vacuum pump 84 via the regulator valve 88 and solenoid valve 90a to each of the collection assemblies and in particular to the central passage 70 of each of the cup assemblies 18. As such, it will be seen that the vacuum pump 84 draws a vacuum on the primary channel of the coupler 20, and thus on the secondary channel of the coupler and the central passage 70 of the cup assembly 18 (e.g., the central passage of the outer liner 40). One of the solenoid valves, e.g., valve 90a is disposed along the vacuum conduit 94 upstream of the collection assembly 14 to regulate the level of vacuum pressure applied by the vacuum pump 84 to the mother's breast within the central passage 70. That is, the solenoid valve 90a is controlled by the controller 82 and can be programmed to be closed or opened for a specified period of time.

In its opened position, the solenoid valve 90a vents the vacuum conduit to atmosphere to reduce or eliminate the vacuum pressure generated by the vacuum pump. In the illustrated embodiment, moving the solenoid valve 90a to its open position reduces the vacuum applied to the central passage 70 of each of the cup assemblies 18 to about 30 mm Hg. Moving the solenoid valve 90a to its closed position increases the vacuum applied to the central passage 70 of each of the cup assemblies 18 up to a maximum pressure. In one suitable embodiment, the vacuum pump 84 is capable of applying a maximum vacuum of up to 150 millimeters of mercury (mm Hg) to the central passages 70 of each of the cup assemblies 18. More suitably, in operation of the vacuum pump 84, the regulator valve 88 and the solenoid valve 90a are operated to regulate the vacuum pressure in the central passages 70 of the cup assemblies 18 (e.g., the vacuum pressure experienced by the mother's breast) in the range of about 70 mm Hg to about 130 mm Hg, more suitably in the range of about 75 mm Hg to about 125 mm Hg. It is understood, however, that the vacuum pump 84 can apply vacuum pressure other than within the above ranges without departing from the scope of this invention. It is important that the maximum pressure within the central passage 70 of each of the cup assemblies 18 be maintained below a level that would result in discomfort and/or tissue damage to the mother's breasts. The maximum pressure within the central passage 70 of each of the cup assemblies 18, however, should be sufficient to drive milk expressed from the mother breasts from the cup assemblies into the container 22.

One or more pressure conduits 96 (e.g., conduits 96a, 96b) pneumatically connect the pressure pump 86 to each of the collection assemblies 14 and more particularly to the first (via conduit 96a) and second (via conduit 96b) pressure chambers 60, 72 of the cup assemblies 18 (FIG. 9). Thus, positive pressure pump 86 can be used to independently pressurize the first interior chamber 60 and the second interior chamber 72 of each cup assembly 18 to selectively and independently expand the respective inner and outer liners 38, 40. In one embodiment, the positive pressure pump 86 is capable of pressurizing each of the first and second pressure chambers 60, 72 up to a maximum pressure established by a relief valve 87. In one suitable embodiment, the maximum pressure established by the relief valve 87 is about 85 mm Hg. It is understood, however, that the positive pressure pump 86 can pressurize the first and second interior chambers 60, 72 of the breast cups 18 between different ranges of positive pressure than those provided herein without departing from the scope of this invention.

One of the solenoid valves 90c is disposed along the first conduit 96a for selectively regulating the pressurization of the first pressure chamber 60, and another solenoid valve 90b is disposed along the second conduit 96b for selectively regulating the pressurization of the second pressure chamber 72. As mentioned above, the solenoid valves 90b, 90c are controlled by the controller 82 and can be programmed to be closed or opened for a specified period of time. Thus, the solenoid valves 90b, 90c along the first and second conduits 96a, 96b can be used in their opened positions to selectively pressurize the first and second interior chambers 60, 72 at any positive pressure within the limits of the pressure pump for a predetermined period of time. The solenoid valves 90b, 90c, which are three way valves, also facilitate independent venting or depressurization of the respective pressure chambers 60, 72. The solenoids valves 90b, 90c when moved to their closed position allow for selectively venting (in whole or in part) the first pressure chamber 60 and second interior chamber 72, respectively. Thus, the solenoid valve 90b, 90c along the first and second conduits 96a, 96b can be opened to selectively pressurize the first and second interior chambers 60, 72 and can be closed to selectively depressurize the first and second interior chambers for predetermined periods of time.

In the illustrated schematic, the cup assemblies 18 are operated simultaneously using the same solenoid valves 90a-90c. It is understood, however, that each of the cup assemblies 18 may be controlled independently of each other. That is, each of the cup assemblies 18 may be provided independent sets of solenoid valves with each respective set of solenoid valves controlled independently by the controller 82. It is also understood that the collection assemblies 14 and specifically the cup assemblies 18 described herein may be configured for use with a manual pump.

Operation of the breast pump 10 will now be described with reference to a single one of the collection assemblies 14, it being understood that operation of the other collection assembly is substantially the same as that described herein. In operation, the nursing mother brings the cup assembly 18 and in particular the outer liner 40 into contact with one of her breasts, with the nipple generally received through the elliptical opening 66 and into the central passage 70 of the cup assembly. In this position, the flange portion 62 and tapered portion 64 of the outer liner 40 lay against the mother's breast surrounding the nipple. The breast pump 10 is activated by moving the on/off switch 92 of the controller 82 to its on position, thereby initiating a pumping cycle of the breast pump.

The pumping cycle described herein is suitably designed to simulate the suckling action and frequency of a nursing infant, e.g., the peristaltic movement of the infant's tongue and palate. In particular, during each cycle the vacuum pump 84 is operated to apply a suction (e.g., maximum) vacuum pressure to the mother's breast within the central passage 70 of the outer liner 40. For example, a vacuum pressure in the range of about 75 mm Hg to about 125 mm Hg is applied to the breast within the central passage 70 of the outer liner 40. More specifically, the controller 82 closes the solenoid valve 90a to thereby allow the desired maximum vacuum pressure (as limited by the regulator valve 88) to be applied to mother's breast. The vacuum pressure acts on the mother's nipple to facilitate collection of milk expressed therefrom and aids in maintaining the cup assembly 18 on the mother's breast. In one particularly suitable embodiment, the suction vacuum pressure is applied to the mother's breast in the range of about 50 to about 80 percent of each cycle, and more suitably about 70 percent of each cycle.

The pressure pump 86 is operated to pressurize the first pressure chamber 60 (e.g., as defined by the inner liner 38) of the cup assembly 18 to apply a compressive pressure against the mother's breast at a location relatively distal from the end of the mother's nipple. For example, in one suitable embodiment, the first pressure chamber 60 is pressurized to a pressure of about 70 mm Hg to about 100 mm Hg, and more suitably about 85 mm Hg. This is done by the controller 82 opening the solenoid valve 90c disposed along the first conduit 96a of the pressure conduit 96 to pressurize the first pressure chamber 60. Pressurizing the first pressure chamber 60 in this manner causes the expansion of the inner liner 38 (and hence the outer liner 40 in the region of the inner liner) away from the support member 30 to apply pressure to the mother's breast within the central passage 70 of the outer liner 40. In one suitable embodiment, the first pressure chamber 60 is pressurized in the range of about 50 to about 80 percent of each cycle, and more suitably about 70 percent of each cycle.

At least about the same time that the first pressure chamber 60 is pressurized, and more suitably shortly thereafter, the second pressure chamber 72 (e.g., defined by the outer liner 40) is pressurized to apply a compressive pressure against the mother's breast at a location nearer to and in some embodiments adjacent the end of the mother's nipple. For example, in one suitable embodiment the second pressure chamber 72 is pressurized to a pressure of about 70 mm Hg to about 100 mm Hg, and more suitably about 85 mm Hg. In particular, the controller 82 opens the solenoid valve 90b disposed along the second conduit 96b of the pressure conduit 96 to pressurize the second pressure chamber 72 to the desired pressure. This causes the outer liner 70 to expand inward away from the support member 30 thereby reducing the height of the central passage 70 along the minor axis MIN to apply pressure to the mother's breast. In one embodiment, the pressure in the second pressure chamber 72 is suitably the same as the pressure in the first pressure chamber 60. It is understood, however, that the pressure in the second pressure chamber 72 may be greater than or less than that in the first pressure chamber 60 without departing from the scope of this invention.

In one suitable embodiment, the second pressure chamber 72 is pressurized in the range of about 30 to about 60 percent of each cycle, and more suitably about 50 percent of each cycle. In one particularly suitable embodiment, pressurization of the second pressure chamber 72 is delayed a suitable period following initial pressurization of the first pressure chamber 60 during each cycle such that the cycle time during which both the first and second pressure chambers are pressurized terminates at the same time during the cycle. As such, the first and second pressure chambers 60, 72 are pressurized sequentially to facilitate the flow of breast milk toward the mother's nipples where it can be expressed. Moreover, the hinged movement of the inner and outer liners 38, 40 in response to the vacuum pressure in the central passage 70 of the outer liner and the pressurization of the first and second pressure chambers 60, 72 more accurately simulates the tongue and palate movement of the suckling infant. Breast milk expressed from the mother's breast flows through the central passage 70 of the outer liner 70 into the secondary channel of the coupler 20, down into and through the primary channel thereof, and into the container 22.

Once both the first and second pressure chambers 60, 72 are fully pressurized during a suction cycle, the vacuum in the central passage 70 of the cup assembly 18 is reduced to about 30 mm Hg by the controller 82 opening the solenoid valve 90a only the vacuum conduit 94 to vent the vacuum path. The 30 mm Hg vacuum simulates the latching pressure of a suckling infant and also maintains the cup assembly 18 on the mother's breast.

Finally, both the first and second pressure chambers 60, 72 are vented by closing the corresponding solenoid valves 90c, 90b, which are three way valves, cause the chambers to depressurize to atmospheric pressure. Upon depressurization, the inner and outer liners 38, 40 return in large part (with the exception to any small deformation due to the latching pressure) to their initial or undeformed configuration. After the depressurization is complete, the solenoid valve 90a along the vacuum conduit 94 is closed so that the central passage 70 and hence the mother's breast therein is subjected to the suction vacuum pressure again for the next cycle.

The pumping cycle is repeated as often as necessary to express as much milk as the mother desires or is able to produce. The pumping cycle of the breast pump 10 is stopped by manually moving the on/off switch 92 of the controller 82 to the off position. In one suitable embodiment, the breast pump is operable in the range of about 50-90 cycles per minute, more suitably about 60-70 cycles per minute, and even more suitably about 60 cycles per minute (about 1 second per cycle). One example of a suitable pump cycle is summarized in the following table.

| Pump Cycle Time (seconds) | Positive Pressure in the first interior chamber (mm Hg) | Positive Pressure in the second interior chamber (mm Hg) | Vacuum applied to the Central Passage (mm Hg) |
|---|---|---|---|
| 0 | 70-100 | 0 | 70-175 |
| 0.2 | 70-100 | 70-100 | 70-175 |
| 0.5 | 70-100 | 70-100 | 30 |
| 0.7 | 0 | 0 | 70-175 |
| 1 | 70-100 | 0 | 70-175 |

The breast pump 10 described herein has been designed to more closely mimic the suckling of a nursing infant thereby providing a significantly more efficient and comfortable pump to mothers for expressing breast milk. More particularly, the breast pump 10 operates at a relatively low vacuum pressure as compared to conventional breast pumps, has a cup assembly with an elliptical opening (generally mouth shaped)

and capable of hinged movement at the opening, sequentially applies compressive pressure to the mother's breast, and operates through a timed cycle that is intended to simulate the peristaltic movement of an infant's tongue and palate.

Figure 10:
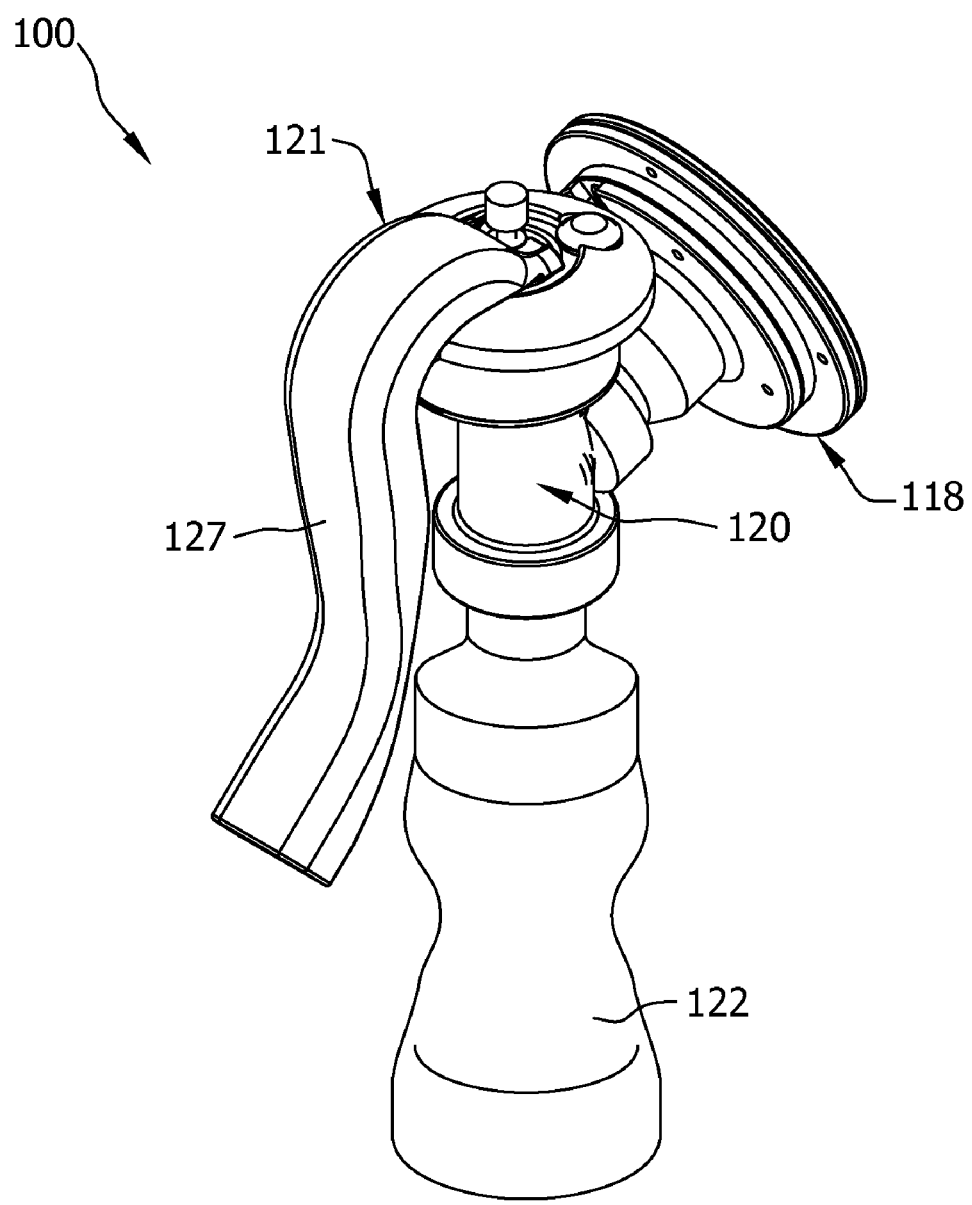
FIG. 10 is a perspective of one embodiment of a manual breast pump having a container attached thereto.

With reference now to FIGS. 10-19, and specifically FIG. 10, a manual breast pump according to one embodiment is indicated generally at 100. The illustrated manual breast pump 100 includes a pump, indicated generally at 121, a cup assembly, indicated generally at 118, a coupler 120, and a container 122 for receiving milk expressed from a nursing mother's breast by the breast pump. In the illustrated embodiment, the cup assembly 118, coupler 120, and container 122 are substantially similar to the cup assembly 18, coupler 20, and container 22 described above with respect to FIGS. 1-9. Thus, the illustrated container 122 is a bottle. It is understood, however, that other types of bottles and containers can be used to collect the expressed breast milk.

Figure 11:
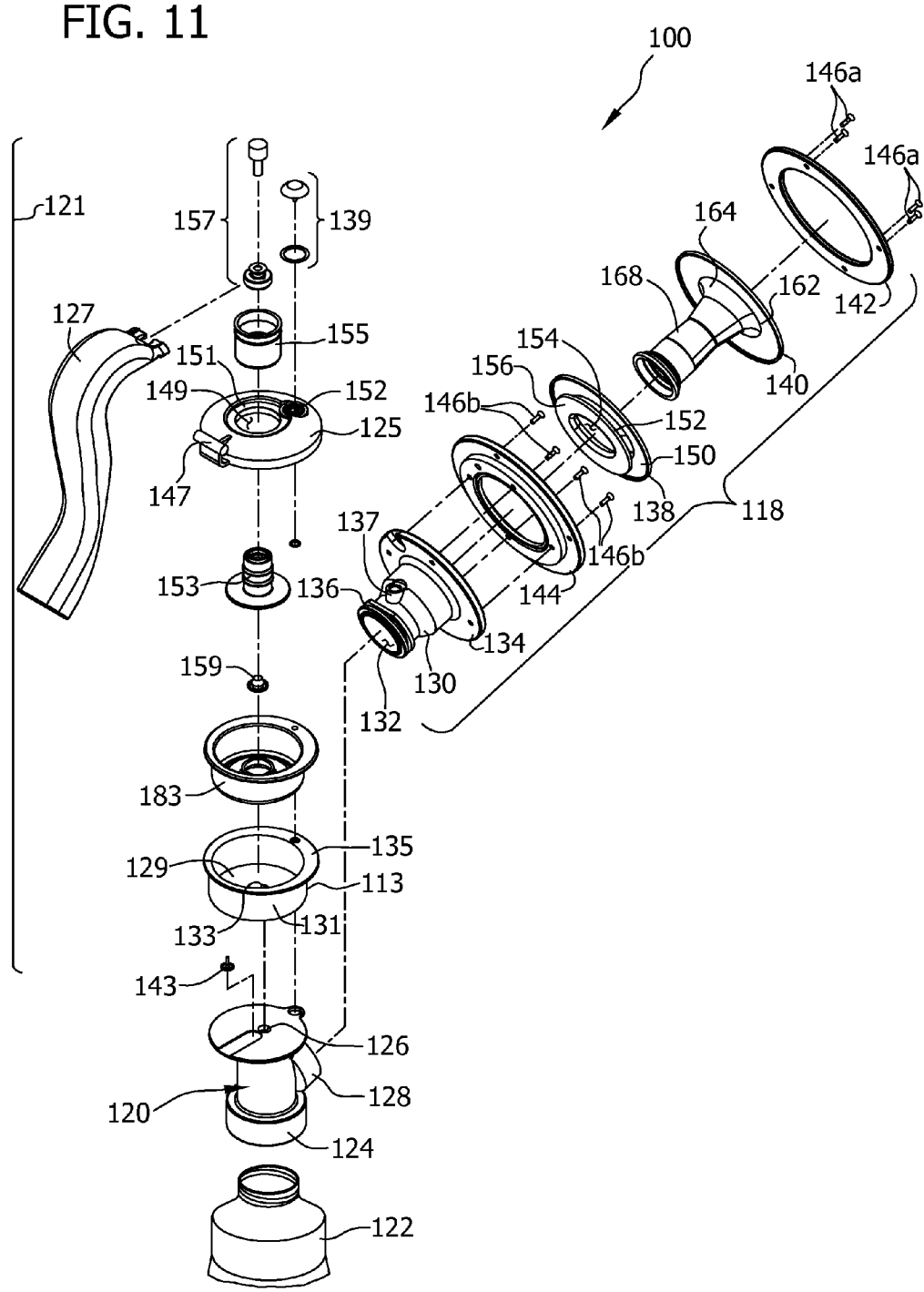
FIG. 11 is an exploded perspective of the manual breast pump with a portion of the container cut away.
Figure 12:
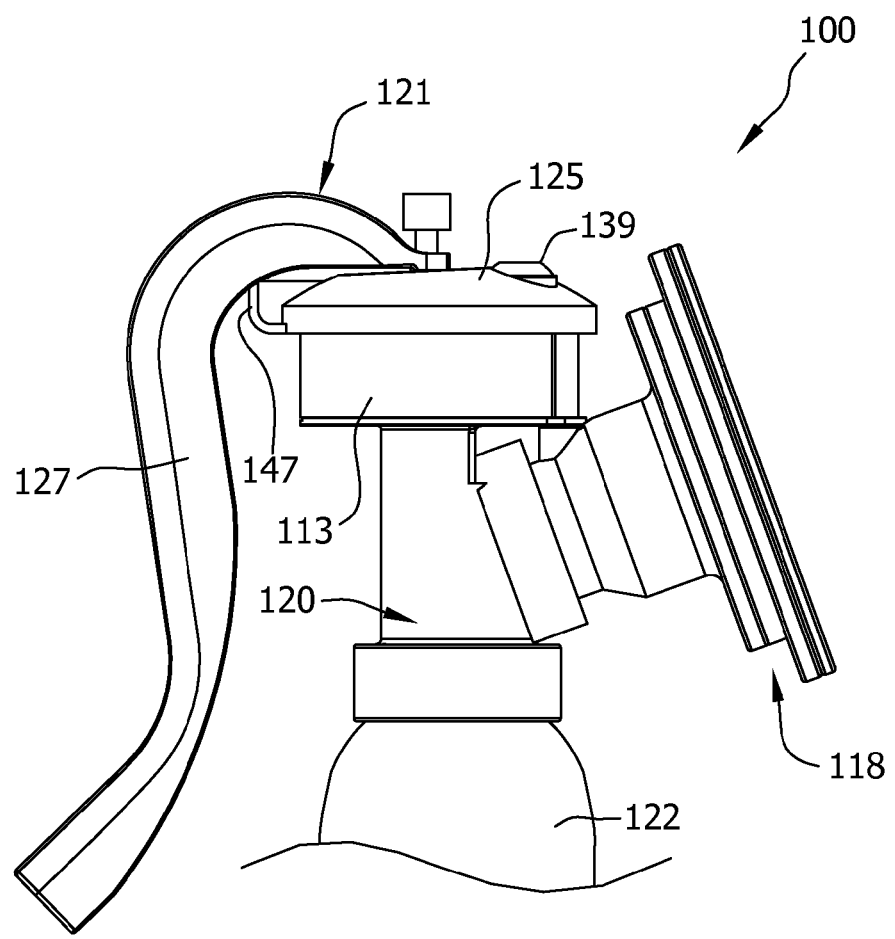
FIG. 12 is a side elevation of the manual breast pump.
Figure 13:
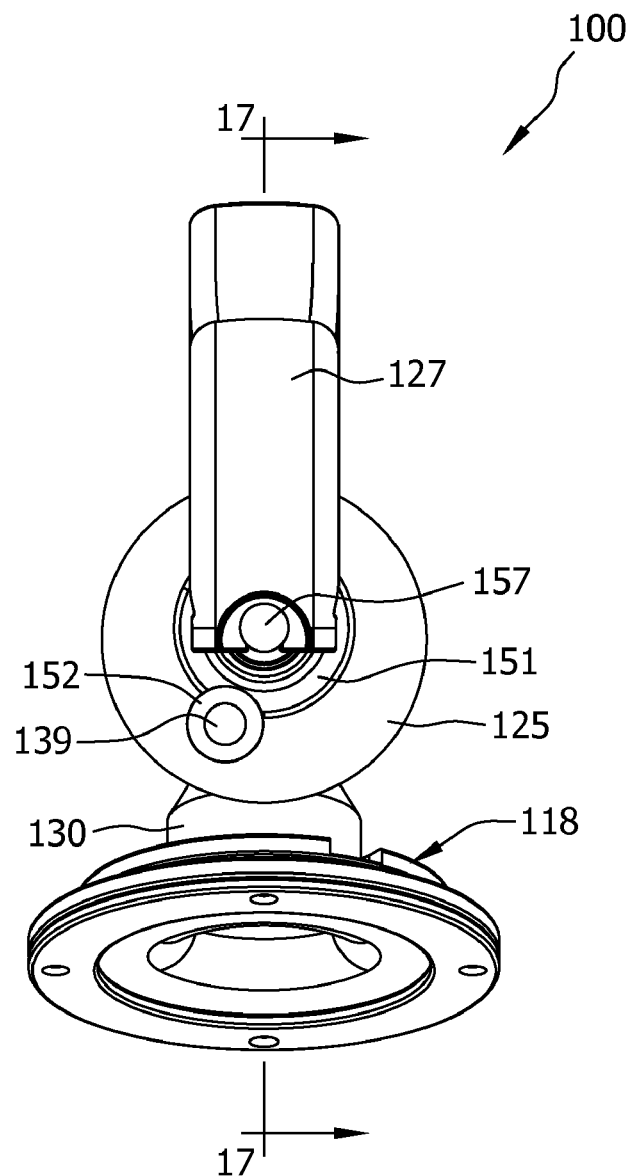
FIG. 13 is a plan view of the manual breast pump.
Figure 14:
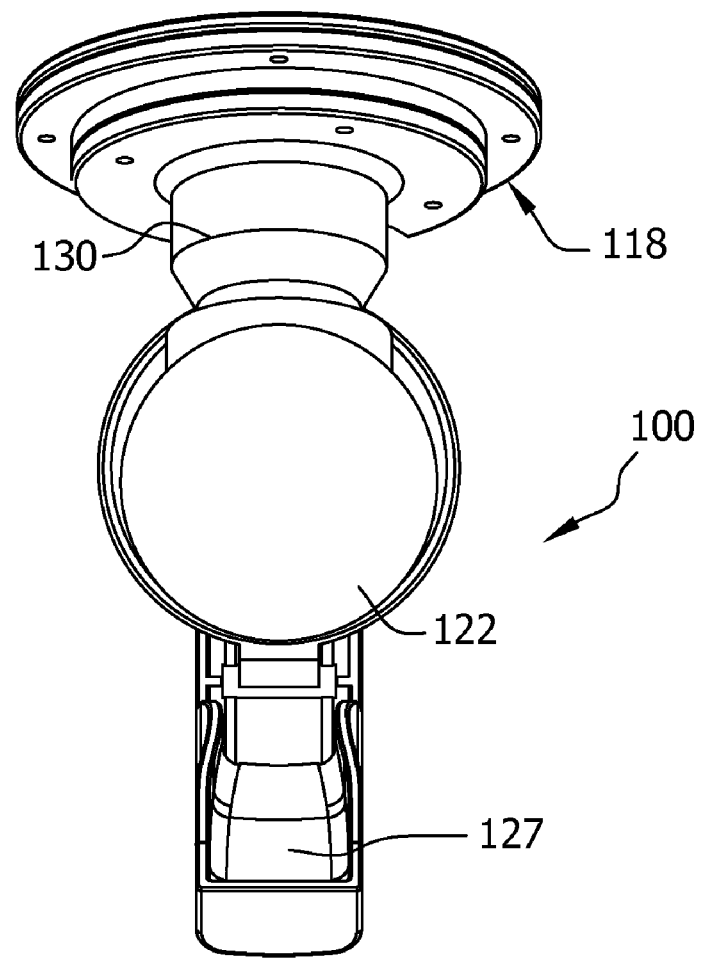
FIG. 14 is a bottom view of the manual breast pump.

In addition, the illustrated coupler 120 has a threaded lower socket 124 for threaded connection with the container 122, a port 126 for pneumatically connecting the coupler to the pump 121, and another port 128 for receiving the cup assembly 118 (FIG. 11). It is understood that couplers having other shapes and configurations can be used without departing from the scope of this invention. It is also understood that the coupler 120 may connect to the pump 121, the cup assembly 118, and/or container 122 in any suitable manner, such as, threads, barbs, and snap-fits.

With reference to FIG. 11, the cup assembly 118 is sized and shaped for receiving and forming a seal with the nursing mother's breast. Specifically, the cup assembly 118 comprises a support member 130 with a central passage 132 extending therethrough. The support member 130 includes a flange 134 at one end and threads 136 adjacent the opposite end for coupling the support member and thereby the cup assembly 118 to the coupler 120. The support member 130 of this embodiment includes a pressure port 137 for pneumatically connecting the assembly 118 to the pump 121. The cup assembly 118 also includes an inner liner 138, an outer liner 140, and a pair of mounting collars or rings (an outer mounting ring 142 and an inner mounting ring 144) for securing the inner and outer liners to the support member 130. Suitable fasteners 146a, 146b (e.g., bolts, screws, rivets) are used to secure the mounting rings 142, 144 to the flange 134 of the support member 130 to sealing clamp the inner and outer liners 138, 140 therebetween. It is understood that the inner and outer liners 138, 140 can be secured to the support member 130 in other ways.

Figure 17:
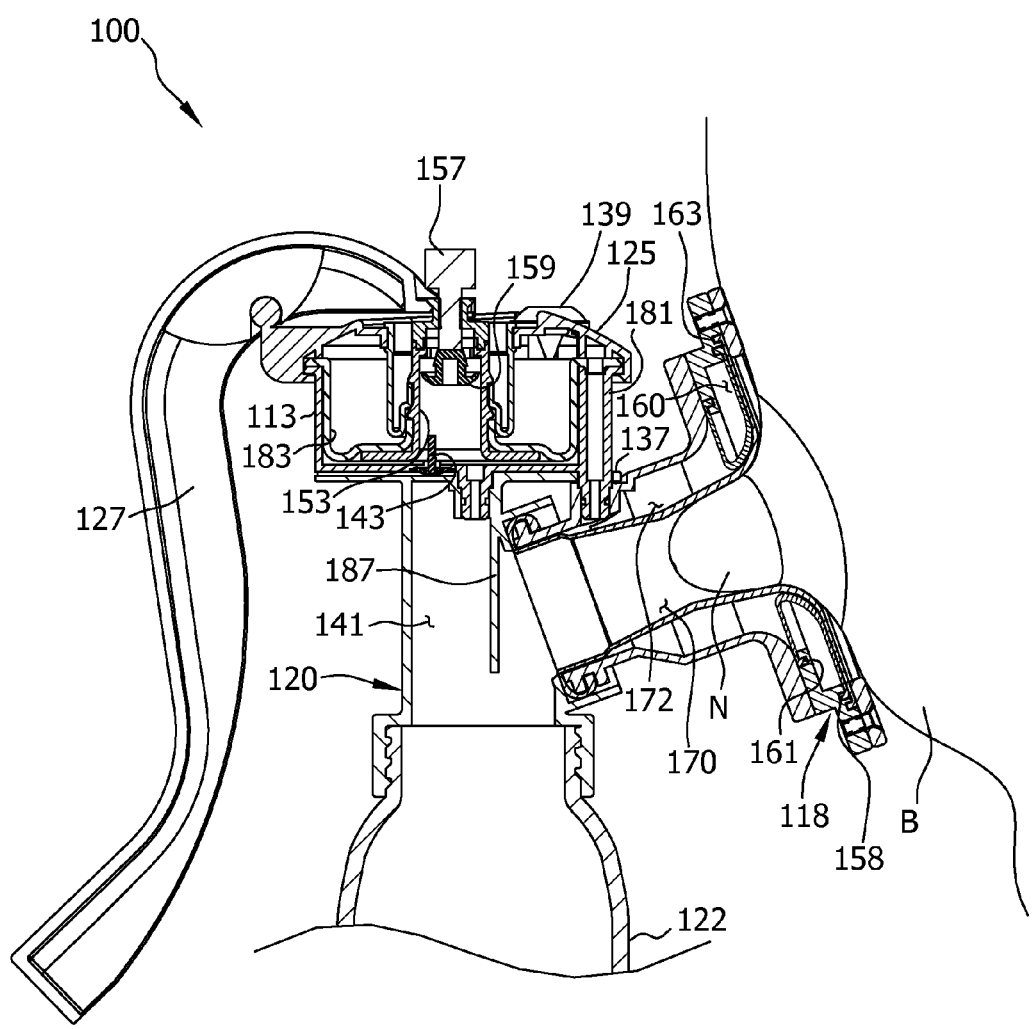
FIG. 17 is a cross-section of the manual breast pump taken along line 17-17 of FIG. 12 with a handle of the pump in a relaxed position.
Figure 18:
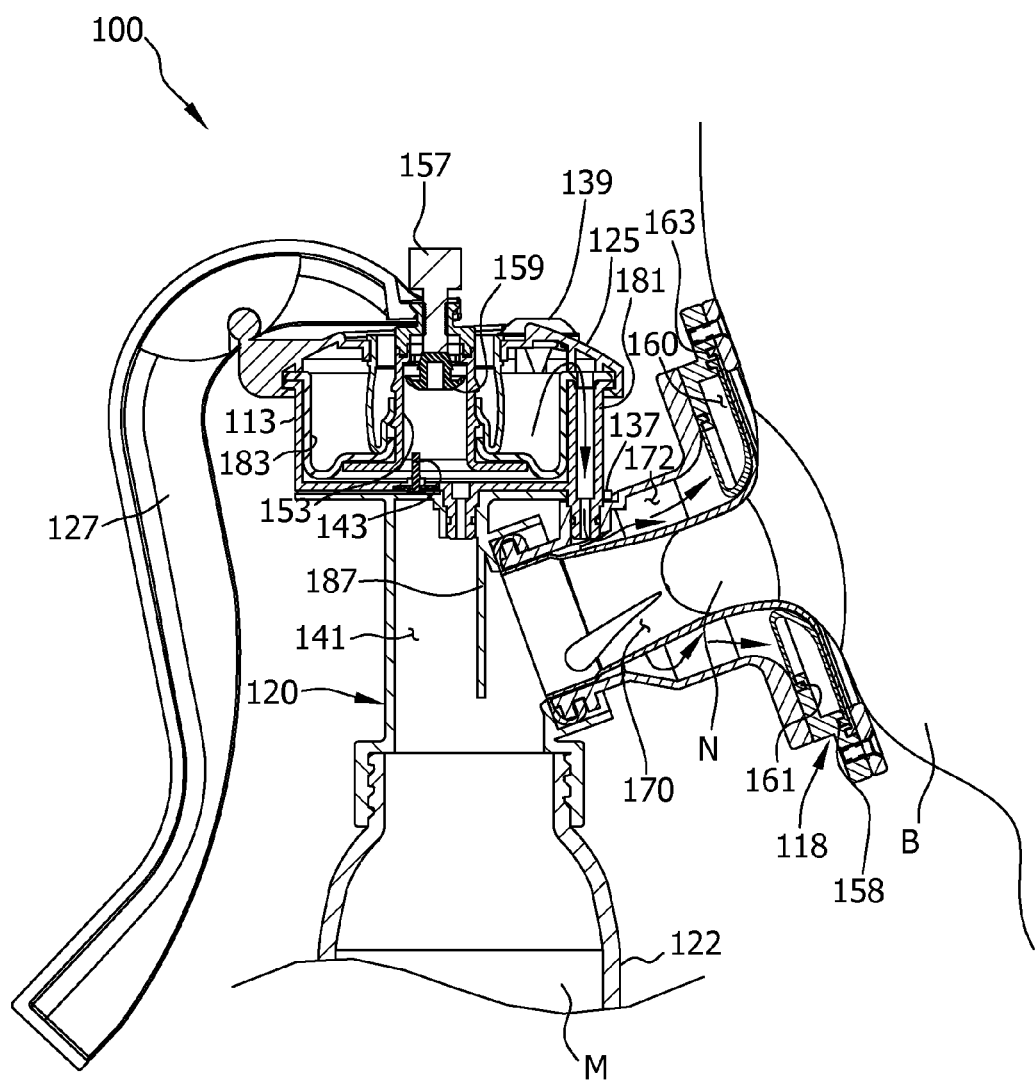
FIG. 18 is a cross-section similar to FIG. 17 but with the pump handle in a partially compressed position.
Figure 19:
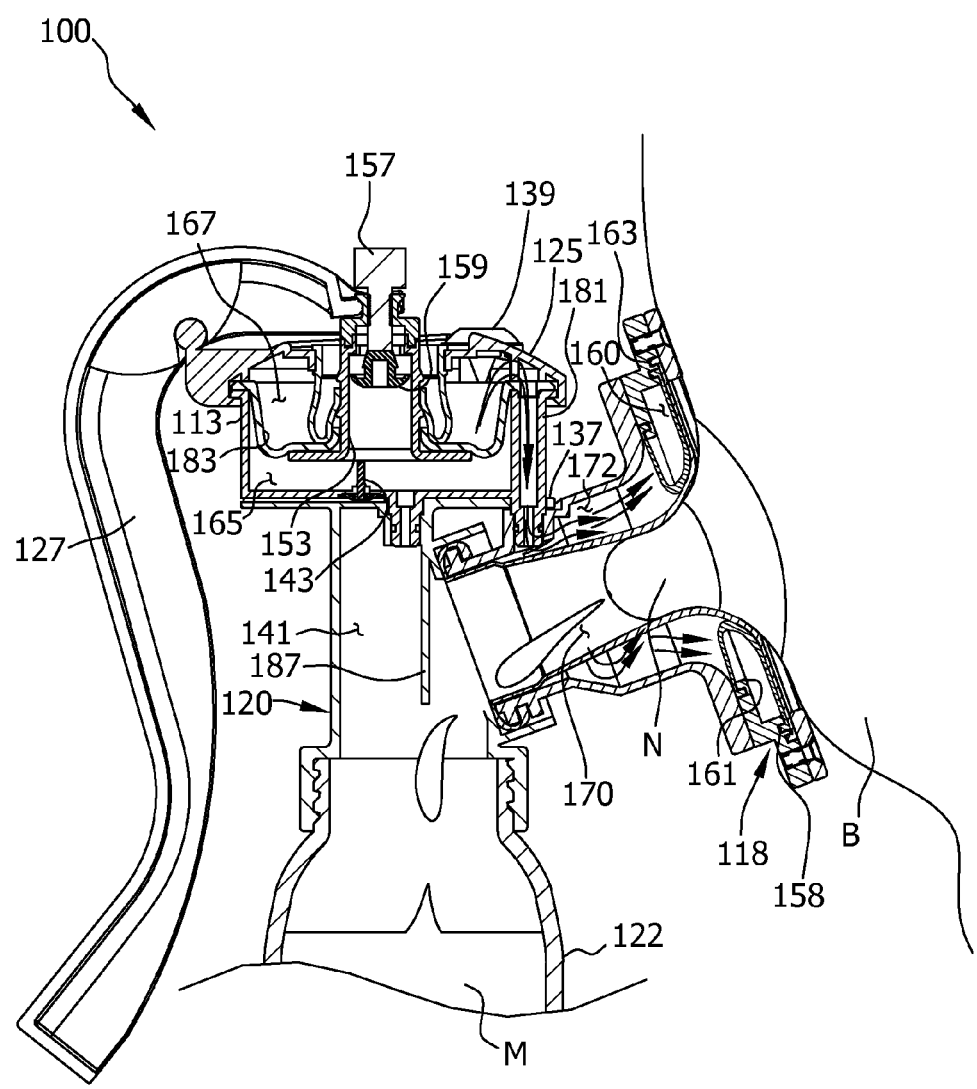
FIG. 19 is a cross-section similar to FIGS. 17 and 18 but with the pump handle in a fully compressed position.

The inner liner 138 includes a first flange portion 150, a tapered portion 152 extending inward from the first flange portion, and a generally elliptical, central opening 154 that is defined by the tapered portion. The inner liner 138 also includes a second flange portion 156 that is spaced from the first flange portion 150 and extends generally parallel thereto. The first flange portion 150 and the second flange portion 156 include inwardly extending annular ribs 158, 161, respectively, for being received in respective annular grooves in the inner mounting ring 144 (FIGS. 17-19). The inner liner 138 and the inner mounting ring 144 cooperatively define a first pressure chamber 160 of the cup assembly 118.

Figure 15:
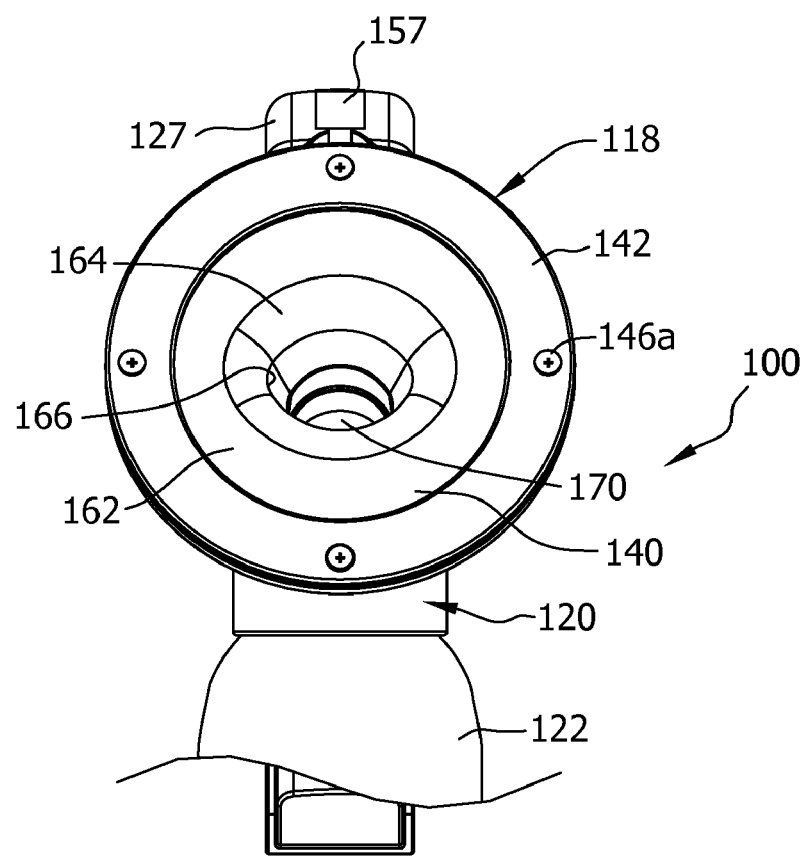
FIG. 15 is a front view of the manual breast pump.
Figure 16:
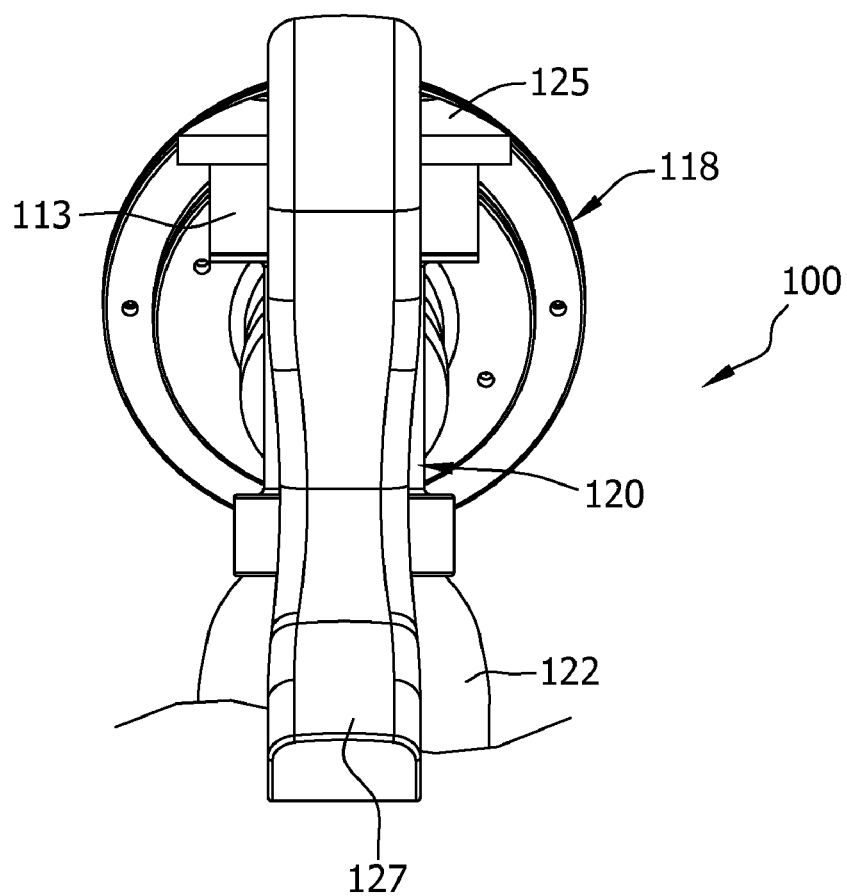
FIG. 16 is a back view of the manual breast pump.

With reference to FIGS. 11 and 15, the outer liner 140 includes a first flange portion 162, a tapered portion 164 extending inward from the first flange portion, and a generally elliptical, central opening 166 that is defined by the tapered portion. As illustrated in FIGS. 17-19, the first flange portion 162 includes an annular rib 163 for being received in an annular groove in the inner mounting ring 144. The outer liner 140 also includes tubular portion 168 extending outward from the tapered portion 164. The tubular portion 168 is receiving through the central passage 132 of the support member 130 and defines a central passage 170 of the cup assembly 118. With reference still to FIGS. 17-19, the tubular portion 168 of the outer liner 140 cooperates with the support member 130 and inner liner 138 to define a second pressure chamber 172.

As illustrated in FIG. 11, the pump 121 includes a pump housing 113 and a lid 125 for closing the housing. The pump housing 113 of the illustrated embodiment is generally cup shaped having a generally flat bottom 129 adapted to sit on an upper surface of the coupler 120, and a cylindrical wall 131 extending upward from the bottom. An annular flange 135 extends around the periphery of the cylindrical wall 131. A conduit 181 is formed in the housing 113 and adapted to connect to the pressure port 137 formed in the cup assembly 118 (FIGS. 17-19). The bottom 129 of the housing 113 includes an aperture 133 in pneumatic communication with the port 126 in the coupler 120 and thereby an interior chamber 141 of the coupler.

With reference again to FIG. 11, the lid 125 has a mount 147 for pivotally mounting a handle 127 of the pump 121 thereon, and a central opening 149 with an adjacent annular recess 151 surrounding the opening. The lid 125 also includes a vent passage 152. A pressure relief valve 139 is operatively mounted onto the lid 125 and pneumatically connected to the vent passageway 152 and thereby the conduit 181 in the housing 113. The valve 139 vents the pressure chamber in the pump 121 and correspondingly the pressure chamber 160, 172 in the cup assemblies 118. With reference still to FIG. 11, a check valve 143 is associated with an aperture (not shown) in the housing 113. The check valve 143 inhibits positive pressure in the vacuum chamber of the pump.

The handle 127 of the illustrated embodiment of the pump 121 is generally S-shaped and is pivotally mounted on the mount 147 of the lid 125 via a snap-connection therewith. The handle 127 can be manually squeezed and released to operate the pump 121. Thus, the handle 127 can be selectively moved between a relaxed position (FIG. 17) and a compressed position (FIG. 19). It is understood that the handle can have other shapes and configurations.

A lift assembly comprises a stem 153, a bellows 155, a thumb screw 157, and an umbrella valve 159 and is received through the central opening 149 in the lid 125. The stem 153, as illustrated in FIGS. 17-19, includes a tubular wall, a closed upper end, and an opened lower end. The upper end includes an aperture and the lower end includes an annular flange. A pair of spaced apart ribs is disposed on an exterior surface of the tubular wall. The bellows 155 is a flexible membrane that extends through the central opening 149 of the lid 125 and is affixed at one end to the lid about the shoulder 151 surround central opening. The opposite end of the bellows 155 is affixed to the stem 153 between the pair of ribs. The thumb screw 157 of the lift assembly extends through the aperture in the upper end of the stem 153 and is operatively connected to the umbrella valve 157, which is disposed within the tubular stem. The stem 153 is operatively connected to the handle 127 so that movement of the handle results in corresponding movement of the lift assembly.

As seen in FIGS. 17-19, a diaphragm 183 is received in the pump housing 113 and comprises a flexible membrane. One end of the diaphragm 183 is captured between the lid 125 and the pump housing 113 and is affixed at its opposite end to the stem 153. As best illustrated in FIG. 19, the diaphragm 183 and the pump housing 113 collectively define a vacuum chamber 165 for inducing a vacuum in the interior chamber 141 of the coupler 120 and thereby the central passage 170 of the cup assembly 118. The diaphragm 183, the lid 125, and the bellows 155 collectively define a pressure chamber 167 for pressurizing the inner and outer pressure chambers 160, 172 of the cup assembly 118.

During operation of the manual breast pump 100, which is illustrated in FIGS. 17-19, the nursing mother grasps the pump and brings the cup assembly 118 into contact with one of her breasts B such that her nipple N is received into the central passage 170 of the cup assembly. The outer liner 140 contacts the mother's nipple N and portions of her breast B around her nipple. Next, the breast pump 100 is activated by the mother squeezing the handle 127 to drive the pump 121 through one complete pumping cycle of the pump.

As the mother squeezes the handle 127, the handle moves toward the coupler 120 and pivots about the mount 147 on the lid 125 to lift the stem 153 and thereby the lift assembly upward toward the lid. The stem 153 carries the thumb screw 157, the umbrella valve 159, the bellows 155, and diaphragm 183 with it as it moves upward. Upward movement of the diaphragm 183 causes the volume of the vacuum chamber 165 to increase thereby creating a vacuum in the interior chamber 141 of the coupler 120 and the central passage 170 of the cup assembly 118, which results in a vacuum being applied to mother's nipple N received in the central passage of the cup assembly 118. In one suitable embodiment, the vacuum applied to the central passage 170 of the cup assembly and thereby the mother's nipple N is in the range of 70 mm Hg to about 125 mm Hg. The amount of vacuum applied to the mother's nipple N can in some embodiments be variable within this range by rotation of the thumb screw 157, which correspondingly adjusts the position of the umbrella valve 159. More specifically, the thumb screw 157 pushes on a stem of the umbrella valve 157 thereby decreasing the stem tension, which reduces the pressure differential at which the umbrella valve opens. This provides better control of the range of the valve with less sensitivity. The umbrella valve 159 provides a relief valve, which opens to reduce the vacuum within the vacuum chamber 165 should the vacuum with the vacuum chamber exceed the predetermined value.

The volume of the pressure chamber 167 is deceased as the lift assembly is raised during pivotal movement of the handle 127, which causes air to flow out of the pressure chamber and into the first and second pressure chambers 160, 172 of the breast cup via the conduit 181 of the pump housing 113 and the pressure port 137 of the breast cup. Filling the first and second interior chambers 160, 172 with air causes them to pressurize. In the illustrated embodiment, the first and second pressure chambers 160, 172 are pressurized simultaneously but it is contemplated that the first pressure chamber may be pressurized first followed by pressurization of the second chamber. Pressurization of the first and second pressure chambers 160, 172 results in a compressive force being applied to the mother's nipple N and a portion of the mother' breast B around her nipple thereby driving milk M within her breast toward her nipple. In one suitable embodiment, the first and second interior chambers 160, 172 of the cup assembly 118 are pressurized to a pressure between about 70 mm Hg to about 100 mm Hg. The pressure relief valve 139 prevents the pressure within the pressure chamber 167 from exceeding the predetermined suction vacuum pressure. The pressure relieve valve 139 of the illustrated embodiment is fixed to relieve pressure at a predetermined value.

As seen in FIG. 19, milk M expressed from the mother's breast B flows through the central passage 170 of the cup assembly 118, through the interior chamber 141 of the coupler 120 and into the container 122 by gravity. A partition 187 is located in the coupler to prevent milk M from flowing toward the pump housing 113.

The pumping cycle is repeated as often as necessary to express as much milk as the mother desires or is able to produce. The total pump cycle time of each pumping cycle is directly dependent on the rate at which the mother squeezes the handle 127. The faster the mother squeezes and releases the handle 127, the faster the pump cycle rate. The breast pump 100 described herein has been designed to more closely mimic the suckling of a nursing infant thereby providing a significantly more efficient and comfortable pump to mothers for expressing breast milk. More particularly, the breast pump 100 operates at a relatively low vacuum pressure as compared to conventional manual breast pumps, has a breast cup with an elliptical opening (generally mouth shaped) for receiving the nipple of the mother's breast and capable of applying a compressive force to the mother's breast around her nipple.

Figure 20:
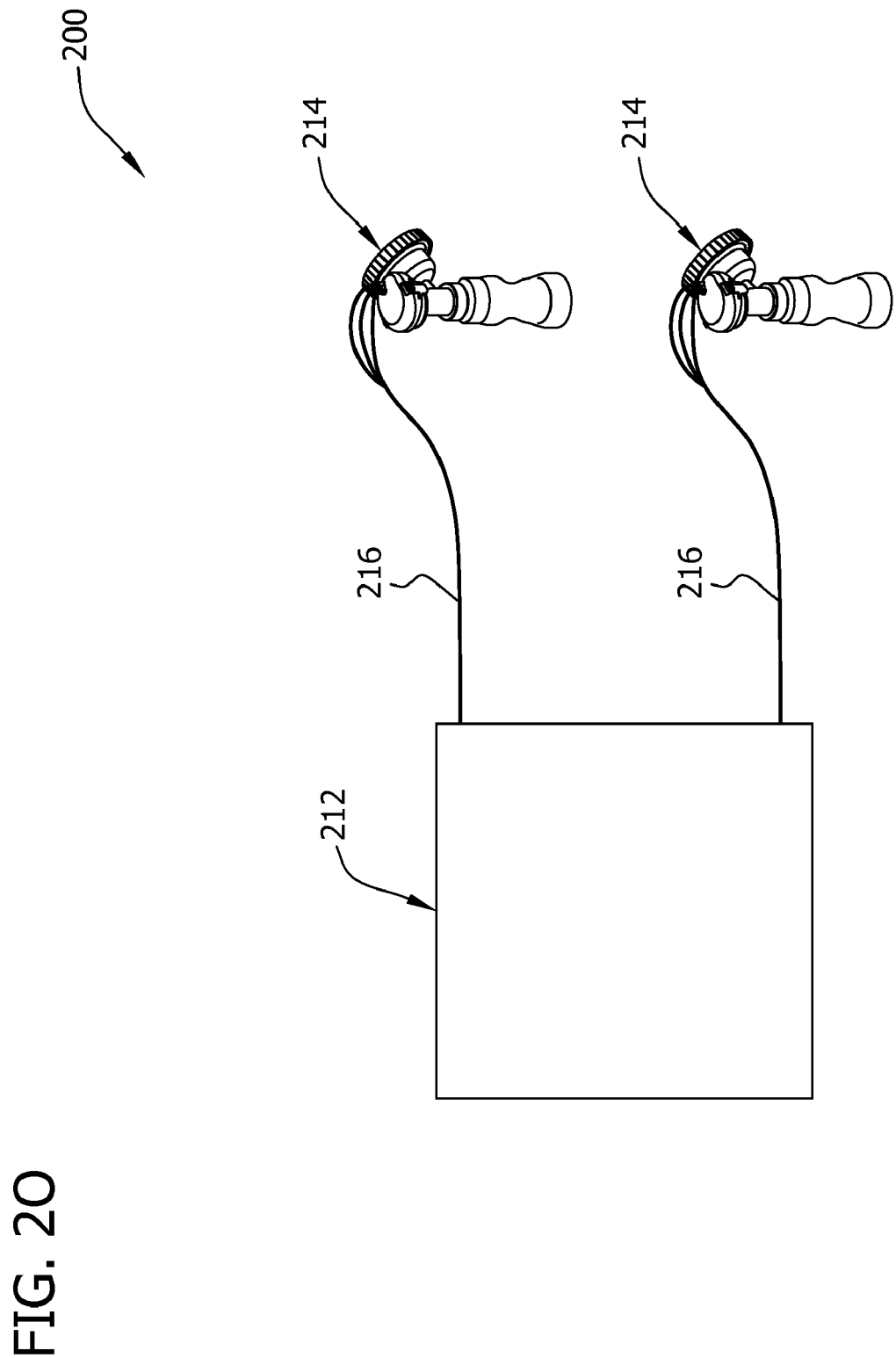
FIG. 20 is a schematic of another embodiment of an electric breast pump.

With reference now to FIG. 20, an electric breast pump according to another embodiment is schematically illustrated and is indicated generally at 200. The breast pump 200 includes a suitable housing, indicated generally at 212, for housing various working components such as pumps, a controller, and other components as will be described later herein. The breast pump 200 also comprises a pair of collection assemblies, indicated generally at 214, and flexible tubing or conduits 216 pneumatically connecting the collection assemblies to the housing. The housing 212 can be any suitable housing sized and configured for containing various components of the breast pump 200. The illustrated breast pump 200 includes a pair of collection assemblies 214 for expressing milk from both of a nursing mother's breasts, either simultaneously or independent of each other. It is contemplated that the collection assemblies 214 can be sufficiently independently operable so that a nursing mother can use only one of the two collection assemblies to express milk from a single breast. It is also contemplated that the breast pump 200 can be provided with a single collection assembly 214 for expressing milk from each of the nursing mother's breasts separately.

Figure 21:
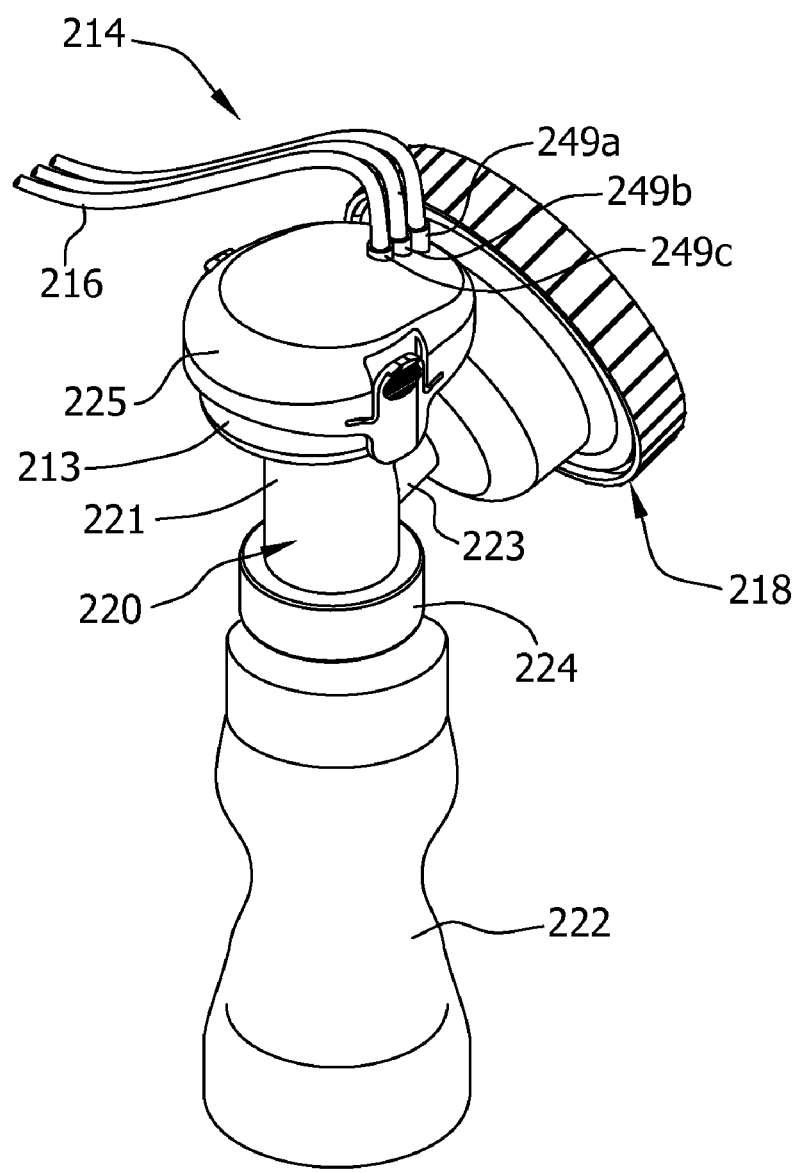
FIG. 21 is an enlarged perspective of one collection assembly of the breast pump of FIG. 20.

As illustrated in FIG. 21, each of the collection assemblies 214 comprises a cup assembly, indicated generally at 218, a coupler 220, and a container 222 for collecting milk expressed from the nursing mother's breast. In the illustrated embodiment, the container 222 is a conventional nursing bottle. It is understood, however, that other types of bottles and containers can be used to collect the expressed breast milk. For example, the container 222 can be a dedicated milk storage bottle (e.g., a relatively small amber or green bottle that minimizes the amount air in the bottle and the amount of light that penetrates the bottle).

Figure 25:
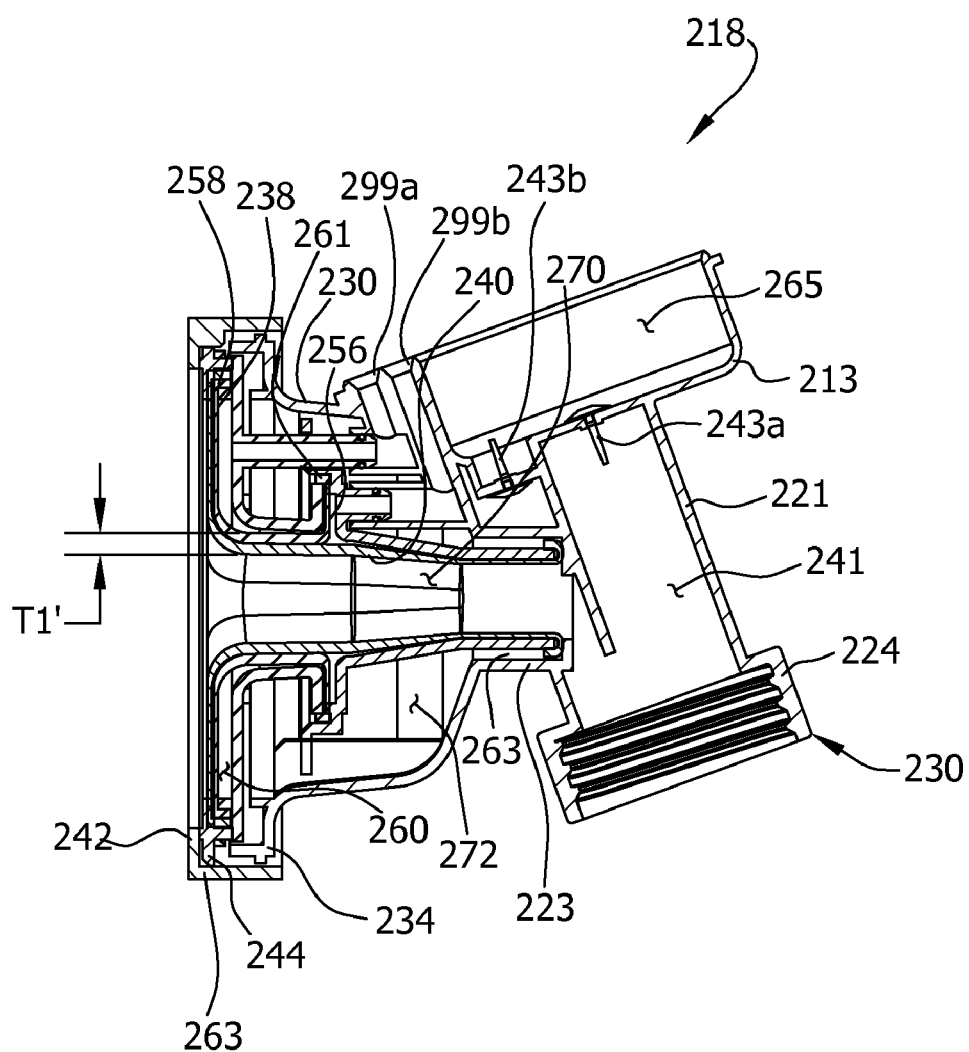
FIG. 25 is a cross-section taken along line 25-25 of FIG. 24A.

As seen in FIG. 25, the coupler 220 has a primary tubular segment 221 defining a primary channel 241 oriented vertically in the drawings (e.g., to simulate the general orientation of the collection assembly in use), and a secondary tubular segment 223 extending outward from the primary segment at an angle relative thereto and defining a secondary channel 263 within the coupler. The coupler 220 includes a threaded lower socket 224, e.g., at the lower end of the primary segment 221, for threaded connection with the container 222 to couple the container to the coupler. The cup assembly 218 is mounted on the coupler 220 at the distal end of the secondary segment 223 to provide pneumatic and fluid communication between the cup assembly and the container 222 via the coupler. It is understood that couplers having other shapes and configurations can be used without departing from the scope of this invention. It is also understood that the coupler 220 may connect to the cup assembly 218, and/or container 222 in any suitable manner, such as, threads, and snap-fits, or other connection.

Figure 22:
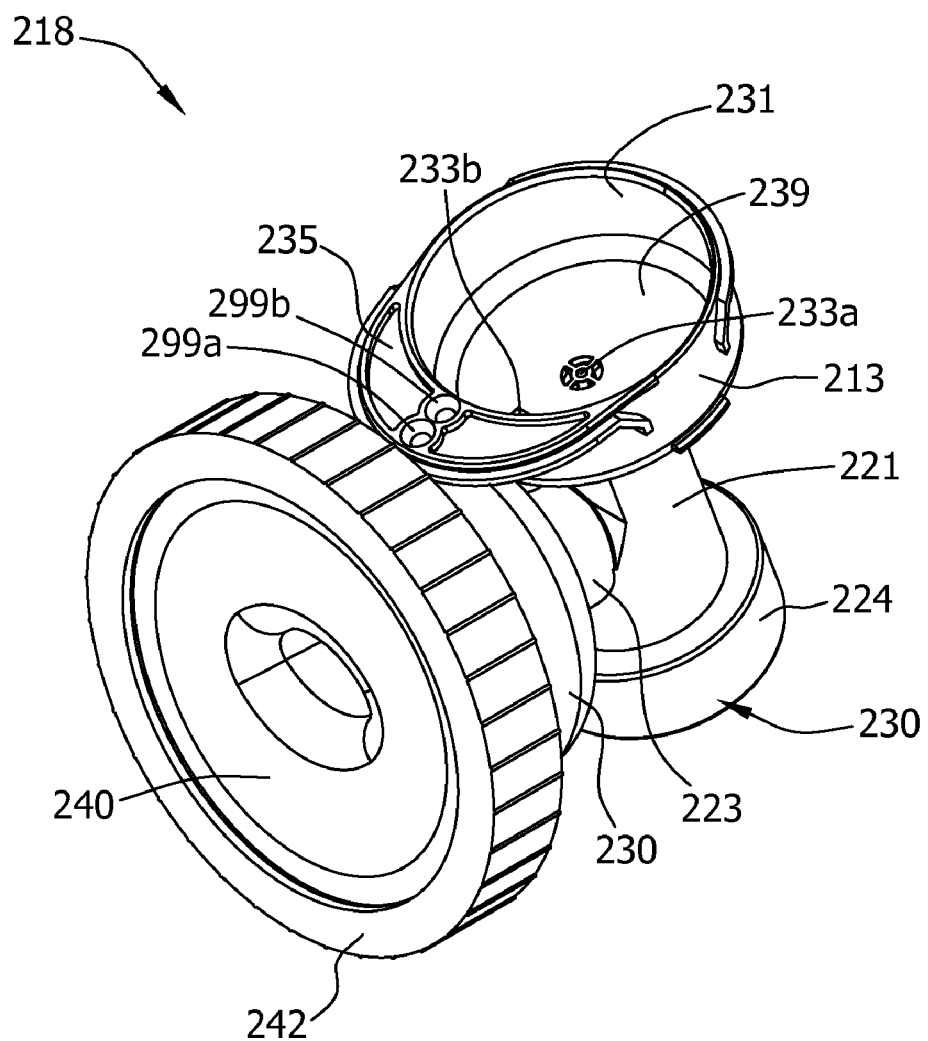
FIG. 22 is a perspective of a cup assembly of the collection assembly of FIG. 21.
Figure 23:
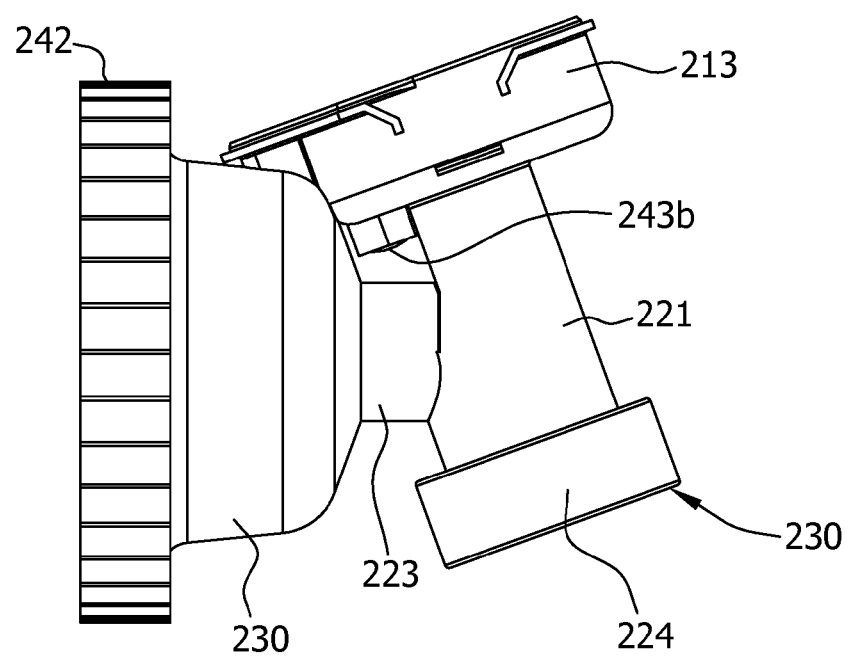
FIG. 23 is a side elevation of the cup assembly.

The coupler 220 also includes a generally cup-shaped housing 213 located above the primary segment 221. As illustrated in FIG. 22, the housing 213 of the illustrated embodiment has a generally flat bottom 229 and a cylindrical wall 231 extending upward from the bottom. A flange 235 extends at least partially around the periphery of the cylindrical wall 231. The flange 235 includes two port openings 299a, 299b. The bottom 229 of the housing 213 includes a first aperture 233a in pneumatic communication with the primary channel 241 of the coupler 220 and a second aperture 233b in pneumatic communication with the atmosphere (i.e., the area outside of the housing).

A check valve 243a is associated with the aperture 233a in the housing 213 for allowing air to be drawn from the primary channel 241 of the coupler 220 into the housing 213. The check valve 243a, however, inhibits air from flowing in the opposite direction. That is, the check valve 243 inhibits air from flowing from the housing 213 into the primary channel 241 of the coupler 220. As a result, a vacuum or negative pressure can readily be applied to the primary channel 241 of the coupler 241 while pressurization of the primary channel of the coupler is inhibited. It is contemplated that in some embodiments the check valve 243a associated with the aperture 233a in the housing 213 can be omitted. A relief valve 243b is associated with the aperture 233b in the housing 213 for allowing air to be drawn into the housing from the atmosphere should the vacuum within the housing exceed a predetermined threshold.

As seen in FIG. 21, a lid or cap 225 is mounted (e.g., by suitable threading, by snap fit, or other suitable mounting arrangement) on the coupler 220 at its top to sealingly close the coupler. More specifically, the lid 225 is mounted by snap fit on the housing 213 of the coupler 220. The lid 225 also includes three ports 249a, 249b, 249c. Two of the ports 249a, 249b are pneumatically connected to respective ones of the openings 299a, 299b in the flange 235 of the housing 213. The other port 249c is in pneumatic communication with an interior chamber 265 of the housing.

Figure 26:
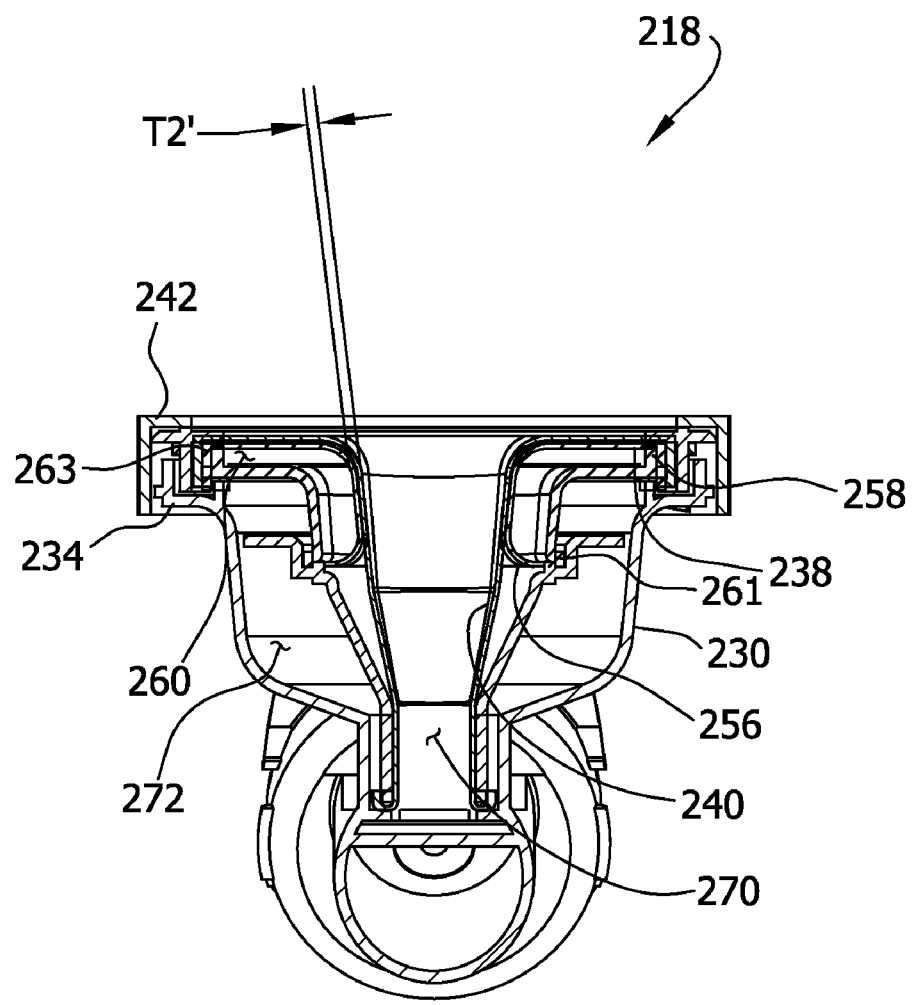
FIG. 26 is a cross-section taken along line 26-26 of FIG. 24A.
Figure 27:
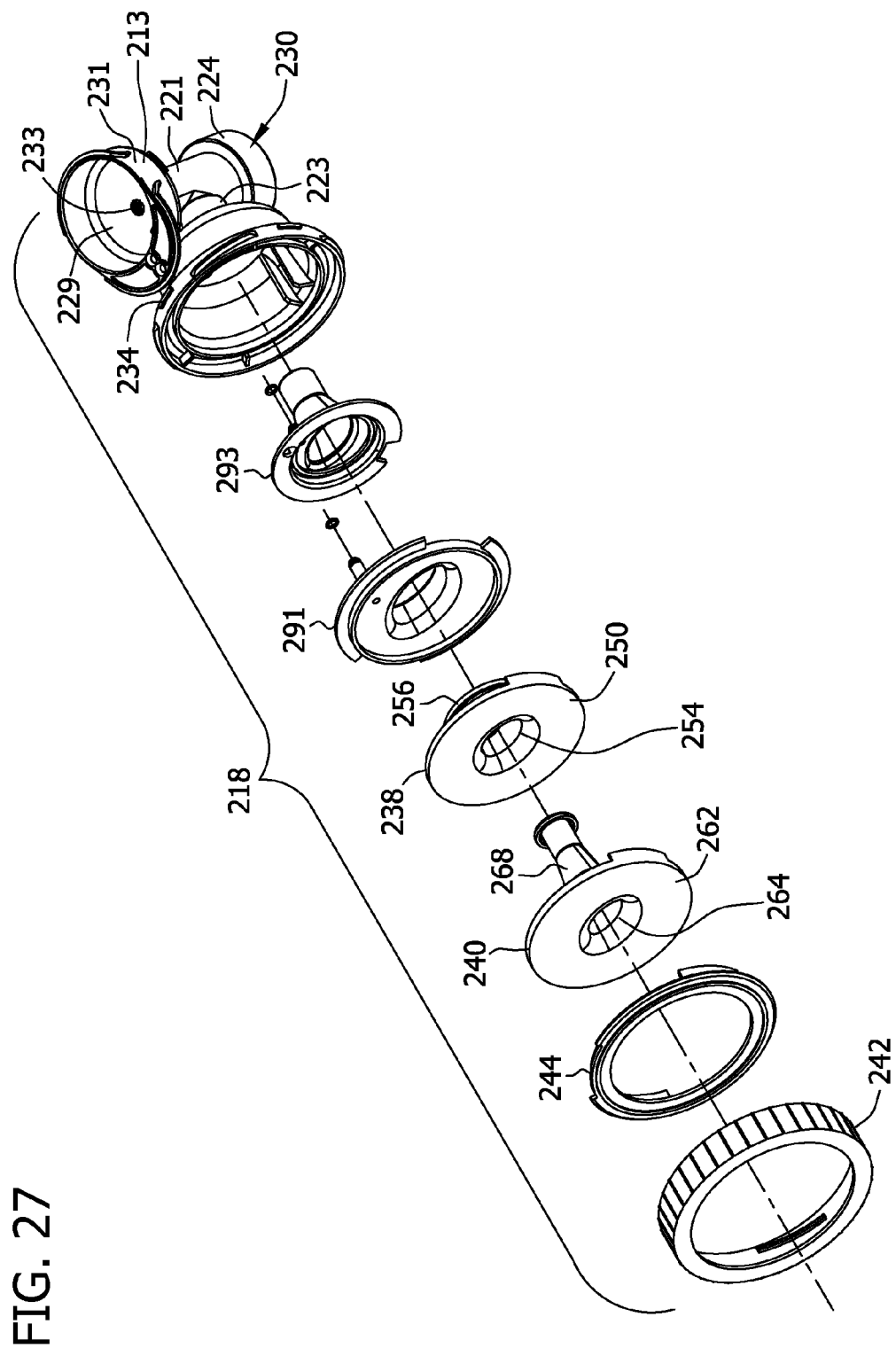
FIG. 27 is an exploded perspective of the cup assembly.

With reference to FIGS. 22-27, each cup assembly 218 is sized and shaped for receiving and forming a seal with one of the nursing mother's breasts, particularly at one of the mother's nipples. Specifically, each of the cup assemblies 218 comprises a generally tubular, and more particularly a generally funnel-shaped, support member 230 having an interior or central passage 232 extending longitudinally therethrough (FIG. 25). As seen in FIG. 27, the support member 230 has a flanged longitudinally outer end 234 with external threads. In this embodiment, the support member 230 of the cup assembly 218 is formed as a single-piece with the coupler 220 and the housing 212. The unitary coupler 220, housing 212, and support member 230 may be constructed of any suitable material but in a particularly suitable embodiment is sufficiently resistant to deformation in response to positive or negative pressure applied thereto at the operating pressures of the pump. For example, the unitary coupler 220, housing 212, and support member 230 may be suitably constructed of a generally rigid plastic. It is understood that the coupler 220, housing 212, and support member 230 can be formed separately and attached together in any suitable manner.

With reference to FIG. 27, the cup assembly 218 further comprises a pair of expandable liners, referred to herein as inner liner 238 and outer liner 240. A pair of mounting inserts (e.g., an outer insert 291 and an inner insert 293) mounts the inner and outer liners 238, 240 on the support member 230 of the cup assembly 218. A thread collar 242 and washer 244 are used to releasably secure the liners 238, 240 and inserts 291, 293 to the support member 230. More specifically, the thread collar 242 includes internal threads that are selectively engagable with the external threads located on the support member 230 to releasably secure the liners 238, 240 and inserts 291, 293 to the support member. As a result, the inserts 291, 293, liners 238, 240, collar 242 and washer 244 can be removed and individually cleaned.

Each of the liners 238, 240 is suitably constructed of an elastic material to allow the liners to expand or stretch upon the application of pressure thereto, and then return to a less expanded or undeformed condition upon the removal of such pressure. For example, one suitable material from which the liners 238, 240 can be constructed is silicone. It is understood that the liners 238, 240 can be constructed of different materials and remain with the scope of this invention.

With specific reference to FIGS. 25 and 27, the inner liner 238 has a generally U-shaped cross-section defining a first or outer flange portion 250, a second or inner flange portion 256 generally opposed to and spaced from the outer flange portion, and a tapered web portion 252 extending inward from and interconnecting the inner and outer flange portions. The inner liner 238 further defines a generally elliptical central opening 254, e.g., as defined by the tapered web portion 252 of the inner liner 238. As illustrated in FIG. 25, the inner liner 238 and the outer insert 291 cooperatively define a first pressure chamber 260 of the cup assembly 218. At least one port 295 is formed in the outer insert for providing pneumatic communication between the first pressure chamber 260 and one of the ports 249a in the lid.

With reference again to FIGS. 25 and 27, the outer liner 240 is generally funnel shaped having an outer flange portion 262, a tapered central portion 264 extending from the outer flange portion, and longitudinal portion 268 extending longitudinally within the support member 230 from the tapered central portion of the outer liner to a terminal inner end of the outer liner adjacent the inner end of the support member 230. As seen in FIG. 25, the outer liner 240 has a generally elliptical entry opening 266 defined by the outer flange portion 262 and tapered central portion 264, and a longitudinal channel 270 defined by the longitudinal portion 268. The longitudinal channel 270 defines a vacuum channel of the cup assembly 218 and is in pneumatic communication with the primary channel 241 of the coupler 220 and thereby the vacuum chamber 265 defined by the housing 212. The longitudinal channel 270 is also in fluid communication with the container 222. As illustrated in FIG. 25, the outer liner 240 and inner insert 293 at least in part cooperatively define a second pressure chamber 272 of the cup assembly 218. At least one port 297 is formed in the inner insert 293 for providing pneumatic communication between the second pressure chamber 272 and one of the ports 249b formed in the lid 225.

Figure 24A:
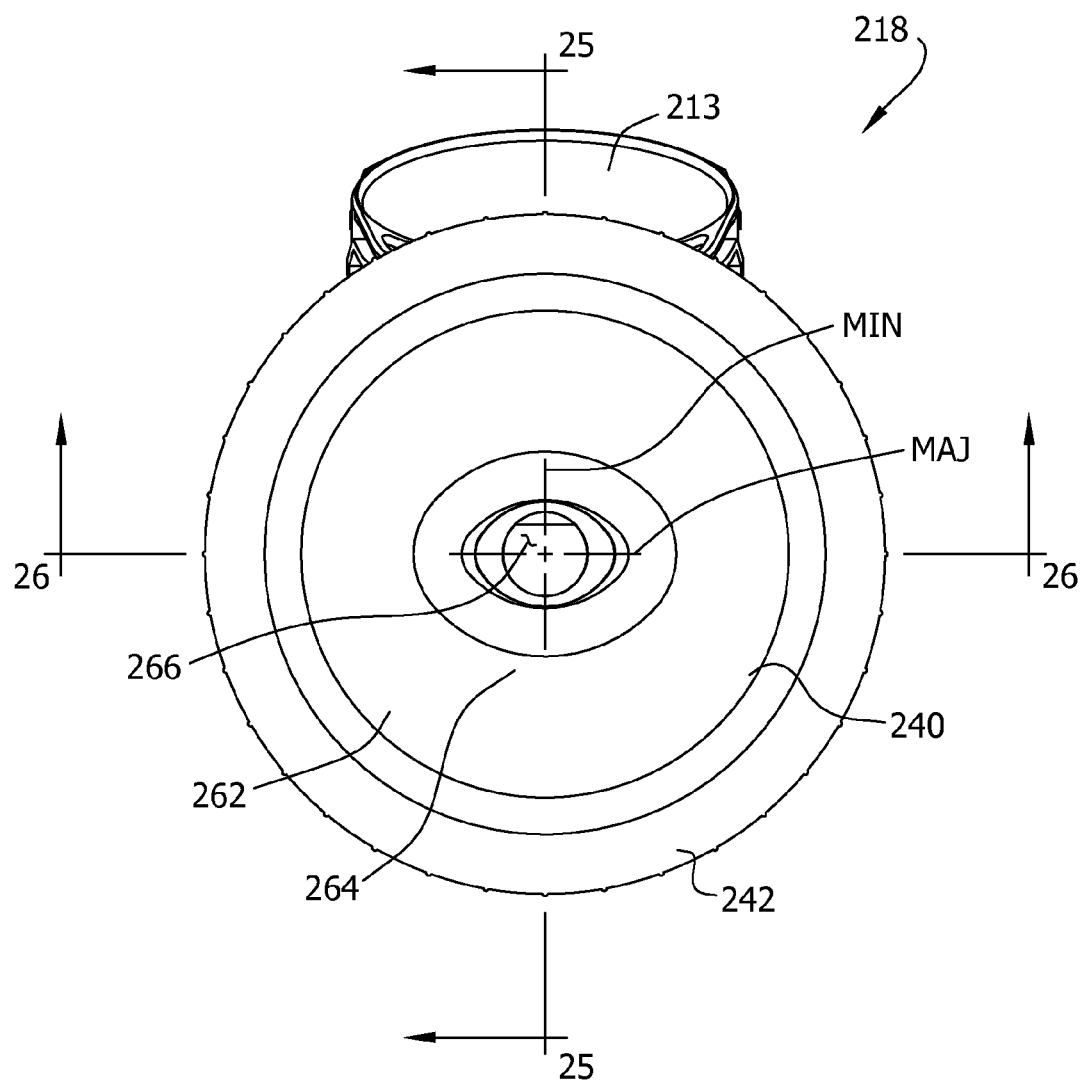
FIG. 24A is a plan view of the cup assembly with inner and outer liners of the cup assembly in an initial, or undeformed configuration.
Figure 24B:
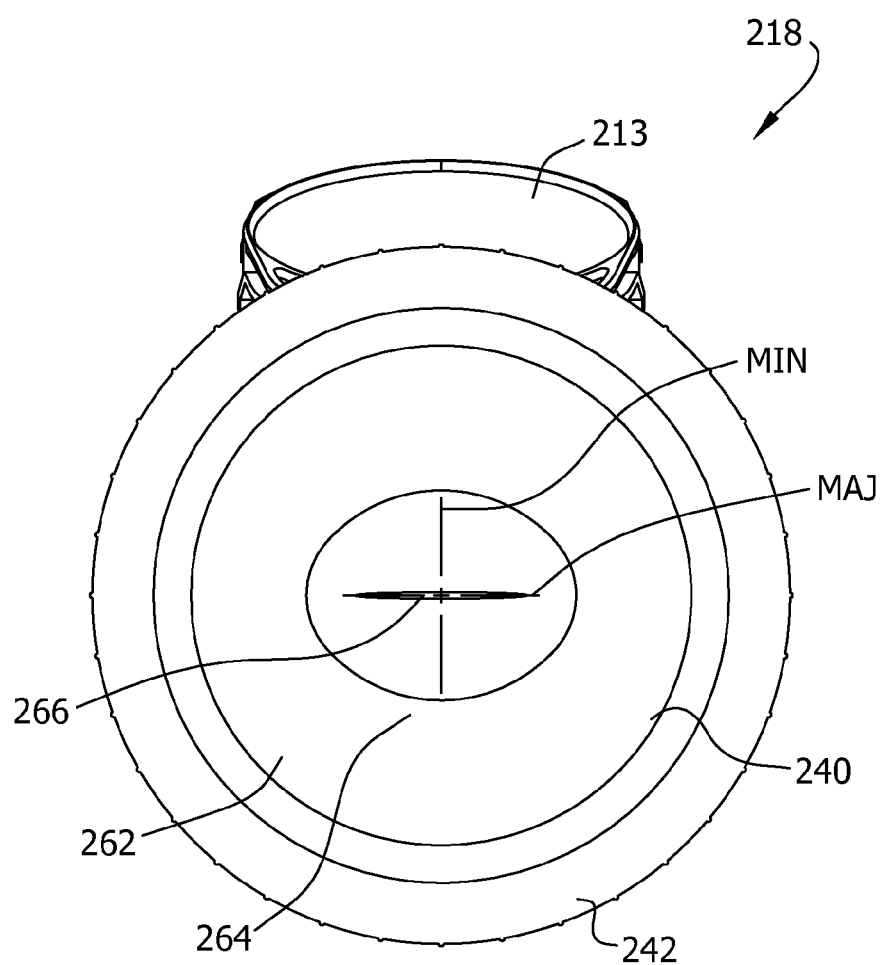
FIG. 24B is a plan view similar to FIG. 24A with the inner and outer liners of the cup assembly hingedly moved to a generally collapsed configuration.

With reference to FIGS. 25 and 26, the elliptical openings 254, 266 in the inner and outer liners 238, 240 are aligned coaxially with each other. As illustrated in FIGS. 24A and 24B, the elliptical opening 266 in the outer liner 240 defines the entry opening into which the mother's breast (e.g., her nipple) is inserted into the cup assembly and has a major axis MAJ and minor axis MIN. In one particularly suitable embodiment, the thickness of at least one of and more suitably each of the inner and outer liners 238, 240 is thickened at the ends of the minor axis MIN of the elliptical openings 254, 266. For example, the inner and outer liners 238, 240 may have a first combined thickness T1' when viewed in cross-section along a line that includes the minor axes MIN of the openings 254, 266 (FIG. 25), and a second combined thickness T2' when viewed in cross-section along a line that includes the major axes MAJ of the openings (FIG. 26). The first combined thickness T1' is significantly greater than the second combined thickness T2'. In one suitable embodiment, the thickness of the inner and outer liners 238, 240 generally at the ends of the major axis MAJ of the respective openings 254, 266 is approximately 0.030 inches while the thickness of the respective inner and outer liners about the remainder of the opening is approximately 0.075.

This thickness differential (i.e., thickening of the inner and/or outer liners 238, 240 generally at the ends of the minor axes MIN of openings 254, 266) creates a living hinge to facilitate a hinged movement of the liners generally about the major axis MAJ of the opening 266 between the fully opened configuration illustrated in FIG. 24A and a collapsed configuration (illustrated in FIG. 24B without a mother's breast therein) in response to pressure applied to the liners (e.g., vacuum pressure in the central passage of the outer liner and/or positive pressure applied to the first and second pressure chambers). This hinged movement more accurately simulates the oral movements applied by a suckling infant to the mother's breast. It is understood that the hinged movement of the inner and outer liners 238, 240 may be created or facilitated in a manner other than by or in addition to varying the thickness of the liners.

Figure 28:
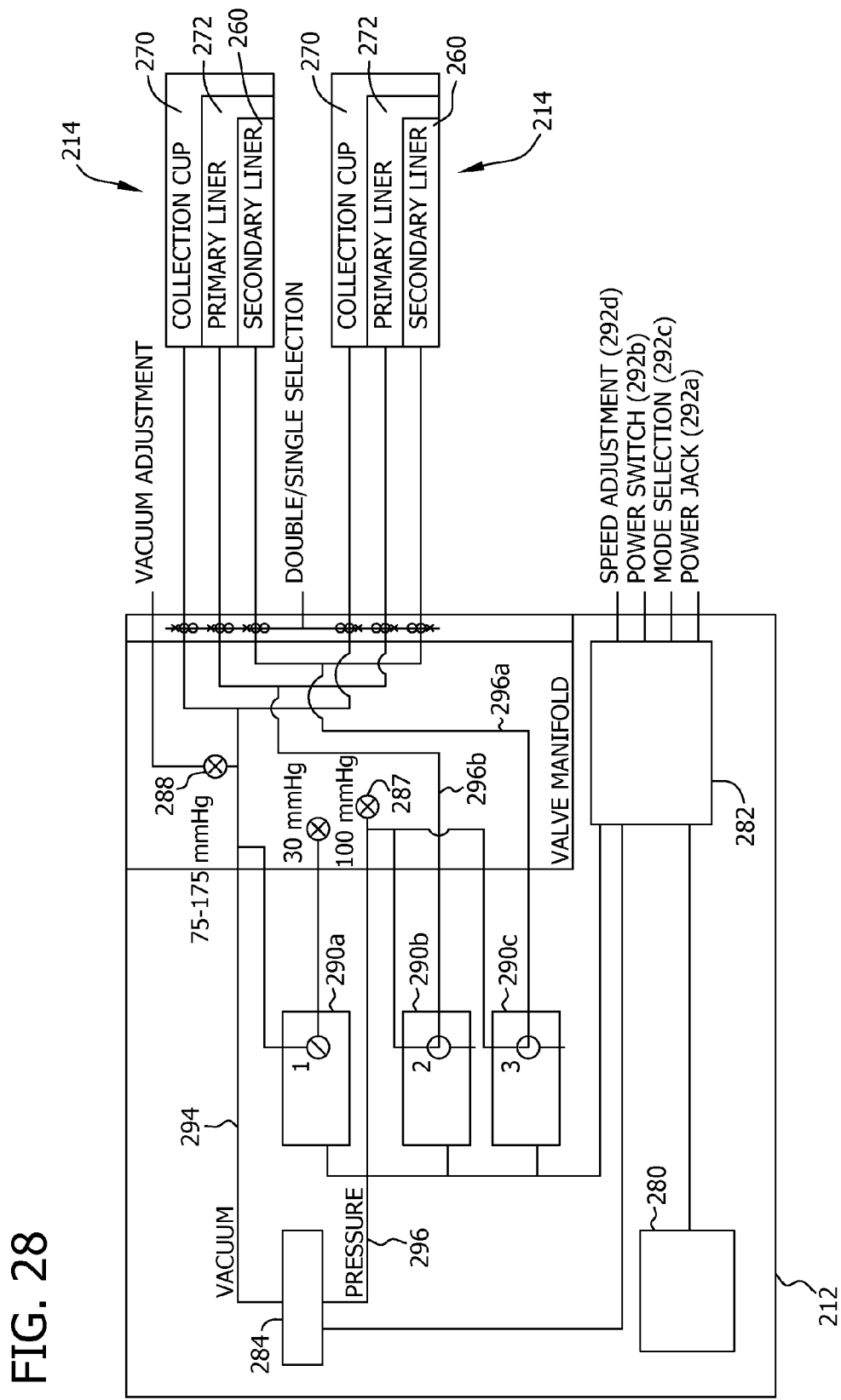
FIG. 28 is a schematic illustrating the interconnection of the various components of the of the electric breast pump.

With reference now to FIG. 28, the breast pump 200 also comprises a power supply 280, a controller 282, and a vacuum/positive pressure pump 284. A regulator valve 288 (e.g., otherwise referred to as a relief valve may be suitably constructed in the manner of a screw-type adjustable valve) is in pneumatic communication with the pump 284 for adjusting the maximum operating (suction) vacuum pressure that can be applied by the vacuum pump to the mother's breast. Solenoid valves 290a-290c (e.g., three being illustrated in FIG. 28) are provided to regulate the timing of positive pressure and vacuum pressure applied to the cup assemblies 218 by the pump 284. In one suitable embodiment, the power supply 280, the controller 282, the pump 284, the regulator valve 288, and the solenoid valves 290a-290c are disposed in the housing 212.

In one embodiment, the power supply 280 is sufficiently sized to provide power to operate the pump 200 including the controller 282, the pump 284, and the solenoid valves 290a-290c for an entire day. For example, the power supply 280 can be sufficiently sized to operate the pump 10 to 12 times for 15 to 20 minutes per time over a 24 hour period. In one suitable embodiment, the power supply 280 will be a rechargeable battery that can be quickly recharged. In one example, the power supply 280 can be recharged in about 3.5 hours using a suitable external source (e.g., a standard 110 volt outlet). Suitably, the power supply 280 can be charged during use. That is, any residual power from the external source not being used to operate the pump will go to recharging the power source 280. The power supply 280 can be connected to the suitable external recharging source using a power jack 292a. In addition, the pump 200 can be operated from power supplied by the external source via the power jack 292a. An LED can be located on the housing 212 for indicating to the user the status of the battery. In one example, the LED being solid green indicates that the battery is charged, solid yellow indicates that the battery is charging, and blinking yellow indicates that the battery needs to be charged.

In one suitable embodiment, the controller 282 is a programmable logic controller (PLC) that is specifically programmed to turn on and off pump 284 and to individually open and close each of the solenoid valves 290a-290c. The controller 282 includes an on/off switch 292b for allowing the nursing mother to selectively turn the breast pump 200 on and off. In one embodiment, the on/off switch comprises a push button. In one suitable embodiment, the push button is pressed for at least 50 milliseconds to turn the pump 200 on, and for at least 500 milliseconds to turn the pump off. That is, the push button has to be pressed considerably longer to turn the pump 200 off than it does to turn the pump on. The controller 282 also includes a mode selection switch 292c for switching the pump 200 from a stimulating mode to an expressing mode, which are described in more detail below, and a speed adjustment 292d for adjusting the cycle rate at which the pump is operated. LEDs can be used to indicate to the user of the pump 200 which mode the pump is operating. In one embodiment, one LED can be provided to indicate that the pump is operating in its stimulating mode and another LED can be provided to indicate that the pump is operating in its expressing mode.

The conduit 216, as illustrated in FIG. 20, comprises a vacuum conduit 294 pneumatically connecting the pump 284 via the regulator valve 288 and solenoid valve 290a to each of the collection assemblies 214 and in particular to the central passages 270 of the cup assemblies 218 (e.g., the central passage of the outer liner 240). One of the solenoid valves, e.g., valve 290a is disposed along the vacuum conduit 294 to regulate the level of vacuum pressure applied by the pump 284 to the mother's breast within the central passage 270. That is, the solenoid valve 290a is controlled by the controller 282 and can be programmed to be closed or opened for a specified period of time. In its opened position, the solenoid valve 290a vents the vacuum conduit to atmosphere to reduce or eliminate the vacuum pressure generated by the pump 284, thus allowing control over the level of vacuum pressure applied to the mother's breast via each of the cup assemblies 218. Thus, the solenoid valve 290a can be used to apply a predetermined vacuum pressure level to the central passages 270 within a range achievable by the pump 284. In one suitable embodiment, the pump 284 is capable of applying a maximum vacuum of up to 150 millimeters of mercury (mm Hg) to the central passages 270 of each of the cup assemblies 218. More suitably, in operation of the pump 284, the regulator valve 288, and the solenoid valve 290a are operated to regulate vacuum pressure in the central passages 270 of the cup assemblies 218 (e.g., the vacuum pressure experienced by the mother's breast) in the range of about 70 mm Hg to about 130 mm Hg, more suitably in the range of about 75 mm Hg to about 125 mm Hg. It is understood, however, that the pump 284 can apply vacuum pressure other than within the above ranges without departing from the scope of this invention. It is important that the maximum pressure within the central passage 270 of each of the cup assemblies 218 be maintained below a level that would result in discomfort and/or tissue damage to the mother's breasts. The maximum pressure within the central passage 270 of each of the cup assemblies 218, however, should be sufficient to draw milk expressed from the mother breasts from the cup assemblies into the container 222.

One or more pressure conduits 296 (e.g., conduits 296a, 296b) pneumatically connect the pump 284 to each of the collection assemblies 214 and more particularly to the first (via conduit 296a) and second (via conduit 296b) pressure chambers 260, 272 of the cup assemblies 218 (FIG. 28). Thus, the pump 284 can be used to independently pressurize the first interior chamber 260 and the second interior chamber 272 of each cup assembly 218 to selectively and independently expand the respective inner and outer liners 238, 240. In one suitable embodiment, the pump 284 is capable of pressurizing each of the first and second pressure chambers 260, 272 up to a maximum pressure established by the relief valve 287. In one suitable embodiment, the maximum pressure established by the relief valve 287 is about 100 mm Hg. It is understood, however, that the pump 284 can pressurize the first and second interior chambers 260, 272 of the cup assemblies 218 between different ranges of positive pressure that those provided herein without departing from the scope of this invention.

One of the solenoid valves 290c is disposed along the first conduit 296a for selectively regulating the pressurization of the first pressure chamber 260, and another solenoid valve 290b is disposed along the second conduit 296b for selectively regulating the pressurization of the second pressure chamber 272. As mentioned above, the solenoid valves 290b, 290c are controlled by the controller 282 and can be programmed to be closed or opened for a specified period of time. Thus, the solenoid valves 290b, 290c along the first and second conduits 296a, 296b can be used in their opened positions to selectively pressurize the first and second interior chambers 260, 272 at any positive pressure within the limits of the pump 284 for a predetermined period of time. The solenoid valves 290b, 290c, which are three way valves, also facilitate independent venting or depressurization of the respective pressure chambers 260, 272. The solenoids valves 290b, 290c when moved to their closed position allow for selectively venting (in whole or in part) the first pressure chamber 260 and second interior chamber 272, respectively. Thus, the solenoid valve 290b, 290c along the first and second conduits 296a, 296b can be opened to selectively pressurize the first and second interior chambers 260, 272 and can be closed to selectively depressurize the first and second pressure chambers 260, 272 for predetermined periods of time.

In the illustrated schematic, the cup assemblies 218 are operated simultaneously using the same solenoid valves 290a-290c. It is understood, however, that each of the cup assemblies 218 may be controlled independently of each other. That is, each of the cup assemblies 218 may be provided independent sets of solenoid valves with each respective set of solenoid valves controlled independently by the controller 282. It is also understood that the collection assemblies 214 and specifically the cup assemblies 218 described herein may be configured for use with a manual pump.

Operation of the breast pump 200 will now be described with reference to a single one of the collection assemblies 214, it being understood that operation of the other collection assembly is substantially the same as that described herein. In operation, the nursing mother brings the cup assembly 218 of the collection assembly 214 and in particular the outer liner 240 into contact with one of her breasts, with her nipple generally received through the elliptical opening 266 into the central passage 270 of the cup assembly. In this position, the flange portion 262 and tapered portion 264 of the outer liner 240 lay against the mother's breast surrounding the nipple. The breast pump 200 is activated by moving the on/off switch 292 of the controller 282 to its on position, thereby initiating the stimulating mode of pumping cycle of the breast pump. The stimulating mode is designed to mimic an infant's initial suckling (e.g., non-nutritive suckling), which causes the mother to experience "let down." "Let down" occurs when milk within the mother's breast flows toward her nipple.

In the stimulating mode, the pump 284 is operated to apply a suction (e.g., maximum) vacuum pressure to the mother's breast within the central passage 270 of the outer liner 240. For example, a maximum vacuum pressure in the range of about 30 mm Hg to about 150 mm Hg, more suitably in the range of about 75 mm Hg to about 125 mm Hg is applied to the breast within the central passage 270 of the outer liner 240. In one particularly suitable embodiment, the suction vacuum pressure is applied to the mother's breast continuously throughout the cycle. It is understood, however, that the suction vacuum pressure can be selectively varied through the cycle.

The pump 284 is also operated to pressurize the first pressure chamber 260 (e.g., as defined by the inner liner 238) of the cup assembly 218 to apply a compressive pressure against the mother's breast at a location relatively distal from the end of the mother's nipple. For example, in one suitable embodiment, the first pressure chamber 260 is pressurized to a pressure of about 70 mm Hg to about 100 mm Hg, and more suitably about 85 mm Hg. This is done by the controller 282 moving the solenoid valve 290c disposed along the first conduit 296a of the pressure conduit 296 to its opened position to pressurize the first pressure chamber 260. Pressurizing the first pressure chamber 260 in this manner causes the expansion of the inner liner 238 (and hence the outer liner 240 in the region of the inner liner) away from the support member 230 to apply pressure to the mother's breast within the central passage 270 of the outer liner 240. In one suitable embodiment, the first pressure chamber 260 is pressurized continuously for approximately the first fifteen cycles of the stimulating mode and depressurized continuously for approximately the next ten cycles (i.e., cycles sixteen through twenty-five). The first pressure chamber 260 is pressurized and depressurized in this pattern continuously through the stimulating mode.

The second pressure chamber 272 (e.g., defined by the outer liner 240) is pressurized to apply a compressive pressure against the mother's breast at a location nearer to and in some embodiments adjacent the end of the mother's nipple. For example, in one suitable embodiment, the second pressure chamber 272 is pressurized to a pressure of about 70 mm Hg to about 100 mm Hg, and more suitably about 85 mm Hg. In particular, the controller 282 moves the solenoid valve 290b disposed along the second conduit 296b of the pressure conduit 296 to pressurize the second pressure chamber 272 to the desired pressure. This causes the outer liner 270 to expand inward away from the support member 230 thereby reducing the height of the central passage 270 to apply pressure to the mother's breast. In one embodiment, the pressure in the second pressure chamber 272 is suitably the same as the pressure in the first pressure chamber 260. It is understood, however, that the pressure in the second pressure chamber 272 may be greater than or less than that in the first pressure chamber 260 without departing from the scope of this invention.

In one suitable embodiment, the second pressure chamber 272 is pressurized in the range of about 30 to about 60 percent of each cycle, and more suitably about 50 percent of each cycle. In one particularly suitable embodiment, pressurization of the second pressure chamber 272 is delayed following the start of each cycle and discontinued before the end of each cycle. As such, the second pressure chamber 272 quickly pressurizes and depressurizes to simulate the quick, shallow sucks of a baby during the onset of feeding (i.e., non-nutritive suckling). As mentioned above, non-nutritive suckling of a baby causes the milk in the nursing mother's breast ducts to flow toward her nipple, where it can be expressed.

In the stimulating mode, the pumping cycle is repeated as often as necessary to cause the mother to experience let down. In one suitable embodiment, the pumping cycle of the breast pump 200 is moved automatically from the stimulating mode to the expressing mode after about 90 seconds. The mother can manually move the pumping cycle from the stimulating mode to the expressing mode using the mode selector switch. The corresponding LED located on the housing 212 is illuminated to inform the mother which mode the pumping cycle is currently in.

In one suitable embodiment, the breast pump is operable in the range of about 90-120 cycles per minute during the stimulating mode. One example of a suitable stimulating mode is summarized in the following table.

| Cycles 1-15 of the Stimulating mode Time (seconds) | Positive Pressure in the first interior chamber (mm Hg) | Positive Pressure in the second interior chamber (mm Hg) | Vacuum applied to the Central Passage (mm Hg) |
|---|---|---|---|
| 0 | 70-100 | 0 | 70-175 |
| 0.1 | 70-100 | 70-100 | 70-175 |
| 0.25 | 70-100 | 70-100 | 70-175 |
| 0.35 | 70-100 | 70-100 | 70-175 |
| 0.5 | 70-100 | 0 | 70-175 |

| Cycles 16-25 of the Stimulating mode Time (seconds) | Positive Pressure in the first interior chamber (mm Hg) | Positive Pressure in the second interior chamber (mm Hg) | Vacuum applied to the Central Passage (mm Hg) |
|---|---|---|---|
| 0 | 0 | 0 | 70-175 |
| 0.1 | 0 | 70-100 | 70-175 |
| 0.25 | 0 | 70-100 | 70-175 |
| 0.35 | 0 | 70-100 | 70-175 |
| 0.5 | 0 | 0 | 70-175 |

The expressing mode of the pumping cycle is suitably designed to simulate the suckling action and frequency of a nursing infant, e.g., the peristaltic movement of the infant's tongue and palate used to express milk. In particular, during each cycle the pump 284 is operated to apply a suction (e.g., maximum) vacuum pressure to the mother's breast within the central passage 270 of each of the cup assemblies 214. For example, a vacuum pressure in the range of about 70 mm Hg to about 150 mm Hg and more suitably in the range of about 75 mm Hg to about 125 mm Hg is applied to each of the breasts within the respective central passages 270. More specifically, the controller 282 moves the solenoid valve 290a to its opened position to thereby allow the desired maximum vacuum pressure (as limited by the regulator valve 288) to be applied to mother's breast. The vacuum pressure facilitates the collection of milk expressed from the mother's breasts and aids in maintaining the cup assemblies 218 on the mother's breasts. In one particularly suitable embodiment, the suction vacuum pressure is applied to the mother's breast in the range of about 50 to about 80 percent of each cycle, and more suitably about 70 percent of each cycle.

The pump 284 is also operated to pressurize the first pressure chamber 260 (e.g., as defined at least in part by the inner liner 238) of the cup assembly 218 to apply a compressive pressure against the mother's breasts at a location relatively distal from the end of the mother's nipple. For example, in one suitable embodiment, the first pressure chamber 260 is pressurized to a pressure of about 30 mm Hg to about 100 mm Hg, and more suitably about 85 mm Hg. This is done by the controller 282 opening the solenoid valve 290c disposed along the first conduit 296a of the pressure conduit 296 to pressurize the first pressure chamber 260. Pressurizing the first pressure chamber 260 in this manner causes the expansion of the inner liner 238 (and hence the outer liner 240 in the region of the inner liner) away from the support member 230 to apply pressure to the mother's breast within the central passage 270 of the outer liner 240. In one suitable embodiment, the first pressure chamber 260 is pressurized in the range of about 50 to about 80 percent of each cycle, and more suitably about 70 percent of each cycle.

At least about the same time that the first pressure chamber 260 is pressurized, and more suitably shortly thereafter, the second pressure chamber 272 (e.g., defined at least in part by the outer liner 240) is pressurized to apply a compressive pressure against the mother's breast at a location nearer to and in some embodiments adjacent the end of the mother's nipple. For example, in one suitable embodiment, the second pressure chamber 272 is pressurized to a pressure of about 70 mm Hg to about 100 mm Hg, and more suitably about 85 mm Hg. In particular, the controller 282 opens the solenoid valve 290b disposed along the second conduit 296b of the pressure conduit 296 to pressurize the second pressure chamber 272 to the desired pressure. This causes the outer liner 270 to expand inward away from the support member 230 thereby reducing the height of the central passage 270 to apply pressure to the mother's breast. In one embodiment, the pressure in the second pressure chamber 272 is suitably the same as the pressure in the first pressure chamber 260. It is understood, however, that the pressure in the second pressure chamber 272 may be greater than or less than that in the first pressure chamber 260 without departing from the scope of this invention.

In one suitable embodiment, the second pressure chamber 272 is pressurized in the range of about 30 to about 60 percent of each cycle, and more suitably about 50 percent of each cycle. In one particularly suitable embodiment, pressurization of the second pressure chamber 272 is delayed a suitable period following initial pressurization of the first pressure chamber 260 during each cycle such that the cycle time during which both the first and second pressure chambers are pressurized terminates at the same time during the cycle. As such, the first and second pressure chambers 260, 272 are pressurized sequentially to facilitate the flow of breast milk toward the mother's nipples where it can be expressed. Moreover, the hinged movement of the inner and outer liners 238, 240 in response to the vacuum pressure in the central passage 270 of the outer liner and the pressurization of the first and second pressure chambers 260, 272 more accurately simulates the tongue and palate movement of the suckling infant. Breast milk expressed from the mother's breast flows through the central passage 270 of the outer liner 270 into the secondary channel of the coupler 220, down into and through the primary channel thereof, and into the container 222.

Once both the first and second pressure chambers 260, 272 are fully pressurized during a suction cycle, the vacuum in the central passage 270 of the cup assembly 218 is reduced to about 30 mm Hg by the controller 282 opening solenoid valve 290a to vent the vacuum path. The 30 mm Hg vacuum simulates the latching pressure of a suckling infant and also maintains the cup assembly 218 on the mother's breast.

Finally, both the first and second pressure chambers 260, 272 are vented by opening the corresponding solenoid valves 290b, 290c which cause the chambers to depressurize to atmospheric pressure. Upon depressurization, the inner and outer liners 238, 240 return in large part (with the exception to any small deformation due to the latching pressure) to their initial or undeformed configuration. After the depressurization is complete, the valve 290a is closed so that the central passage 270 and hence the mother's breast therein is subjected to the suction vacuum pressure again for the next cycle.

The pumping cycle is repeated as often as necessary to express as much milk as the mother desires or is able to produce. The pumping cycle of the breast pump 200 is stopped by manually moving the on/off switch 292 of the controller 282 to the off position. In one suitable embodiment, the breast pump is operable in the range of about 50-90 cycles per minute, more suitably about 60-70 cycles per minute, and even more suitably about 60 cycles per minute (about 1 second per cycle). One example of a suitable pump cycle for the expressing mode is summarized in the following table.

green bottle that minimizes the amount air in the bottle and the amount of light that penetrates the bottle).

Figure 30:
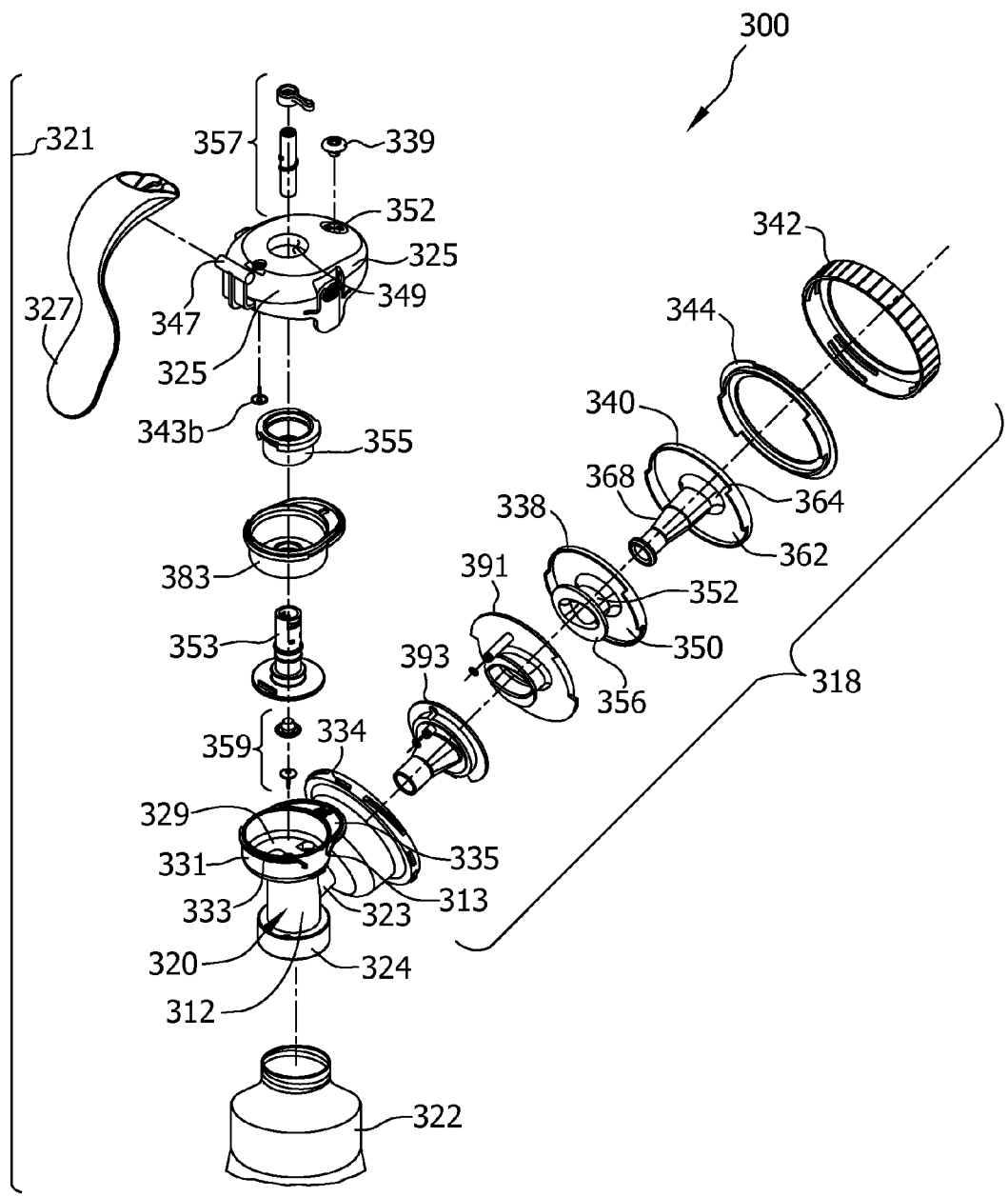
FIG. 30 is an exploded perspective of the manual breast pump with a portion of the container cut away.
Figure 31:
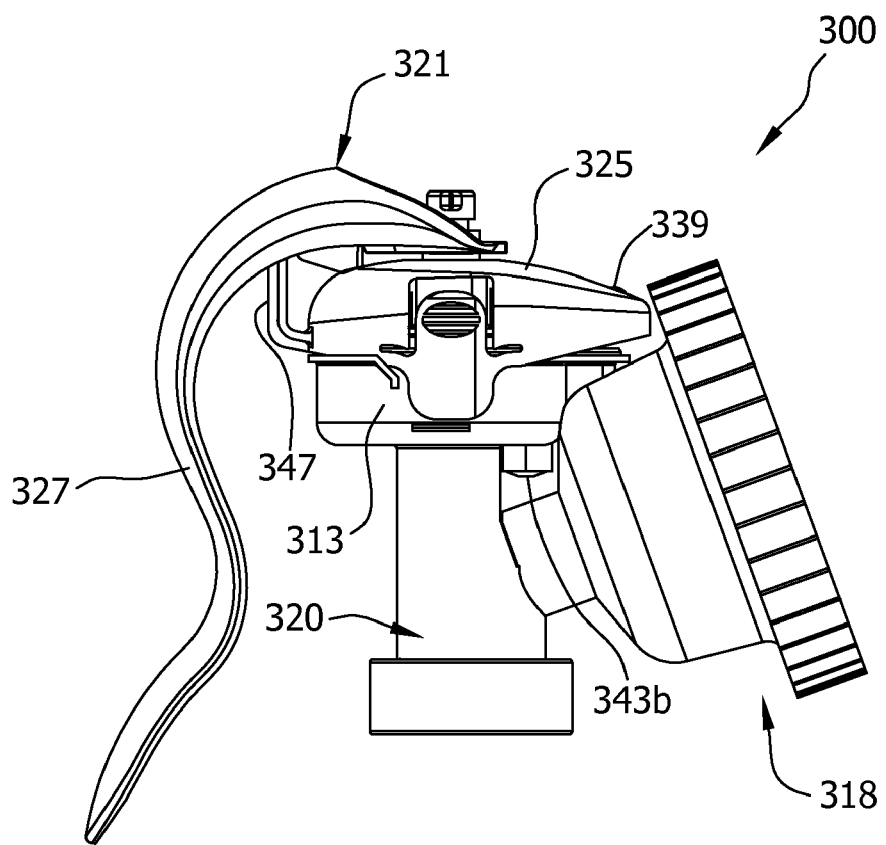
FIG. 31 is a side elevation of the manual breast pump.
Figure 32:
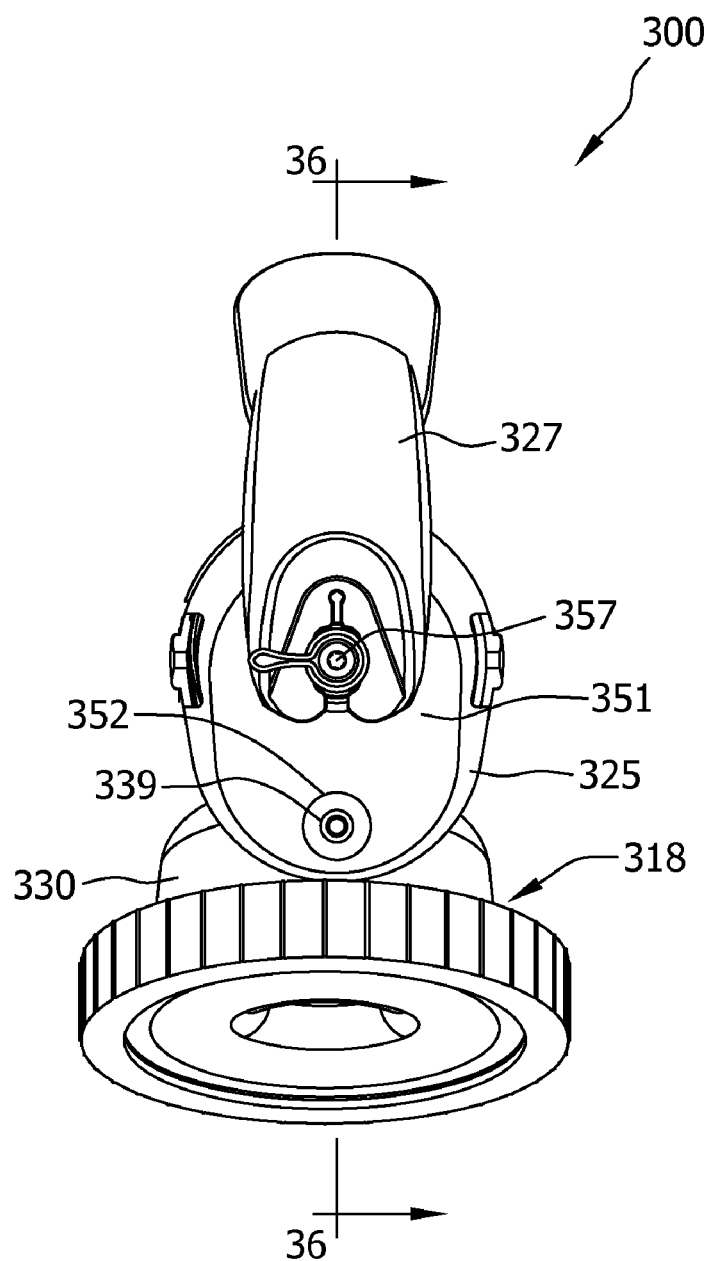
FIG. 32 is a plan view of the manual breast pump.
Figure 33:
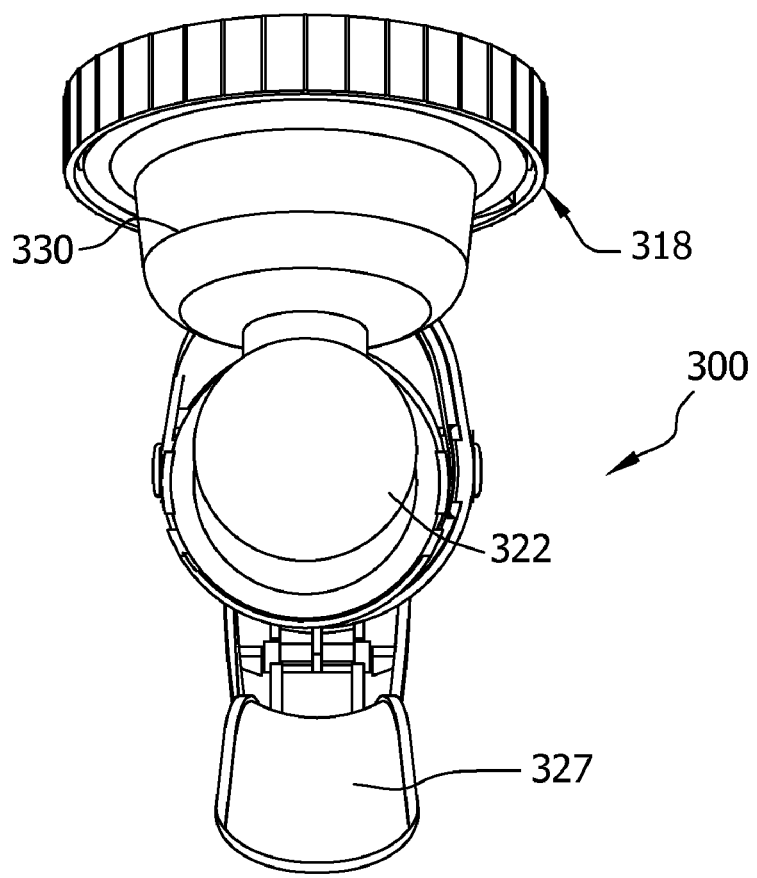
FIG. 33 is a bottom view of the manual breast pump.
Figure 36:
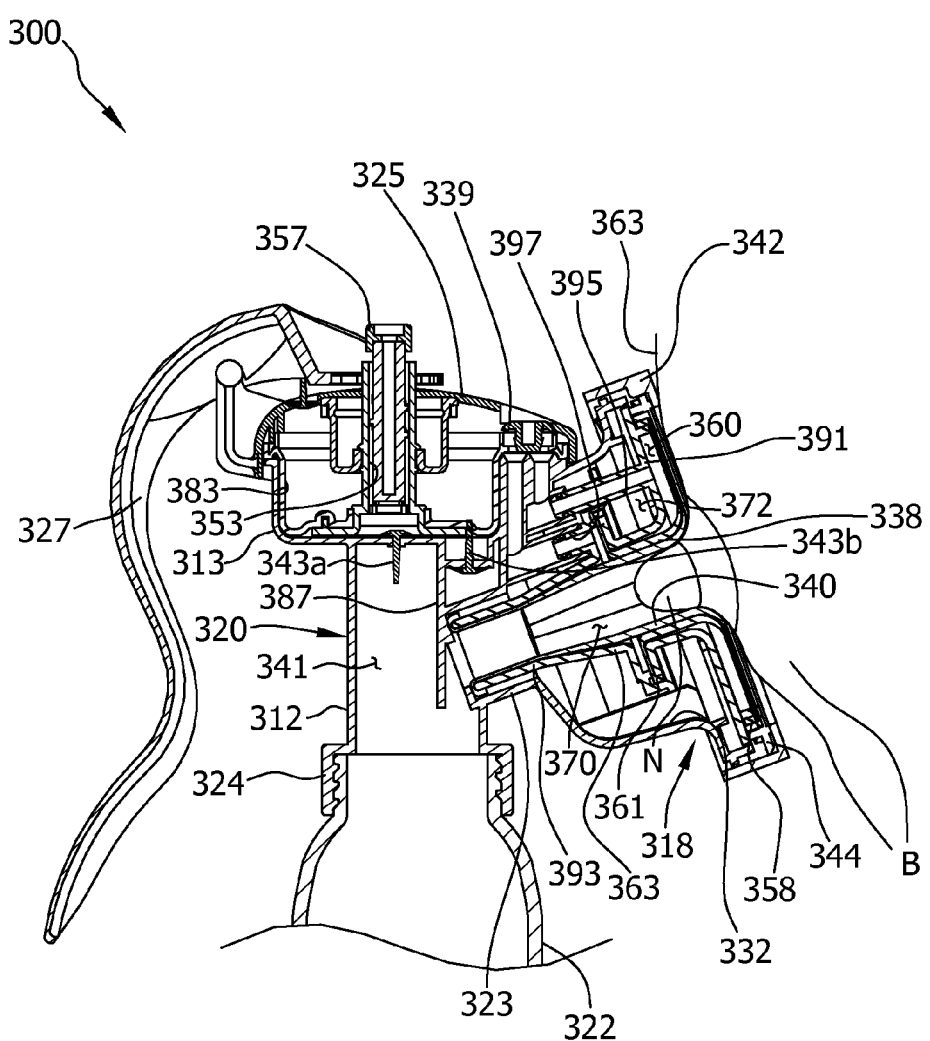
FIG. 36 is a cross-section of the manual breast pump taken along line 36-36 of FIG. 32 with a handle of the pump in a relaxed position.

As illustrated in FIGS. 30 and 36, the coupler 320 has a primary tubular segment 312 defining a primary channel 341 oriented vertically in the drawings (e.g., to simulate the general orientation of the collection assembly in use), and a secondary tubular segment 323 extending outward from the primary segment at an angle relative thereto and defining a secondary channel 363 within the coupler. The coupler 320 includes a threaded lower socket 324, e.g., at the lower end of the primary segment 312, for threaded connection with the container 322 to couple the container to the coupler. The cup assembly 318 is mounted on the coupler 320 at the distal end of the secondary segment 323 to provide pneumatic and fluid communication between the cup assembly and the container 322 via the coupler. It is understood that couplers having other shapes and configurations can be used without departing from the scope of this invention. It is also understood that the coupler 320 may connect to the cup assembly 318, and/or container 322 in any suitable manner, such as, threads, and snap-fits, or other connection.

The coupler 320 also includes a pump housing 313 located above the primary segment 312. The pump housing 313 of the illustrated embodiment is generally cup shaped having a generally flat bottom 329 and a cylindrical wall 331 extending upward from the bottom. A flange 335 extends at least partially around the periphery of the cylindrical wall 331. The bottom 329 of the pump housing 313 includes an aperture 333 in pneumatic communication with the primary channel 341 of

| Expressing Mode Pump Cycle Time (seconds) | Positive Pressure in the first interior chamber (mm Hg) | Positive Pressure in the second interior chamber (mm Hg) | Vacuum applied to the Central Passage (mm Hg) |
| --- | --- | --- | --- |
| 0 | 70-100 | 0 | 70-175 |
| 0.2 | 70-100 | 70-100 | 70-175 |
| 0.5 | 70-100 | 70-100 | 30 |
| 0.7 | 0 | 0 | 70-175 |
| 1 | 70-100 | 0 | 70-175 |

The breast pump 200 described herein has been designed to more closely mimic the suckling of a nursing infant thereby providing a significantly more efficient and comfortable pump to mothers for expressing breast milk. More particularly, the breast pump 200 operates at a relatively low vacuum pressure as compared to conventional breast pumps, has a cup assembly with an elliptical opening (generally mouth shaped) and capable of hinged movement at the opening, sequentially applies compressive pressure to the mother's breast, and operates through a timed cycle that is intended to simulate the peristaltic movement of an infant's tongue and palate.

Figure 29:
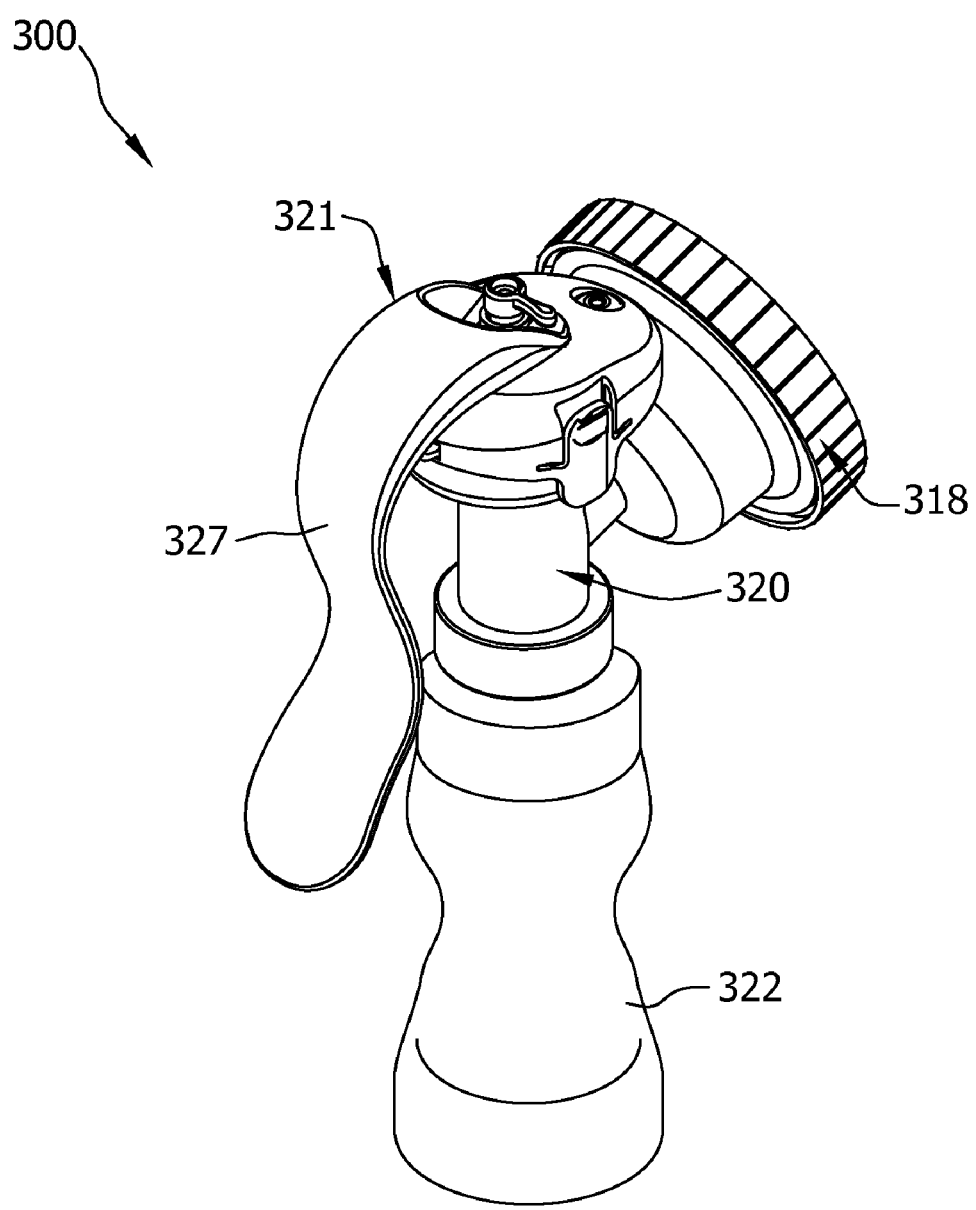
FIG. 29 is a perspective of another embodiment of a manual breast pump having a container attached thereto.

With reference now to FIGS. 29-38, and specifically FIG. 29, a manual breast pump according to another embodiment is indicated generally at 300. The illustrated manual breast pump 300 includes a pump, indicated generally at 321, a cup assembly, indicated generally at 318, a coupler 320, and a container 322 for receiving milk expressed from a nursing mother's breast by the breast pump. In the illustrated embodiment, the cup assembly 318, coupler 320, and container 322 are substantially similar to the cup assembly 218, coupler 220, and container 222 described above with respect to FIGS. 20-28. Thus, the illustrated container 322 is a conventional nursing bottle. It is understood, however, that other types of bottles and containers can be used to collect the expressed breast milk. For example, the container 322 can be a dedicated milk storage bottle (e.g., a relatively small amber or the coupler 320. A check valve 343a is associated with the aperture 333 in the pump housing 313 for allowing air to be drawn from the primary channel 341 of the coupler 341 into the pump housing 313. The check valve 343a, however, inhibits air from flowing in the opposite direction. That is, the check valve 343a inhibits air from flowing from the pump housing 313 into the primary channel 341 of the coupler 341. As a result, a vacuum or negative pressure can readily be applied to the primary channel 341 of the coupler 341 while pressurization of the primary channel of the coupler is inhibited. It is contemplated that in some embodiments the check valve 343a associated with the aperture 333 in the pump housing 313 can be omitted. A relief valve 343b is associated with another aperture in the housing 313 for allowing air to be drawn into the housing from the atmosphere should the vacuum within the housing exceed a predetermined threshold.

A lid or cap 325 is mounted (e.g., by suitable threading, by snap fit, or other suitable mounting arrangement) on the coupler 320 at its top to sealingly close the coupler. More specifically, the lid 325 is mounted by snap fit on the pump housing 313 of the coupler 320. With reference again to FIG. 30, the lid 325 has a mount 347 for pivotally mounting a handle 327 of the pump 321 thereon. The lid 325 also includes a central opening 349 and a vent passage 352. A pressure relief valve 339 is operatively mounted onto the lid 325 and pneumatically connected to the vent passageway 352. The valve 339 allows the pump housing 313 to vent during operation of the pump 321. With reference now to FIG. 36, a check valve 343 is associated with an aperture in the pump housing 113 for inhibiting pressurization of the pump housing.

Figure 38:
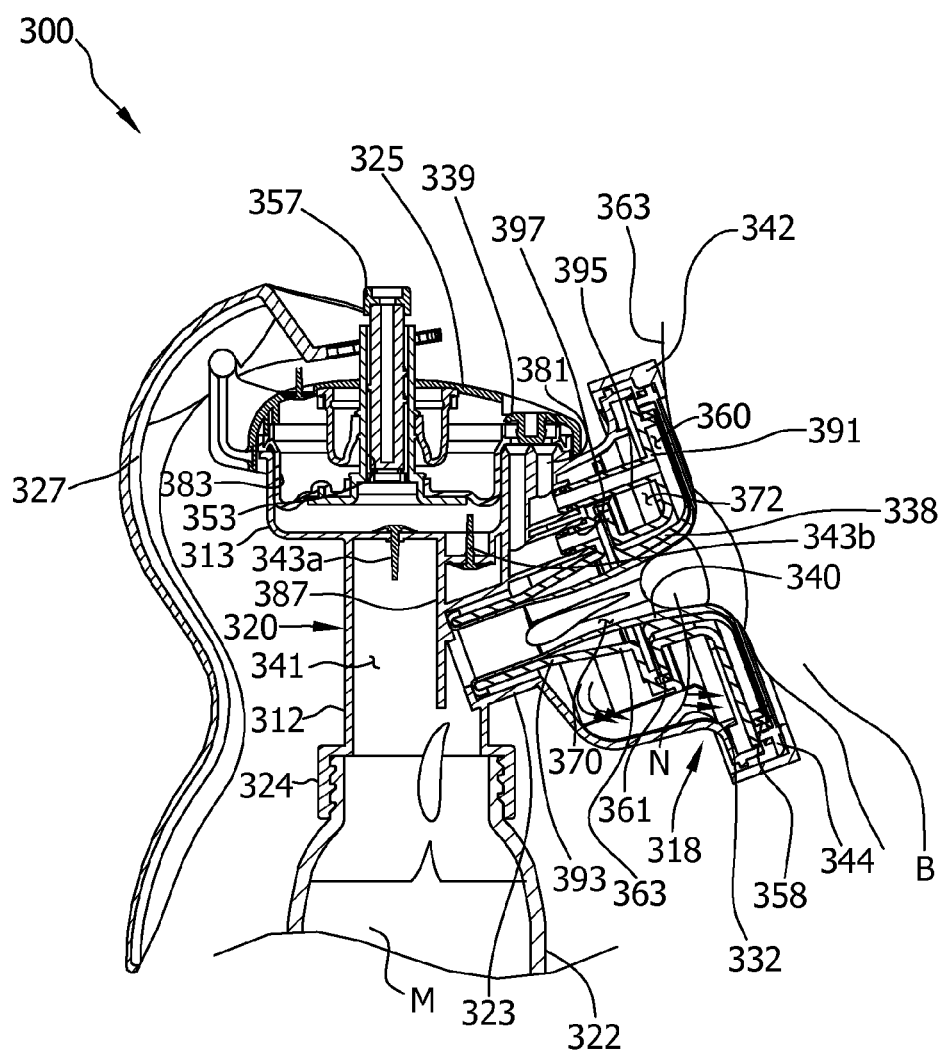
FIG. 38 is a cross-section similar to FIGS. 36 and 37 but with the pump handle in a fully compressed position.

With reference still to FIG. 36, the handle 327 of the illustrated embodiment of the pump 321 is generally S-shaped and is pivotally mounted on the mount 347 of the lid 325 via a snap-connection therewith. The handle 327 can be manually squeezed and released to operate the pump 321. Thus, the handle 327 can be selectively moved between a relaxed position (FIG. 36) and a compressed position (FIG. 38). It is understood that the handle can have other shapes and configurations.

Figure 37:
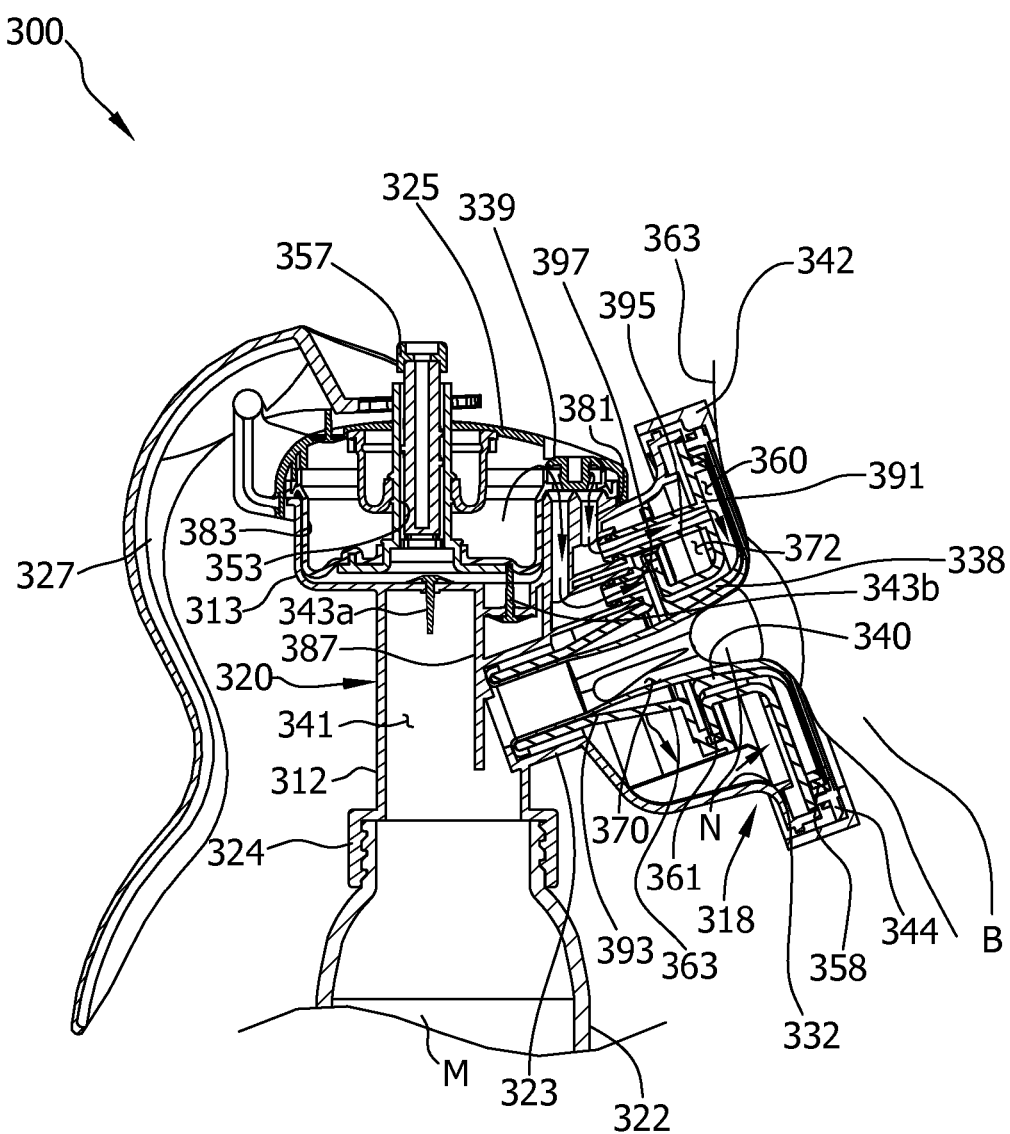
FIG. 37 is a cross-section similar to FIG. 36 but with the pump handle in a partially compressed position.

The handle is operatively connected to a lift assembly of the pump 231. The lift assembly comprises a stem 353, a bellows 355, an actuator 357, and an umbrella valve 359 and is received through the central opening 349 in the lid 325. The stem 353, as illustrated in FIGS. 36-38, includes a tubular wall extending between opened upper and lower ends. The lower end includes an annular flange extending outward from the tubular wall. A pair of spaced apart ribs is disposed on an exterior surface of the tubular wall. The bellows 355 is a flexible membrane that is disposed within the pump housing 313 and affixed at one of its ends to the lid 325 adjacent the central opening 349 therein. The opposite end of the bellows 355 is affixed to the stem 353 between the pair of ribs. The actuator 357 of the lift assembly extends through the stem 353 and is operatively connected to the umbrella valve 359, which is disposed within the tubular stem. The stem 353 is operatively connected to the handle 327 so that movement of the handle between its relaxed and compressed positions results in corresponding movement of the lift assembly.

As seen in FIGS. 36-38, a diaphragm 383 is received in the pump housing 313 and comprises a flexible membrane. One end of the diaphragm 383 is captured between the lid 325 and the pump housing 313 and is affixed at its opposite end to the flange of the stem 353. As best illustrated in FIG. 38, the diaphragm 383 and the pump housing 313 collectively define a vacuum chamber 365 for inducing a vacuum in the primary channel 341 of the coupler 320. The diaphragm 383, the lid 325, and the bellows 355 collectively define a pressure chamber 367 for pressurizing the cup assembly 318 as will be described in more detail below.

With reference to FIGS. 31-35, the cup assembly 318 is sized and shaped for receiving and forming a seal with one of the nursing mother's breasts, particularly at one of the mother's nipples. Specifically, the cup assembly 318 comprises a generally tubular, and more particularly a generally funnel-shaped, support member 330 having an interior or central passage 332 extending longitudinally therethrough (FIG. 36). As seen in FIG. 30, the support member 330 has a flanged longitudinally outer end 334 with external threads. In this embodiment, the support member 330 of the cup assembly 318 is formed as a single-piece with the coupler 320 and the pump housing 313. The unitary coupler 320, pump housing 313, and support member 330 may be constructed of any suitable material but in a particularly suitable embodiment is sufficiently resistant to deformation in response to positive or negative pressure applied thereto at the operating pressures of the pump. For example, the unitary coupler 320, pump housing 313, and support member 330 may be suitably constructed of a generally rigid plastic. It is understood that the coupler 320, pump housing 313, and support member 330 can be formed separately and attached together in any suitable manner.

With reference to FIG. 30, the cup assembly 318 further comprises a pair of expandable liners, referred to herein as inner liner 338 and outer liner 340. A pair of mounting inserts (e.g., an outer insert 391 and an inner insert 393) mounts the inner and outer liners 338, 340 on the support member 330 of the cup assembly 318. A thread collar 342 and washer 344 are used to releasably secure the liners 338, 340 and inserts 391, 393 to the support member 330. More specifically, the thread collar 342 includes internal threads that are selectively engagable with the external threads located on the support member 330 to releasably secure the liners 338, 340 and inserts 391, 393 to the support member. As a result, the inserts 391, 393, liners 338, 340, collar 342 and washer 344 can be removed and individually cleaned.

Each of the liners 338, 340 is suitably constructed of an elastic material to allow the liners to expand or stretch upon the application of pressure thereto, and then return to a less expanded or undeformed condition upon the removal of such pressure. For example, one suitable material from which the liners 338, 340 can be constructed is silicone. It is understood that the liners 338, 340 can be constructed of different materials and remain with the scope of this invention.

With specific reference to FIGS. 30 and 36, the inner liner 338 has a generally U-shaped cross-section defining a first or outer flange portion 350, a second or inner flange portion 356 generally opposed to and spaced from the outer flange portion, and a tapered web portion 352 extending inward from and interconnecting the inner and outer flange portions. The inner liner 338 further defines a generally elliptical central opening (not shown), e.g., as defined by the tapered web portion 352 of the inner liner 338. As illustrated in FIG. 36, the inner liner 338 and the outer insert 391 cooperatively define a first pressure chamber 360 of the cup assembly 318. At least one port 395 is formed in the outer insert for providing pneumatic communication between the first pressure chamber 360 and the pressure chamber 367 within the pump housing 316.

Figure 34:
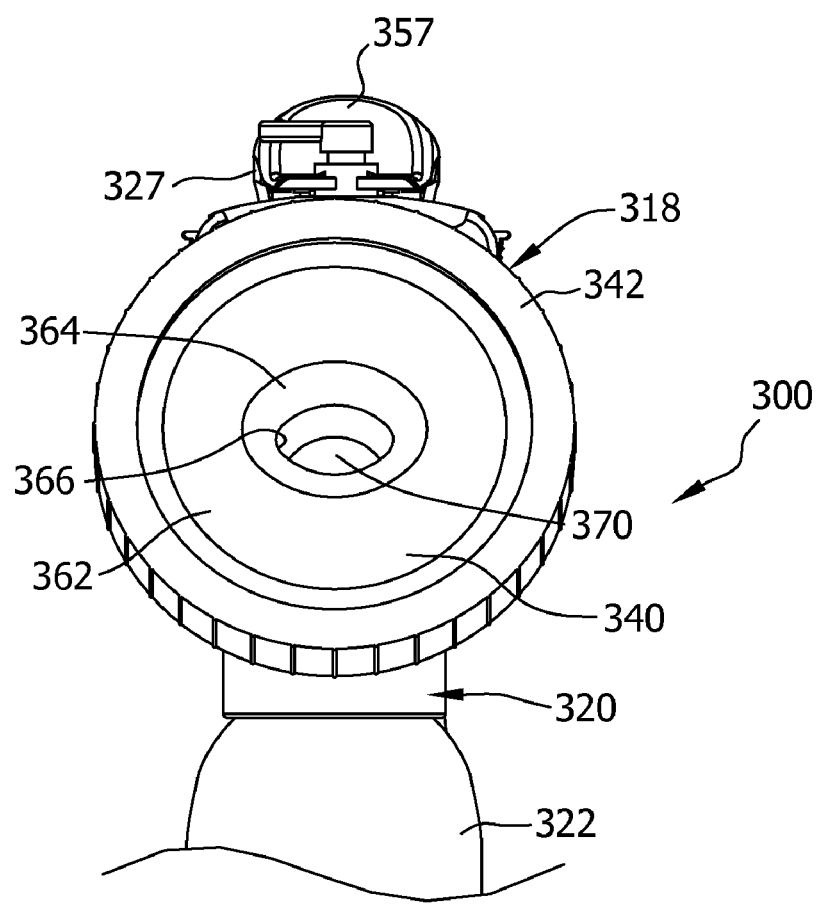
FIG. 34 is a front view of the manual breast pump.
Figure 35:
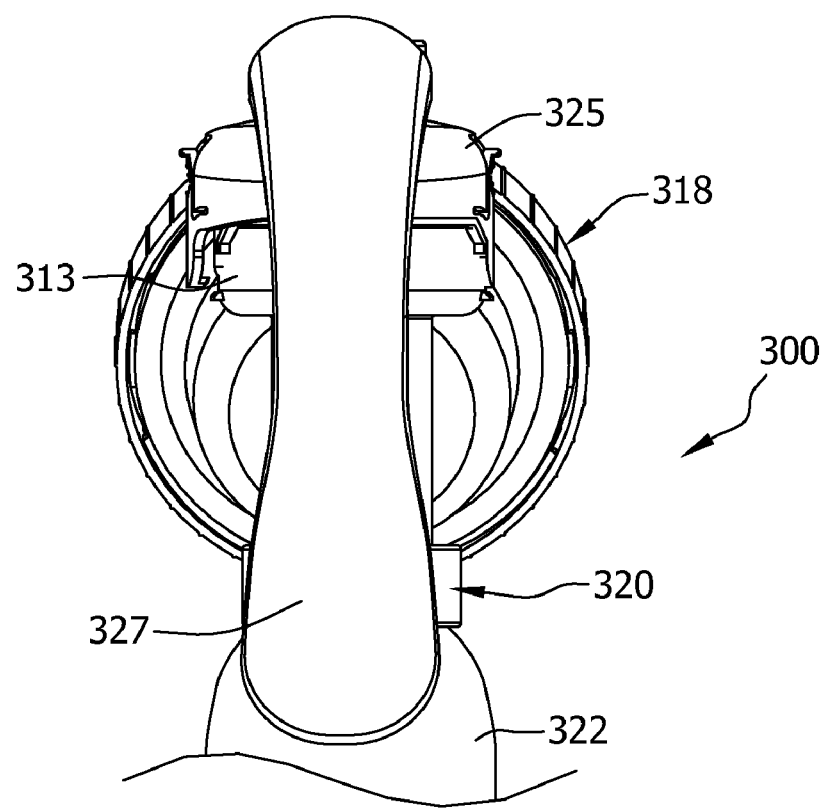
FIG. 35 is a back view of the manual breast pump.

With reference again to FIG. 30, the outer liner 340 is generally funnel shaped having an outer flange portion 362, a tapered central portion 364 extending from the outer flange portion, and longitudinal portion 368 extending longitudinally within the support member 330 from the tapered central portion of the outer liner to a terminal inner end of the outer liner adjacent the inner end of the support member 330. As seen in FIG. 34, the outer liner 340 has a generally elliptical entry opening 366 defined by the outer flange portion 362 and tapered central portion 364, and a longitudinal channel 370 defined by the longitudinal portion 368. With reference now to FIG. 36, the longitudinal channel 370 defines a vacuum channel of the cup assembly 318 and is in pneumatic communication with the primary channel 341 of the coupler 320 and thereby the vacuum chamber 365 of the pump 321. The longitudinal channel 370 is also in fluid communication with the container 322. As illustrated in FIG. 36, the outer liner 340 and inner insert 393 at least in part cooperatively define a second pressure chamber 372 of the cup assembly 318. At least one port 397 is formed in the inner insert 393 for providing pneumatic communication between the second pressure chamber 372 and the pressure chamber 367 within the pump housing 316.

During operation of the manual breast pump 300, which is illustrated in FIGS. 36-38, the nursing mother grasps the pump and brings the cup assembly 318 into contact with one of her breasts B such that her nipple N is received through the elliptical opening 366 in the outer liner 340 and into the central passage 370 of the cup assembly. The outer liner 340 contacts the mother's nipple N and portions of her breast B around her nipple. Next, the breast pump 300 is activated by the mother squeezing and releasing the handle 327 to drive the pump 321 through one complete pumping cycle of the pump. The mother will continue squeezing and releasing the handle 327 to drive the pump 321 through as many cycles as desired by the mother. Often, the mother will operate the pump 321 until she stops expressing milk or has collected the desired quantity of milk.

As the mother squeezes the handle 327, the handle moves toward the coupler 320 and pivots about the mount 347 on the lid 325 to lift the stem 353 and thereby the lift assembly upward away from the lid. The stem 353 carries the actuator 357, the umbrella valve 359, the bellows 355, and diaphragm 383 with it as it moves upward. Upward movement of the diaphragm 383 causes the volume of the vacuum chamber 365 to increase thereby drawing air into the vacuum chamber through the check valve 343 from the primary chamber 341 of the coupler 320 and the central passage 370 of the cup assembly 318. Drawing air from the interior chamber 341 and central passage 370 causes a vacuum to form therein which results in a vacuum being applied to mother's nipple N received in the central passage of the cup assembly 318. In one suitable embodiment, the vacuum applied to the central passage 370 of the cup assembly 318 and thereby the mother's nipple N is in the range of 70 mm Hg to about 125 mm Hg. The amount of vacuum applied to the mother's nipple N can, in some embodiments, be variable within this range by rotation of the actuator 357, which correspondingly adjusts the position of the umbrella valve 359. The umbrella valve 359 provides a relief valve, which opens to reduce the vacuum within the vacuum chamber 365 should the vacuum with the vacuum chamber exceed the predetermined valve. The check valve 343 disposed in pneumatic communication with the vacuum chamber 365 and the primary channel 341 of the coupler 320 prevents the pressure within the primary channel of the coupler from exceeding atmospheric pressure.

The volume of the pressure chamber 367 is deceased as the lift assembly is raised during pivotal movement of the handle 327, which causes air to flow out of the pressure chamber and into the first and second pressure chambers 360, 372 of the breast cup via the respective pressure ports 391, 397 in the outer and inner inserts 391, 393. Filling the first and second interior chambers 360, 372 with air causes them to pressurize. In the illustrated embodiment, the first and second pressure chambers 360, 372 are pressurized simultaneously but it is contemplated that the first pressure chamber may be pressurized first followed by pressurization of the second chamber. Pressurization of the first and second pressure chambers 360, 372 results in a compressive force being applied to the mother's nipple N and a portion of the mother' breast B around her nipple N thereby driving milk M within her breast toward her nipple. In one suitable embodiment, the first and second interior chambers 360, 372 of the cup assembly 318 are pressurized to a pressure between about 70 mm Hg to about 100 mm Hg. The pressure relief valve 339 prevents the pressure within the pressure chamber 367 and thereby the first and second interior chambers 360, 372 of the cup assembly 318 from exceeding the predetermined pressure.

As seen in FIGS. 37 and 38, milk M expressed from the mother's breast B flows through the central passage 370 of the cup assembly 318, through the primary chamber 341 of the coupler 320 and into the container 322 by gravity. A partition 387 is located in the coupler 320 to divert the flow of milk downward toward the container 322 and thereby prevent milk M from flowing toward the pump housing 313.

The pumping cycle is repeated as often as necessary to express as much milk as the mother desires or is able to produce. The total pump cycle time of each pumping cycle is directly dependent on the rate at which the mother squeezes the handle 327. The faster the mother squeezes and releases the handle 327, the faster the pump cycle rate. The breast pump 300 described herein has been designed to more closely mimic the suckling of a nursing infant thereby providing a significantly more efficient and comfortable pump to mothers for expressing breast milk. More particularly, the breast pump 300 operates at a relatively low vacuum pressure as compared to conventional manual breast pumps, has a breast cup with an elliptical opening (generally mouth shaped) for receiving the nipple of the mother's breast and capable of applying a compressive force to the mother's breast around her nipple.

Figure 39:
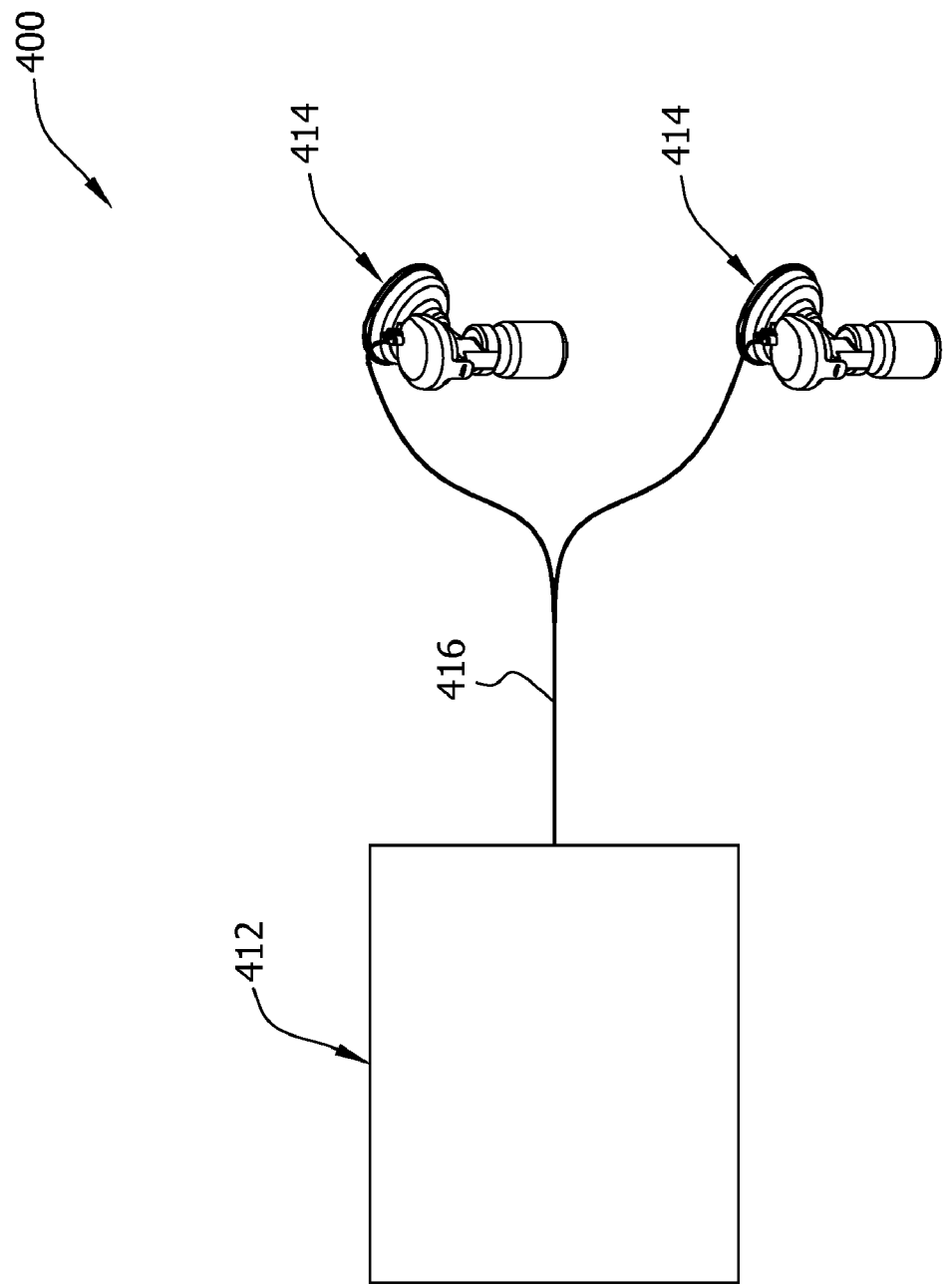
FIG. 39 is a schematic of yet another embodiment of an electric breast pump.

With reference now to FIG. 39, an electric breast pump according to yet another embodiment is schematically illustrated and is indicated generally at 400. The breast pump 400 includes a suitable housing, indicated generally at 412, for housing various working components such as pumps, a controller, and other components as will be described later herein. The breast pump 400 also comprises a pair of collection assemblies, indicated generally at 414, and flexible tubing or conduits 416 pneumatically connecting the collection assemblies to the housing. The housing 412 can be any suitable housing sized and configured for containing various components of the breast pump 400. The illustrated breast pump 400 includes a pair of collection assemblies 414 for expressing milk from both of a nursing mother's breasts, either simultaneously or independent of each other. It is contemplated that the collection assemblies 414 can be sufficiently independently operable so that a nursing mother can use only one of the two collection assemblies to express milk from a single breast. It is also contemplated that the breast pump 400 can be provided with a single collection assembly 414 for expressing milk from each of the nursing mother's breasts separately.

Figure 40:
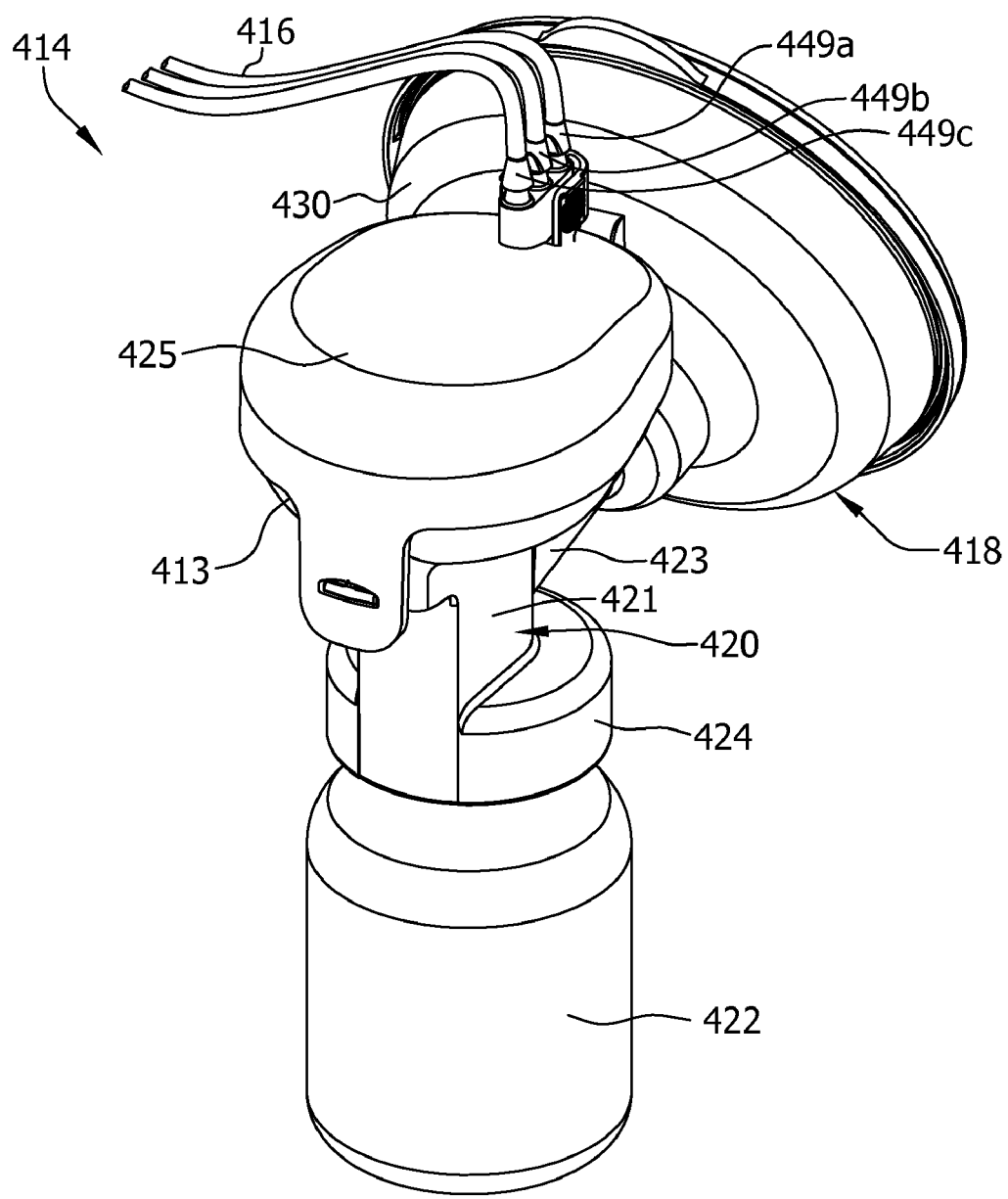
FIG. 40 is an enlarged perspective of one collection assembly of the breast pump of FIG. 39.

As illustrated in FIG. 40, each of the collection assemblies 414 comprises a cup assembly, indicated generally at 418, a coupler 420, and a container 422 for collecting milk expressed from the nursing mother's breast. In the illustrated embodiment, the container 422 is a dedicated milk collection and storage bottle. It is understood, however, that other types of containers can be used to collect the expressed breast milk. For example, the container 422 can be a conventional nursing bottle.

Figure 45:
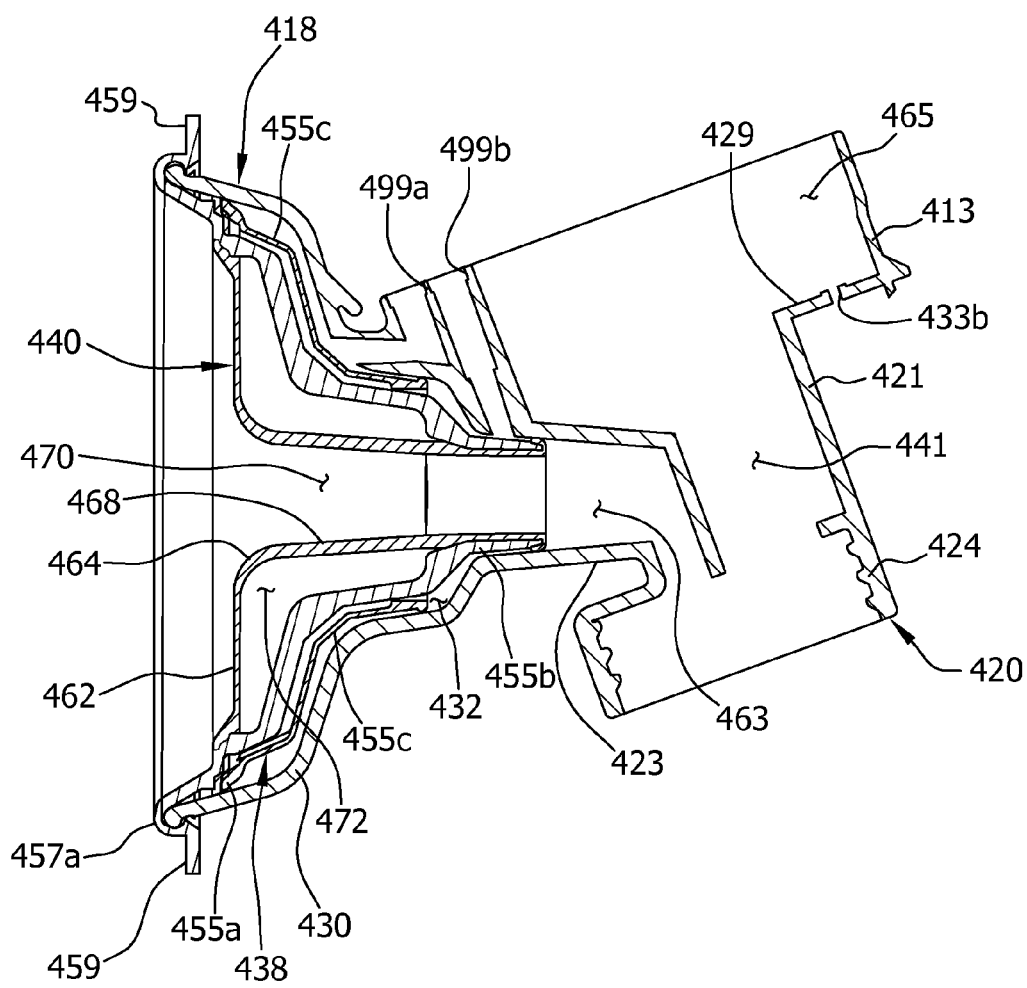
FIG. 45 is a cross-section taken along line 45-45 of FIG. 43.

As seen in FIG. 45, the coupler 420 has a primary tubular segment 421 defining a primary channel 441 oriented vertically in the drawings (e.g., to simulate the general orientation of the collection assembly in use), and a secondary tubular segment 423 extending outward from the primary segment at an angle relative thereto and defining a secondary channel 463 within the coupler. The coupler 420 includes a threaded lower socket 424, e.g., at the lower end of the primary segment 421, for threaded connection with the container 422 to couple the container to the coupler. In the illustrated embodiment, a portion of the cup assembly 418 is formed as one-piece with the coupler 420 and is connected to the coupler at the distal end of the secondary segment 423 to provide pneumatic and fluid communication between the cup assembly and the container 422 via the coupler. It is understood that couplers having other shapes and configurations can be used without departing from the scope of this invention. It is also understood that the coupler 420 may be releasably connected to the cup assembly 418. It is further understood that the coupler may be releasably connected to the container 422 in any suitable manner, such as, threads, and snap-fits, or other connection.

Figure 41:
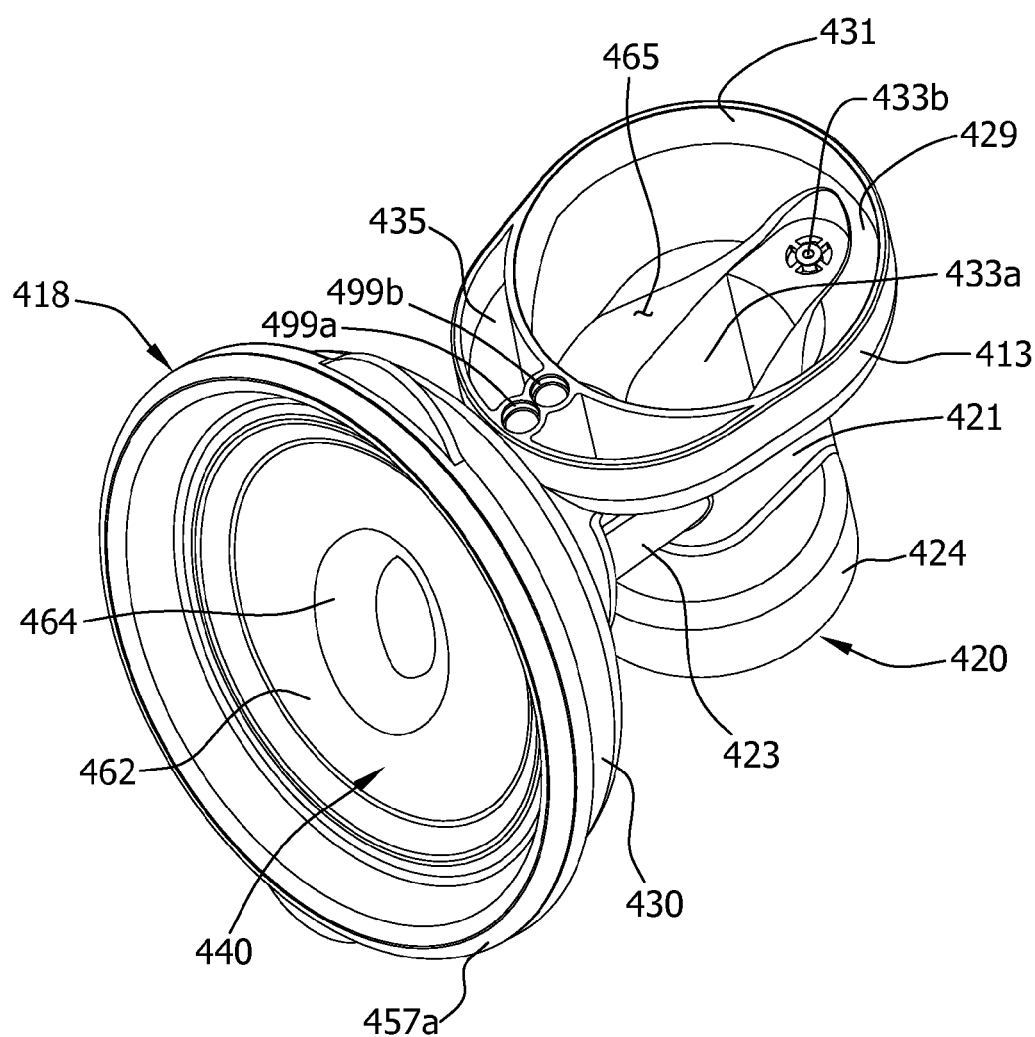
FIG. 41 is a perspective of a cup assembly of the collection assembly of FIG. 40.
Figure 42:
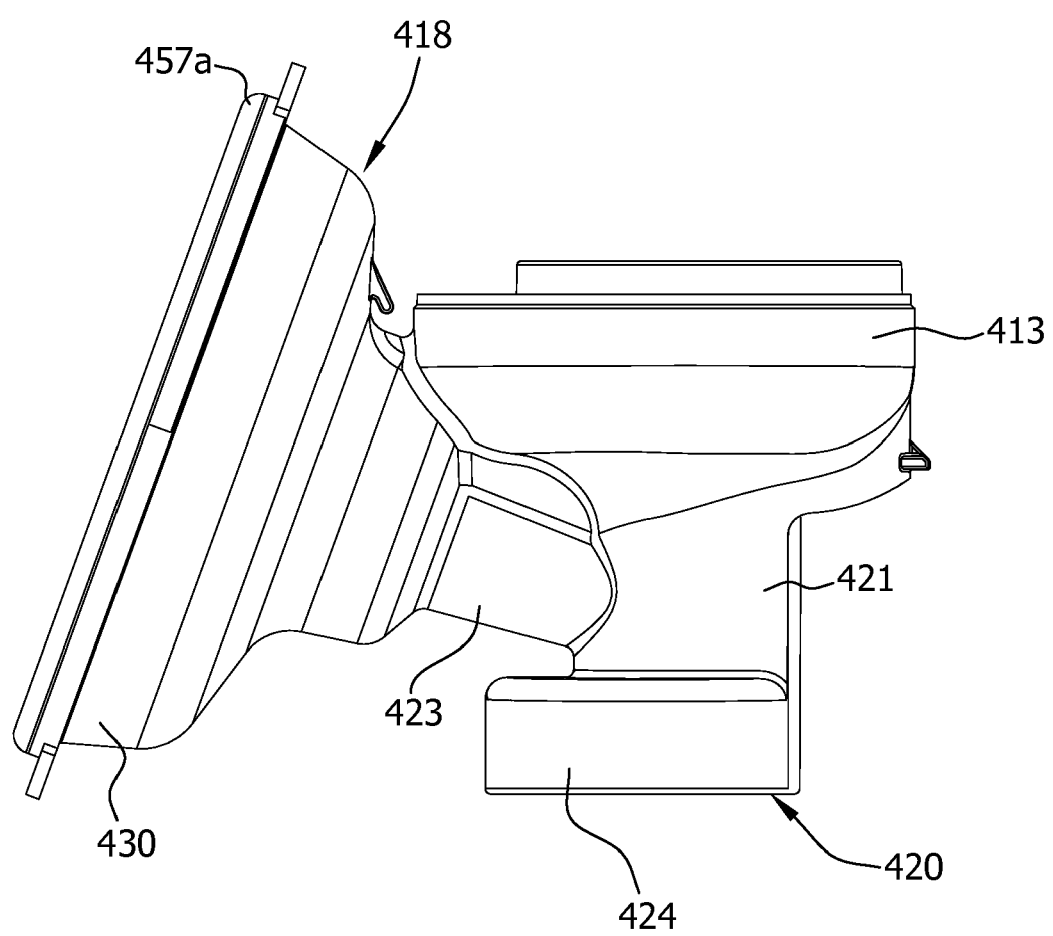
FIG. 42 is a side elevation of the cup assembly.

The coupler 420 also includes a generally cup-shaped housing 413 located above to the primary segment 421. As illustrated in FIG. 41, the housing 413 of the illustrated embodiment has a bottom 429 and a cylindrical wall 431 extending upward from the bottom. A flange 435 extends at least partially around the periphery of the cylindrical wall 431. The flange 435 includes two port openings 499a, 499b. The bottom 429 of the housing 413 includes a first aperture 433a in pneumatic communication with the primary channel 441 of the coupler 420 and a second aperture 433b in pneumatic communication with the atmosphere (i.e., the area outside of the housing). A relief valve 443b is associated with the aperture 433b in the housing 413 for inhibiting pressurization of an interior chamber 465 of the housing (FIGS. 41 and 47).

As seen in FIG. 40, a lid or cap 425 is mounted (e.g., by suitable threading, by snap fit, or other suitable mounting arrangement) on the coupler 420 at its top to sealingly close the coupler. More specifically, the lid 425 is mounted by snap fit on the housing 413 of the coupler 420. The lid 425 also includes three ports 449a, 449b, 449c. Two of the ports 449a, 449b are pneumatically connected to respective ones of the openings 499a, 499b in the flange 435 of the housing 413. The other port 449c is in pneumatic communication with the interior chamber 465 of the housing (FIG. 41).

Each cup assembly 418 is sized and shaped for receiving and forming a seal with one of the nursing mother's breasts, particularly at one of the mother's nipples. With reference to FIGS. 41-47, each of the cup assemblies 418 comprises a generally tubular, and more particularly a generally funnel-shaped, support member 430 having an interior or central passage 432 extending longitudinally therethrough (FIG. 45). As seen in FIG. 47, the support member 430 has a flanged longitudinally outer end 434. In this embodiment, the support member 430 of the cup assembly 418 is formed as a single-piece with the coupler 420 and the housing 413. The unitary coupler 420, housing 413, and support member 430 may be constructed of any suitable material but in a particularly suitable embodiment is sufficiently resistant to deformation in response to positive or negative pressure applied thereto at the operating pressures of the pump. For example, the unitary coupler 420, housing 413, and support member 430 may be suitably constructed of a generally rigid plastic. It is understood that the coupler 420, housing 413, and support member 430 can be formed separately and attached together in any suitable manner.

Figure 47:
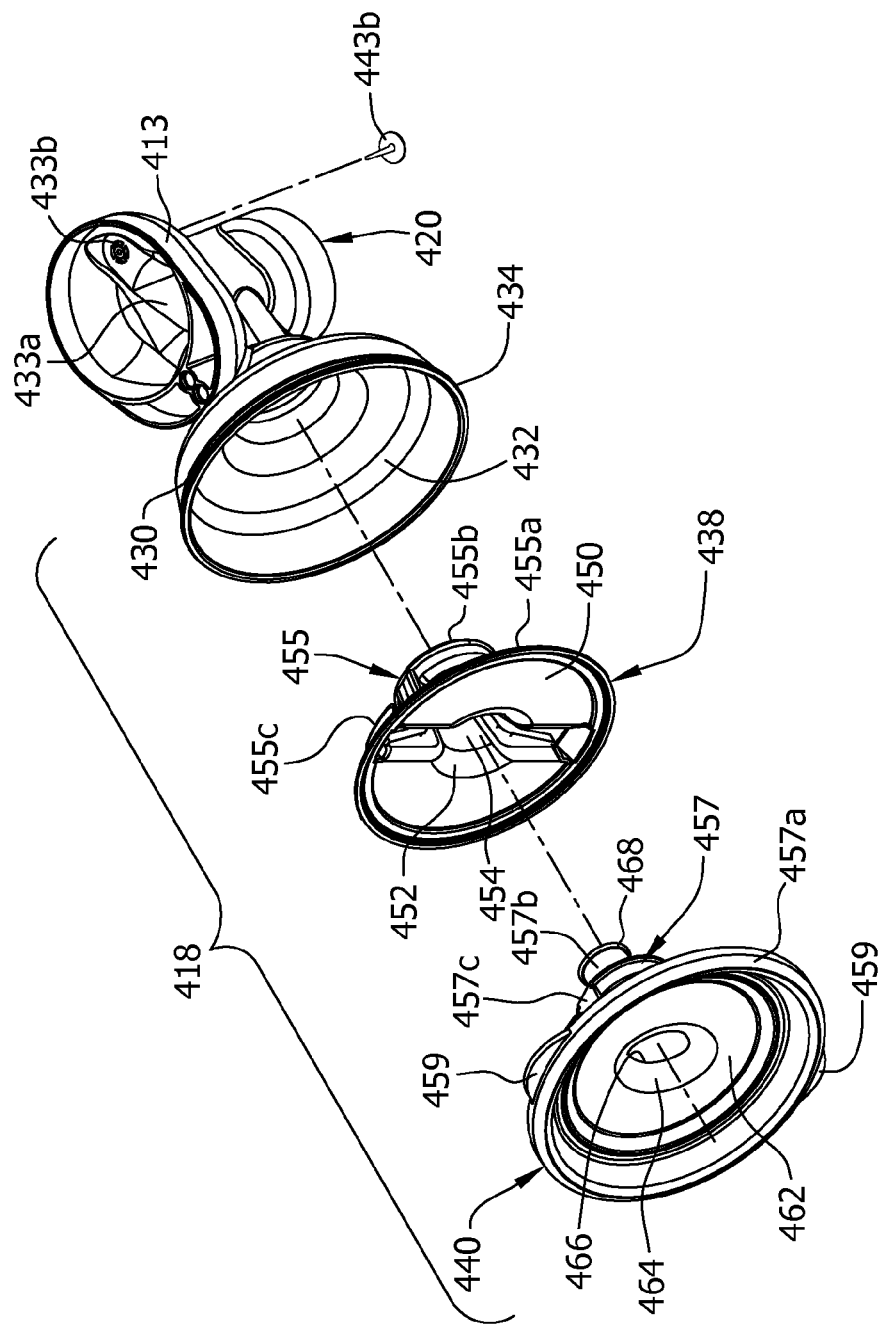
FIG. 47 is an exploded perspective of the cup assembly.

With reference still to FIG. 47, the cup assembly 418 further comprises a pair of expandable liners, referred to herein as inner liner, indicated generally at 438, and outer liner, indicated generally at 440. Each of the liners 438, 440 is suitably constructed, in part, of an elastic material to allow the liners to expand or stretch upon the application of pressure thereto, and then return to a less expanded or undeformed condition upon the removal of such pressure. For example, one suitable material from which the liners 438, 440 can be constructed is silicone. It is understood that the liners 438, 440 can be constructed of different materials and remain with the scope of this invention. It is contemplated that in another embodiment of the pump 400 (not illustrated), the inner liner 438 may be omitted.

Figure 46:
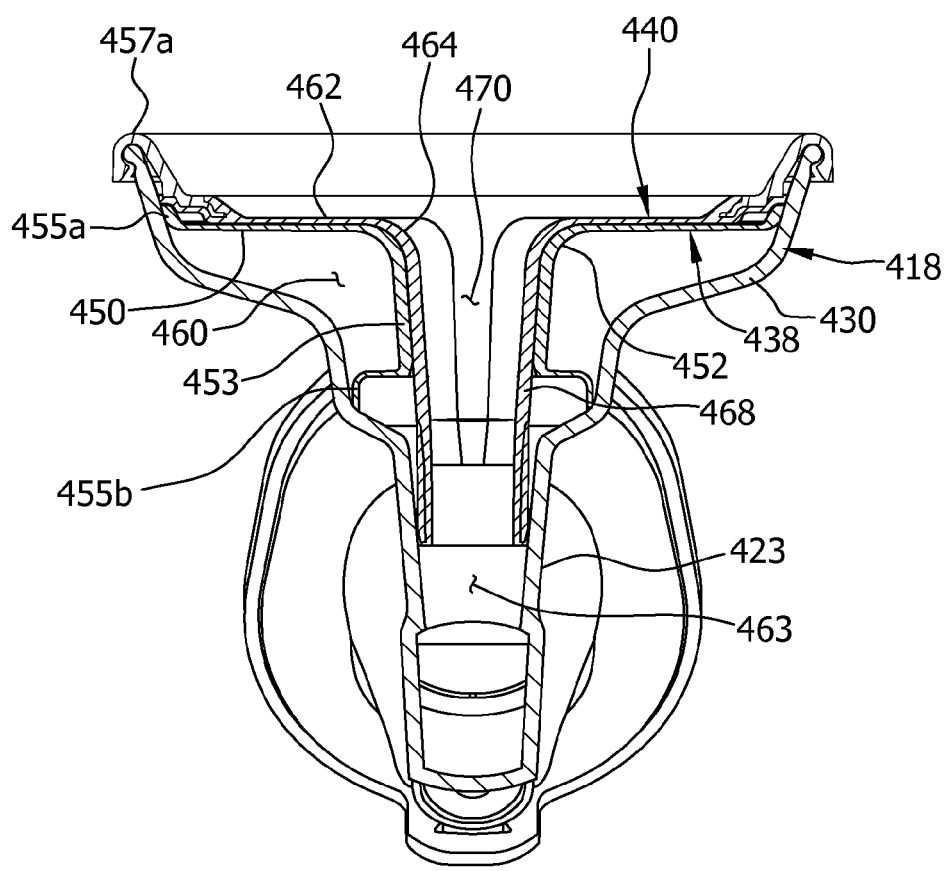
FIG. 46 is a cross-section taken along line 46-46 of FIG. 43.

With specific reference to FIGS. 45-47, the inner liner 438 is generally funnel-shaped and comprises an outer flange portion 450, a longitudinal portion 453 extending inward from the outer flange portions, and a tapered web portion 452 interconnecting the outer flange portion and the tapered web portion. In the illustrated embodiment, the outer flange portion 450, tapered web portion 452, and longitudinal portion 453 of the inner liner 438 are formed from the elastic material.

The inner liner 438 further defines a generally cruciform central opening 454, e.g., as defined by the tapered web portion 452 of the inner liner 438. As illustrated in FIG. 46, the inner liner 438 and the support member 430 cooperatively define a first pressure chamber 460 of the cup assembly 418.

The inner liner 438 also includes a rigid support frame, indicated generally at 455, having a first annular flange 455a surrounding the outer flange portion 450, a second annular flange 455b circling the longitudinal portion 453 and spaced from the first annular flange, and a pair of opposed support beams 455c extending between and interconnecting the first and second annular flanges. The support frame 455 provides rigidity to and supports the portions of the inner liner 438 made from elastic material (e.g., the outer flange portion 450, the longitudinal portion 453, and the tapered web portion 452). In the illustrated embodiment, the support beams 455c cooperatively bifurcate the outer flange portion 450, the longitudinal portion 453, and the tapered web portion 452 into two approximately equal halves such that the support beams is disposed between the two halves.

With reference still to FIGS. 45-47, the outer liner 440 is generally funnel shaped having a planar outer flange portion 462, a tapered central portion 464 extending from the outer flange portion, and longitudinal portion 468 extending longitudinally within the support member 430 from the tapered central portion of the outer liner to a terminal inner end of the outer liner adjacent the inner end of the support member. As seen in FIG. 47, the outer liner 440 has a generally elliptical (broadly, "noncircular") entry opening 466 defined by the outer flange portion 462 and tapered central portion 464, and a longitudinal channel 470 defined by the longitudinal portion 468. The longitudinal channel 470 defines a vacuum channel of the cup assembly 418 and is in pneumatic communication with the primary channel 441 of the coupler 420 and thereby the interior chamber 465 defined by the housing 413. The longitudinal channel 470 is also in fluid communication with the container 422. As illustrated in FIG. 45, the outer liner 440 and inner liner 438 at least in part cooperatively define a second pressure chamber 472 of the cup assembly 418.

The outer liner 440 also includes a rigid support frame, indicated generally at 457, having a first annular flange 457a surrounding the outer flange portion 462, a second annular flange 457b circling the longitudinal portion 468 and spaced from the first annular flange, and a pair of opposed support beams 457c extending between and interconnecting the first and second annular flanges. The support frame 455 provides rigidity to and supports the portions of the outer liner 440 made from the elastic material (e.g., the outer flange portion 462, the longitudinal portion 468, and the tapered web portion 464). In the illustrated embodiment, the support beams 457c are spaced from the outer flange portion 462, the longitudinal portion 468, and the tapered web portion 464. A pair of tabs 459 extends outward from the first annular flange 457a for grasping the outer liner 440.

As seen in FIGS. 45 and 46, the liners 438, 440 are adapted for mating with each other. More specifically, the openings 454, 466 and the longitudinal portions 453, 468 of the inner and outer liners 438, 440 are aligned coaxially with each other and the outer flange portion 450 of the inner liner is positioned in face-to-face engagement with the outer flange portion 462 of the outer liner. The support beams 457c of the outer liner 440 are received in recesses formed in the support beams 455c of the inner liner 438. In the illustrated embodiment, the inner and outer liners 438, 440 are selectively separate for cleaning but it is understood that the inner liner could be formed as one-piece with outer liner or permanently attached to the outer liner, e.g., by bonding the inner liner to the outer liner.

Figure 43:
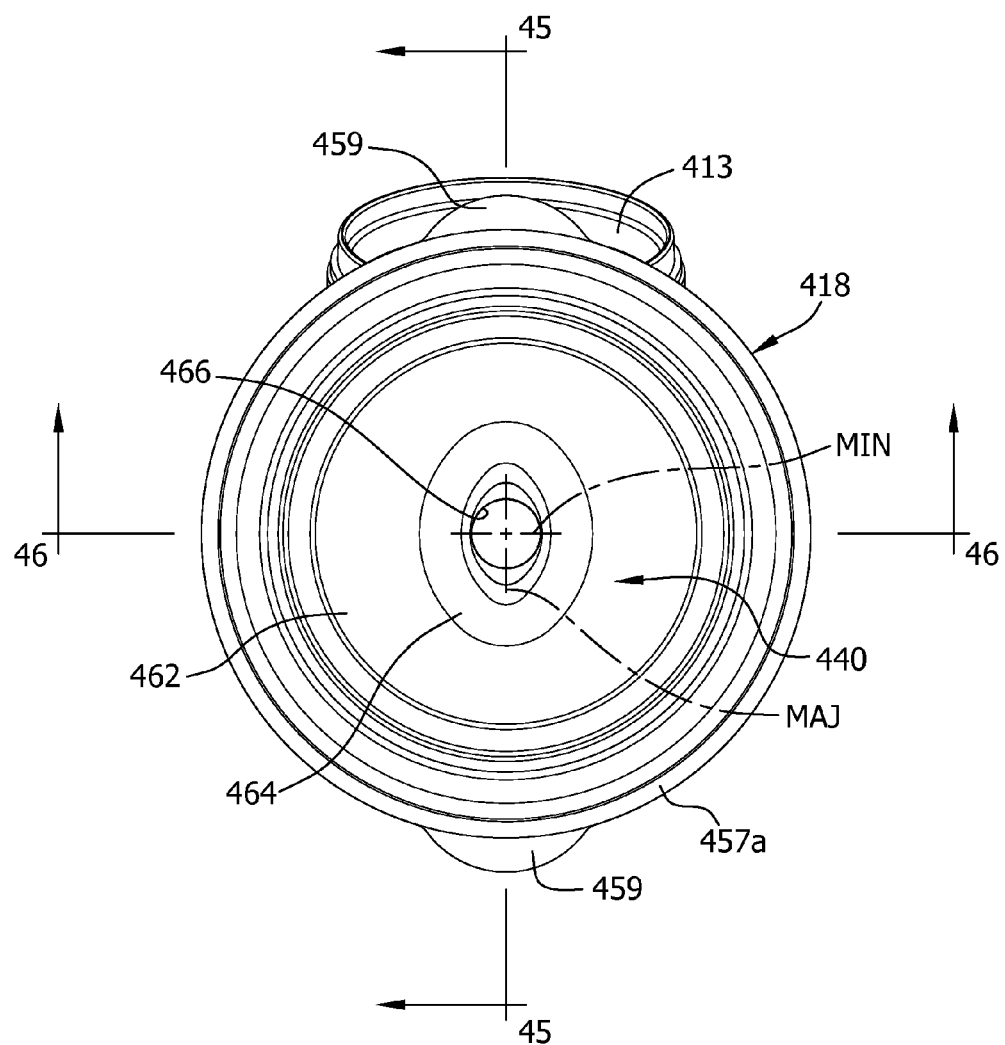
FIG. 43 is a plan view of the cup assembly with an outer liner of the cup assembly in an opened configuration.
Figure 44:
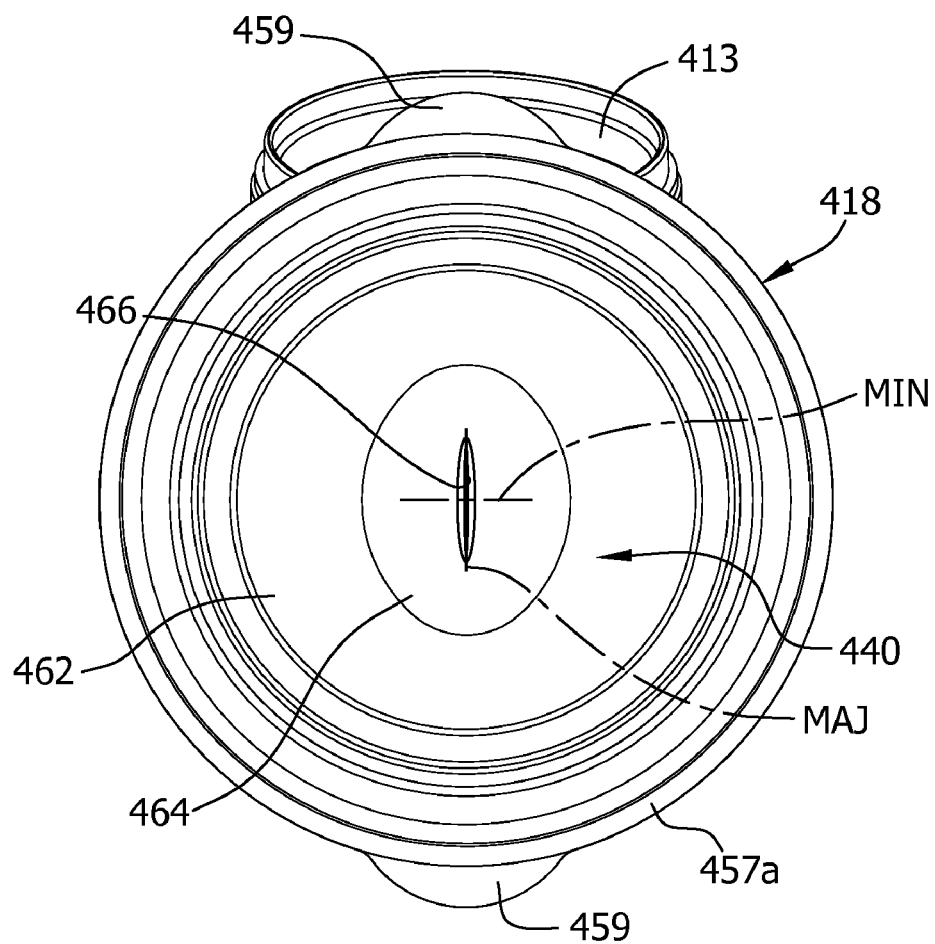
FIG. 44 is a plan view similar to FIG. 43 with the outer liner of the cup assembly moved to a generally collapsed configuration.

As illustrated in FIGS. 43 and 44, the elliptical opening 466 in the outer liner 440 defines the entry opening into which the mother's breast (e.g., her nipple) is inserted into the cup assembly and has a major axis MAJ and minor axis MIN. The outer liner 440 is configured for hinged-like movement generally about the major axis MAJ of the opening 466 between the fully opened configuration, which is illustrated in FIG. 43, and a collapsed configuration, which is illustrated in FIG. 44, in response to pressure applied to the liners (e.g., vacuum pressure in the central passage of the outer liner and/or positive pressure applied to the first and second pressure chambers). This hinged-liked movement more accurately simulates the oral movements applied by a suckling infant to the mother's breast.

In the illustrated embodiment, the outer annular flange 457a of the rigid support frame 455 of the outer liner 440 has a snap-fit connection with the flanged longitudinally outer end 434 of the support member 430 to thereby releasably secure the liners 438, 440 to the cup assembly 418. As a result, the inner and outer liners 438, 440 can be removed and individually cleaned. It is understood that the liners 438, 440 can be releasably attached to the cup assembly 418 in other ways.

Figure 48:
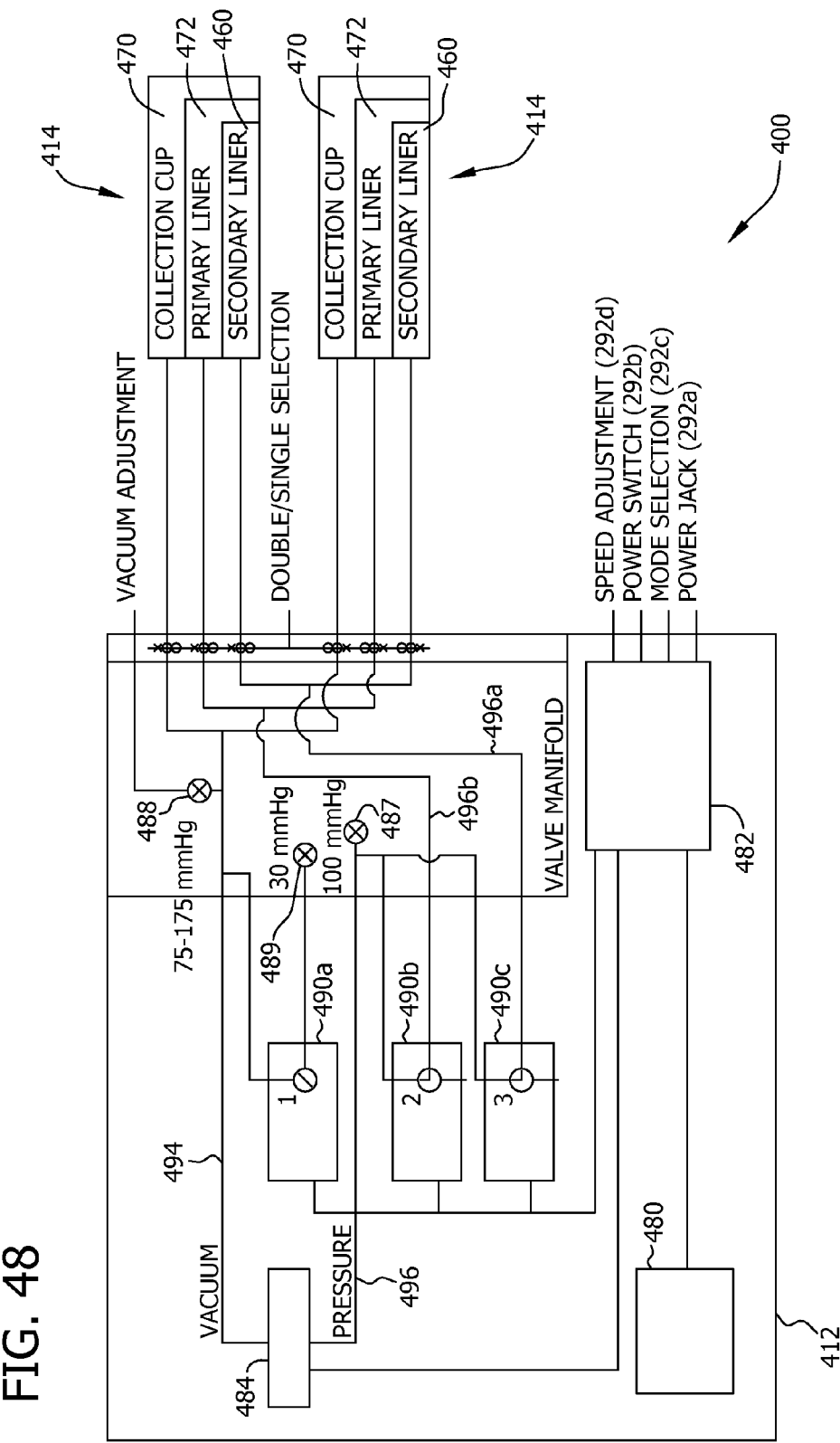
FIG. 48 is a schematic illustrating the interconnection of the various components of the of the electric breast pump.

With reference now to the schematic illustrated in FIG. 48, the breast pump 400 also comprises a power supply 480, a controller 482, and a vacuum/positive pressure pump 484. A first regulator valve 488 (e.g., otherwise referred to as a relief valve may be suitably constructed in the manner of a screw-type adjustable valve) is in pneumatic communication with the pump 484 for adjusting the maximum operating (suction) vacuum pressure that can be applied by the vacuum pump to the mother's breast. A second regulator valve 489 is in pneumatic communication with the pump 484 for maintaining a minimum operating (latching) vacuum pressure that can be applied by the vacuum pump to the mother's breast. Solenoid valves 490a-490c (e.g., three being illustrated in FIG. 48) are provided to regulate the timing of positive pressure and vacuum pressure applied to the cup assemblies 418 by the pump 484. In one suitable embodiment, the power supply 480, the controller 482, the pump 484, the regulator valves 488, 489 and the solenoid valves 490a-490c are disposed in the housing 413. While the present embodiment includes a single vacuum/positive pressure pump 484, it is understood that separate vacuum and pressure pumps could be used.

In one embodiment, the power supply 480 is sufficiently sized to provide power to operate the pump 400 including the controller 482, the pump 484, and the solenoid valves 490a-490c for an entire day. For example, the power supply 480 can be sufficiently sized to operate the pump 10 to 12 times for 15 to 20 minutes per time over a 24 hour period. In one suitable embodiment, the power supply 480 will be a rechargeable battery that can be quickly recharged. In one example, the power supply 480 can be recharged in about 3.5 hours using a suitable external source (e.g., a standard 110 volt outlet). Suitably, the power supply 480 can be charged during use. That is, any residual power from the external source not being used to operate the pump will go to recharging the power supply 480. The power supply 480 can be connected to the suitable external recharging source using a power jack 492a. In addition, the pump 400 can be operated from power supplied by the external source via the power jack 492a. An LED can be located on the housing 412 for indicating to the user the status of the battery. In one example, the LED being solid green indicates that the battery is charged, solid yellow indicates that the battery is charging, and blinking yellow indicates that the battery needs to be charged. It is contemplated that the power supply 480, as illustrated in FIG. 48, can be omitted from the housing 412. In this embodiment, power can be supplied to the breast pump 400 via the power jack 492a from any suitable external source of power (e.g., a conventional 110 volt outlet). The LED, in this embodiment, can be used to indicate voltage status.

In one suitable embodiment, the controller 482 is a programmable logic controller (PLC) that is specifically programmed to turn on and off pump 484 and to individually open and close each of the solenoid valves 490a-490c. The controller 482 includes an on/off switch 492b for allowing the nursing mother to selectively turn the breast pump 400 on and off. In one embodiment, the on/off switch comprises a push button. In one suitable embodiment, the push button is pressed for at least 50 milliseconds to turn the pump 400 on, and for at least 500 milliseconds to turn the pump off. That is, the push button has to be pressed considerably longer to turn the pump 400 off than it does to turn the pump on. The controller 482 also includes a mode selection switch 492c for switching the pump 400 from a stimulating mode to an expressing mode, which are described in more detail below, and a speed adjustment 492d for adjusting the cycle rate at which the pump is operated. LEDs can be used to indicate to the user of the pump 400 which mode the pump is operating. In one embodiment, one LED can be provided to indicate that the pump is operating in its stimulating mode and another LED can be provided to indicate that the pump is operating in its expressing mode. In another embodiment, a single LED can be flashed to indicate simulating mode, and constantly illuminated to indicate expressing mode.

The conduit 416, as illustrated in FIGS. 39, 40 and 48, comprises a vacuum conduit 494 pneumatically connecting the pump 484 via the regulator valves 488, 489 and solenoid valve 490a to each of the collection assemblies 414 and in particular to the central passages 470 of the cup assemblies 418 (e.g., the central passage of the outer liner 440). One of the solenoid valves, e.g., valve 490a is disposed along the vacuum conduit 494 to regulate the level of vacuum pressure applied by the pump 484 to the mother's breast within the central passage 470. That is, the solenoid valve 490a is controlled by the controller 482 and can be programmed to be closed or opened for a specified period of time. In its opened position, the solenoid valve 490a vents the vacuum conduit to atmosphere to reduce or eliminate the vacuum pressure generated by the pump 484, thus allowing control over the level of vacuum pressure applied to the mother's breast via each of the cup assemblies 418. Thus, the solenoid valve 490a can be used to apply a predetermined vacuum pressure level to the central passages 470 within a range achievable by the pump 484.

In one suitable embodiment, the pump 484 is capable of applying a maximum vacuum of up to 150 millimeters of mercury (mm Hg) to the central passages 470 of each of the cup assemblies 418. More suitably, in operation of the pump 484, the regulator valves 488, 489 and the solenoid valve 490a are operated to regulate vacuum pressure in the central passages 470 of the cup assemblies 418 (e.g., the vacuum pressure experienced by the mother's breast) in the range of about 70 mm Hg to about 130 mm Hg, more suitably in the range of about 75 mm Hg to about 125 mm Hg. It is understood, however, that the pump 484 can apply vacuum pressure other than within the above ranges without departing from the scope of this invention. It is important that the maximum pressure within the central passage 470 of each of the cup assemblies 418 be maintained below a level that would result in discomfort and/or tissue damage to the mother's breasts.

The maximum pressure within the central passage 470 of each of the cup assemblies 418, however, should be sufficient to draw milk expressed from the mother breasts from the cup assemblies into the container 422.

One or more pressure conduits 496 pneumatically connect the pump 484 to each of the collection assemblies 414 and more particularly to the first (via conduit 496a) and second (via conduit 496b) pressure chambers 460, 472 of the cup assemblies 418 (FIG. 48). Thus, the pump 484 can be used to independently pressurize the first pressure chamber 460 and the second pressure chamber 472 of each cup assembly 418 to selectively and independently expand the respective inner and outer liners 438, 440. In one suitable embodiment, the pump 484 is capable of pressurizing each of the first and second pressure chambers 460, 472 up to a maximum pressure established by the relief valve 487. In one suitable embodiment, the maximum pressure established by the relief valve 487 is about 100 mm Hg. It is understood, however, that the pump 484 can pressurize the first and second pressure chambers 460, 472 of the cup assemblies 418 between different ranges of positive pressure than those provided herein without departing from the scope of this invention.

One of the solenoid valves 490c is disposed along the first conduit 496a for selectively regulating the pressurization of the first pressure chamber 460, and another solenoid valve 490b is disposed along the second conduit 496b for selectively regulating the pressurization of the second pressure chamber 472. As mentioned above, the solenoid valves 490b, 490c are controlled by the controller 482 and can be programmed to be closed or opened for a specified period of time. Thus, the solenoid valves 490b, 490c along the first and second conduits 496a, 496b can be used in their opened positions to selectively pressurize the first and second pressure chambers 460, 472 at any positive pressure within the limits of the pump 484 for a predetermined period of time. The solenoid valves 490b, 490c, which are three way valves, also facilitate independent venting or depressurization of the respective pressure chambers 460, 472. The solenoids valves 490b, 490c when moved to their closed position allow for selectively venting (in whole or in part) the first pressure chamber 460 and second pressure chamber 472, respectively. Thus, the solenoid valve 490b, 490c along the first and second conduits 496a, 496b can be opened to selectively pressurize the first and second pressure chambers 460, 472 and can be closed to selectively depressurize the first and second pressure chambers for predetermined periods of time.

In the illustrated schematic, the cup assemblies 418 are operated simultaneously using the same solenoid valves 490a-490c. It is understood, however, that each of the cup assemblies 418 may be controlled independently of each other. That is, each of the cup assemblies 418 may be provided independent sets of solenoid valves with each respective set of solenoid valves controlled independently by the controller 482. It is also understood that the collection assemblies 414 and specifically the cup assemblies 418 described herein may be configured for use with a manual pump.

Operation of the breast pump 400 will now be described with reference to a single one of the collection assemblies 414, it being understood that operation of the other collection assembly is substantially the same as that described herein. In operation, the nursing mother brings the cup assembly 418 of the collection assembly 414 and in particular the outer liner 440 into contact with one of her breasts, with her nipple generally received through the elliptical opening 466 into the central passage 470 of the cup assembly. In this position, the planar outer flange portion 462 and tapered portion 464 of the outer liner 440 lay against the mother's breast surrounding the nipple. The breast pump 400 is activated by moving the on/off switch 492 of the controller 482 to its on position, thereby initiating the stimulating mode of pumping cycle of the breast pump. The stimulating mode is designed to mimic an infant's initial suckling (e.g., non-nutritive suckling), which causes the mother to experience "let down." "Let down" occurs when milk within the mother's breast flows toward her nipple.

In the stimulating mode, the pump 484 is operated to apply a suction (e.g., maximum) vacuum pressure to the mother's breast within the central passage 470 of the outer liner 440. For example, a maximum vacuum pressure in the range of about 30 mm Hg to about 150 mm Hg, more suitably in the range of about 75 mm Hg to about 125 mm Hg is applied to the breast within the central passage 470 of the outer liner 440. In one particularly suitable embodiment, the suction vacuum pressure is applied to the mother's breast continuously throughout the cycle. It is understood, however, that the suction vacuum pressure can be selectively varied through the cycle.

The pump 484 is also operated to pressurize the first pressure chamber 460 (e.g., as defined by the inner liner 438) of the cup assembly 418 to apply a compressive pressure against the mother's breast at a location relatively distal from the end of the mother's nipple. For example, in one suitable embodiment, the first pressure chamber 460 is pressurized to a pressure of about 70 mm Hg to about 100 mm Hg, and more suitably about 85 mm Hg. This is done by the controller 482 moving the solenoid valve 490c disposed along the first conduit 496a of the pressure conduit 496 to its opened position to pressurize the first pressure chamber 460. Pressurizing the first pressure chamber 460 in this manner causes the expansion of the inner liner 438 (and hence the outer liner 440 in the region of the inner liner) away from the support member 430 to apply pressure to the mother's breast within the central passage 470 of the outer liner 440. In one suitable embodiment, the first pressure chamber 460 is pressurized continuously for approximately the first fifteen cycles of the stimulating mode and depressurized continuously for approximately the next ten cycles (i.e., cycles sixteen through twenty-five). The first pressure chamber 460 is pressurized and depressurized in this pattern continuously through the stimulating mode.

The second pressure chamber 472 (e.g., defined by the outer liner 440) is pressurized to apply a compressive pressure against the mother's breast at a location nearer to and in some embodiments adjacent the end of the mother's nipple. For example, in one suitable embodiment, the second pressure chamber 472 is pressurized to a pressure of about 70 mm Hg to about 100 mm Hg, and more suitably about 85 mm Hg. In particular, the controller 482 moves the solenoid valve 490b disposed along the second conduit 496b of the pressure conduit 496 to pressurize the second pressure chamber 472 to the desired pressure. This causes the outer liner 440 to expand inward away from the support member 430 thereby reducing the height of the central passage 470 to apply pressure to the mother's breast. In one embodiment, the pressure in the second pressure chamber 472 is suitably the same as the pressure in the first pressure chamber 460. It is understood, however, that the pressure in the second pressure chamber 472 may be greater than or less than that in the first pressure chamber 460 without departing from the scope of this invention.

In one suitable embodiment, the second pressure chamber 472 is pressurized in the range of about 30 to about 60 percent of each cycle, and more suitably about 50 percent of each cycle. In one particularly suitable embodiment, pressurization of the second pressure chamber 472 is delayed following the start of each cycle and discontinued before the end of each cycle. As such, the second pressure chamber 472 quickly pressurizes and depressurizes to simulate the quick, shallow sucks of a baby during the onset of feeding (i.e., non-nutritive suckling). As mentioned above, non-nutritive suckling of a baby causes the milk in the nursing mother's breast ducts to flow toward her nipple, where it can be expressed.

In the stimulating mode, the pumping cycle is repeated as often as necessary to cause the mother to experience let down. In one suitable embodiment, the pumping cycle of the breast pump 400 is moved automatically from the stimulating mode to the expressing mode after about 90 seconds. The mother can manually move the pumping cycle from the stimulating mode to the expressing mode using the mode selector switch. The corresponding LED located on the housing 413 is illuminated to inform the mother which mode the pumping cycle is currently in.

In one suitable embodiment, the breast pump 400 is operable in the range of about 90-120 cycles per minute during the stimulating mode. One example of a suitable stimulating mode is summarized in the following table.

the range of about 50 to about 80 percent of each cycle, and more suitably about 70 percent of each cycle.

The pump 484 is also operated to pressurize the first pressure chamber 460 (e.g., as defined at least in part by the inner liner 438) of the cup assembly 418 to apply a compressive pressure against the mother's breasts at a location relatively distal from the end of the mother's nipple. For example, in one suitable embodiment, the first pressure chamber 460 is pressurized to a pressure of about 30 mm Hg to about 100 mm Hg, and more suitably about 85 mm Hg. This is done by the controller 482 opening the solenoid valve 490c disposed along the first conduit 496a of the pressure conduit 496 to pressurize the first pressure chamber 460. Pressurizing the first pressure chamber 460 in this manner causes the expansion of the inner liner 438 (and hence the outer liner 440 in the region of the inner liner) away from the support member 430 to apply pressure to the mother's breast within the central passage 470 of the outer liner 440. In one suitable embodiment, the first pressure chamber 460 is pressurized in the range of about 50 to about 80 percent of each cycle, and more suitably about 70 percent of each cycle.

| Cycles 1-15 of the Stimulating mode Time (seconds) | Positive Pressure in the first interior chamber (mm Hg) | Positive Pressure in the second interior chamber (mm Hg) | Vacuum applied to the Central Passage (mm Hg) |
|---|---|---|---|
| 0 | 70-100 | 0 | 70-175 |
| 0.1 | 70-100 | 70-100 | 70-175 |
| 0.25 | 70-100 | 70-100 | 70-175 |
| 0.35 | 70-100 | 70-100 | 70-175 |
| 0.5 | 70-100 | 0 | 70-175 |

| Cycles 16-25 of the Stimulating mode Time (seconds) | Positive Pressure in the first interior chamber (mm Hg) | Positive Pressure in the second interior chamber (mm Hg) | Vacuum applied to the Central Passage (mm Hg) |
|---|---|---|---|
| 0 | 0 | 0 | 70-175 |
| 0.1 | 0 | 70-100 | 70-175 |
| 0.25 | 0 | 70-100 | 70-175 |
| 0.35 | 0 | 70-100 | 70-175 |
| 0.5 | 0 | 0 | 70-175 |

It is contemplated that the stimulating mode of the pumping cycle can be omitted in some embodiments of the pump 400 without departing from some aspects of this invention.

The expressing mode of the pumping cycle is suitably designed to simulate the suckling action and frequency of a nursing infant, e.g., the peristaltic movement of the infant's tongue and palate used to express milk. In particular, during each cycle the pump 484 is operated to apply a suction (e.g., maximum) vacuum pressure to the mother's breast within the central passage 470 of each of the cup assemblies 414. For example, a vacuum pressure in the range of about 70 mm Hg to about 150 mm Hg and more suitably in the range of about 75 mm Hg to about 125 mm Hg is applied to each of the breasts within the respective central passages 470. More specifically, the controller 482 moves the solenoid valve 490a to its opened position to thereby allow the desired maximum vacuum pressure (as limited by the regulator valve 488) to be applied to mother's breast. The vacuum pressure facilitates the collection of milk expressed from the mother's breasts and aids in maintaining the cup assemblies 418 on the mother's breasts. In one particularly suitable embodiment, the suction vacuum pressure is applied to the mother's breast in At least about the same time that the first pressure chamber 460 is pressurized, and more suitably shortly thereafter, the second pressure chamber 472 (e.g., defined at least in part by the outer liner 440) is pressurized to apply a compressive pressure against the mother's breast at a location nearer to and in some embodiments adjacent the end of the mother's nipple. For example, in one suitable embodiment, the second pressure chamber 472 is pressurized to a pressure of about 70 mm Hg to about 100 mm Hg, and more suitably about 85 mm Hg. In particular, the controller 482 opens the solenoid valve 490b disposed along the second conduit 496b of the pressure conduit 496 to pressurize the second pressure chamber 472 to the desired pressure. This causes the outer liner 470 to expand inward away from the support member 430 thereby reducing the height of the central passage 470 to apply pressure to the mother's breast. In one embodiment, the pressure in the second pressure chamber 472 is suitably the same as the pressure in the first pressure chamber 460. It is understood, however, that the pressure in the second pressure chamber 472 may be greater than or less than that in the first pressure chamber 460 without departing from the scope of this invention.

In one suitable embodiment, the second pressure chamber 472 is pressurized in the range of about 30 to about 60 percent of each cycle, and more suitably about 50 percent of each cycle. In one particularly suitable embodiment, pressurization of the second pressure chamber 472 is delayed a suitable period following initial pressurization of the first pressure chamber 460 during each cycle such that the cycle time during which both the first and second pressure chambers are pressurized terminates at the same time during the cycle. As such, the first and second pressure chambers 460, 472 are pressurized sequentially to facilitate the flow of breast milk toward the mother's nipples where it can be expressed. Moreover, the hinged movement of the inner and outer liners 438, 440 in response to the vacuum pressure in the central passage 470 of the outer liner and the pressurization of the first and second pressure chambers 460, 472 more accurately simulates the tongue and palate movement of the suckling infant. Breast milk expressed from the mother's breast flows through the central passage 470 of the outer liner 440 into the secondary channel 463 of the coupler 420, down into and through the primary channel 441 thereof, and into the container 422.

Once both the first and second pressure chambers 460, 472 are fully pressurized during a suction cycle, the vacuum in the central passage 470 of the cup assembly 418 is reduced to about 30 mm Hg by the controller 482 opening solenoid valve 490a to vent the vacuum path. The 30 mm Hg vacuum simulates the latching pressure of a suckling infant and also maintains the cup assembly 418 on the mother's breast.

Finally, both the first and second pressure chambers 460, 472 are vented by opening the corresponding solenoid valves 490b, 490c which cause the chambers to depressurize to atmospheric pressure. Upon depressurization, the inner and outer liners 438, 440 return in large part (with the exception to any small deformation due to the latching pressure) to their initial or undeformed configuration. After the depressurization is complete, the valve 490a is closed so that the central passage 470 and hence the mother's breast therein is subjected to the suction vacuum pressure again for the next cycle.

The pumping cycle is repeated as often as necessary to express as much milk as the mother desires or is able to produce. The pumping cycle of the breast pump 400 is stopped by manually moving the on/off switch 492 of the controller 482 to the off position. In one suitable embodiment, the breast pump is operable in the range of about 50-90 cycles per minute, more suitably about 60-70 cycles per minute, and even more suitably about 60 cycles per minute (about 1 second per cycle). One example of a suitable pump cycle for the expressing mode is summarized in the following table.

operates through a timed cycle that is intended to simulate the peristaltic movement of an infant's tongue and palate.

Figure 49:
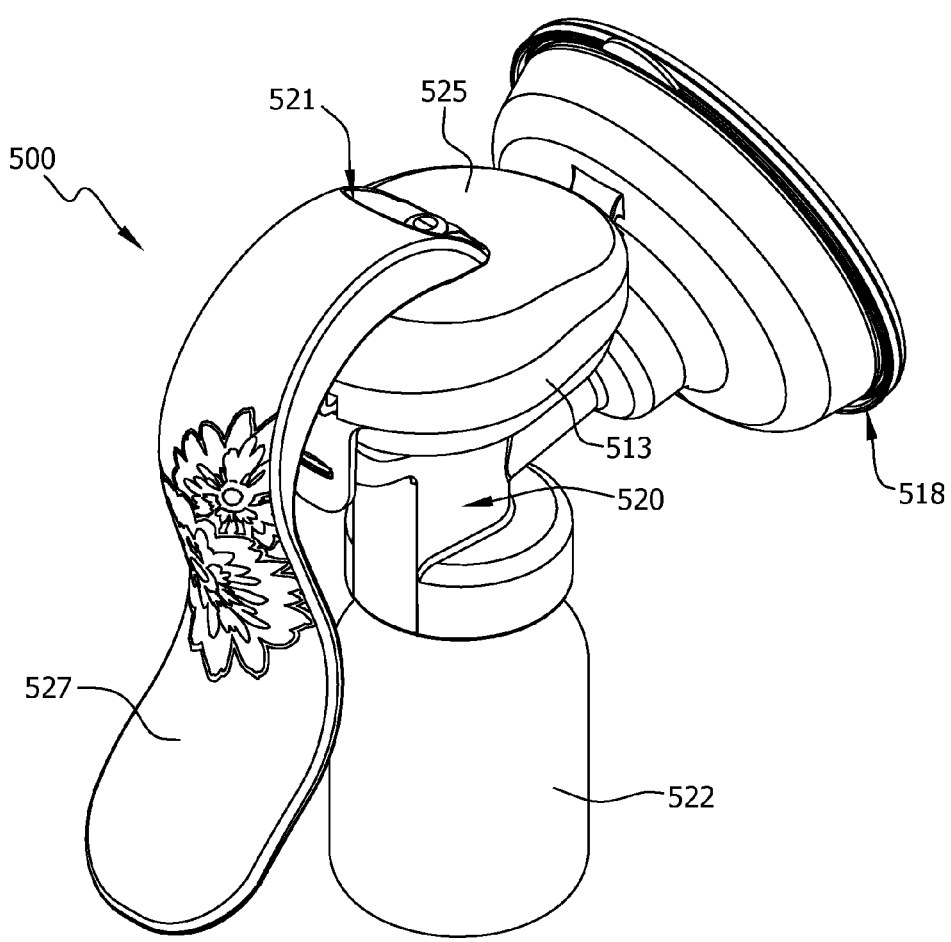
FIG. 49 is a perspective of yet another embodiment of a manual breast pump having a container attached thereto.

With reference now to FIGS. 49-58, and specifically FIG. 49, a manual breast pump according to another embodiment is indicated generally at 500. The illustrated manual breast pump 500 includes a pump, indicated generally at 521, a cup assembly, indicated generally at 518, a coupler 520, and a container 522 for receiving milk expressed from a nursing mother's breast by the breast pump. In the illustrated embodiment, the coupler 520 and container 522 are substantially similar to the coupler 420 and container 422 described above with respect to FIGS. 39-48. Thus, the illustrated container 522 is a dedicated milk storage bottle but could be a conventional nursing bottle or other suitable container capable of collecting expressed breast milk.

Figure 56:
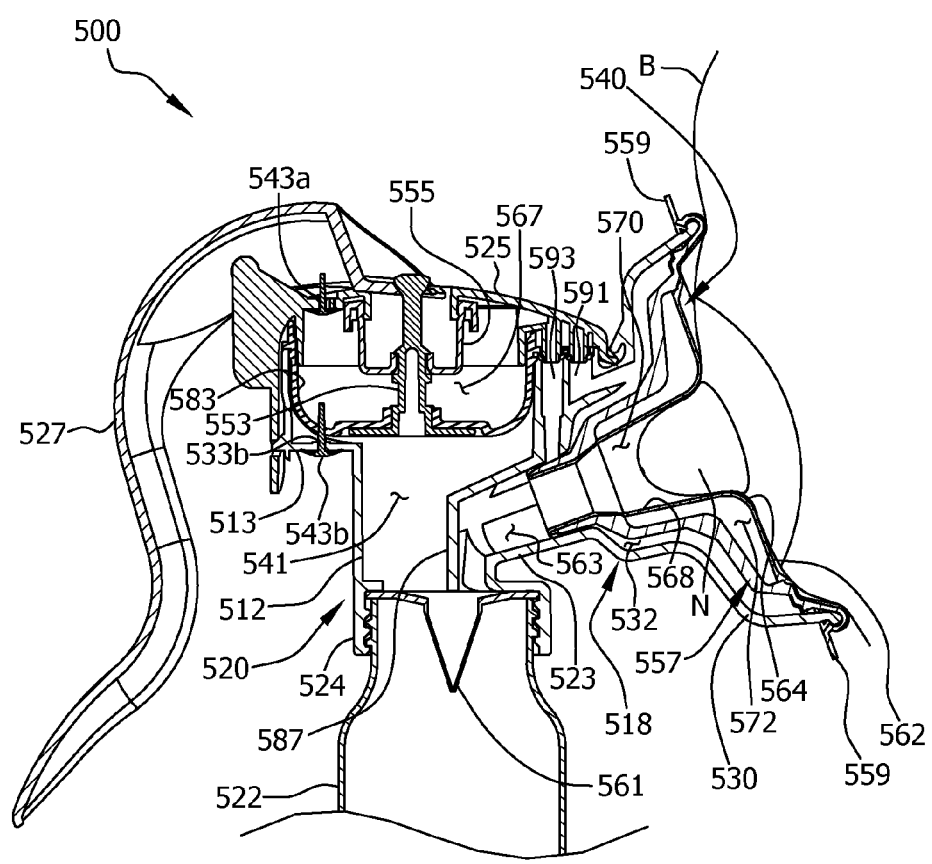
FIG. 56 is a cross-section of the manual breast pump taken along line 56-56 of FIG. 52 with a handle of the pump in a relaxed position.
Figure 57:
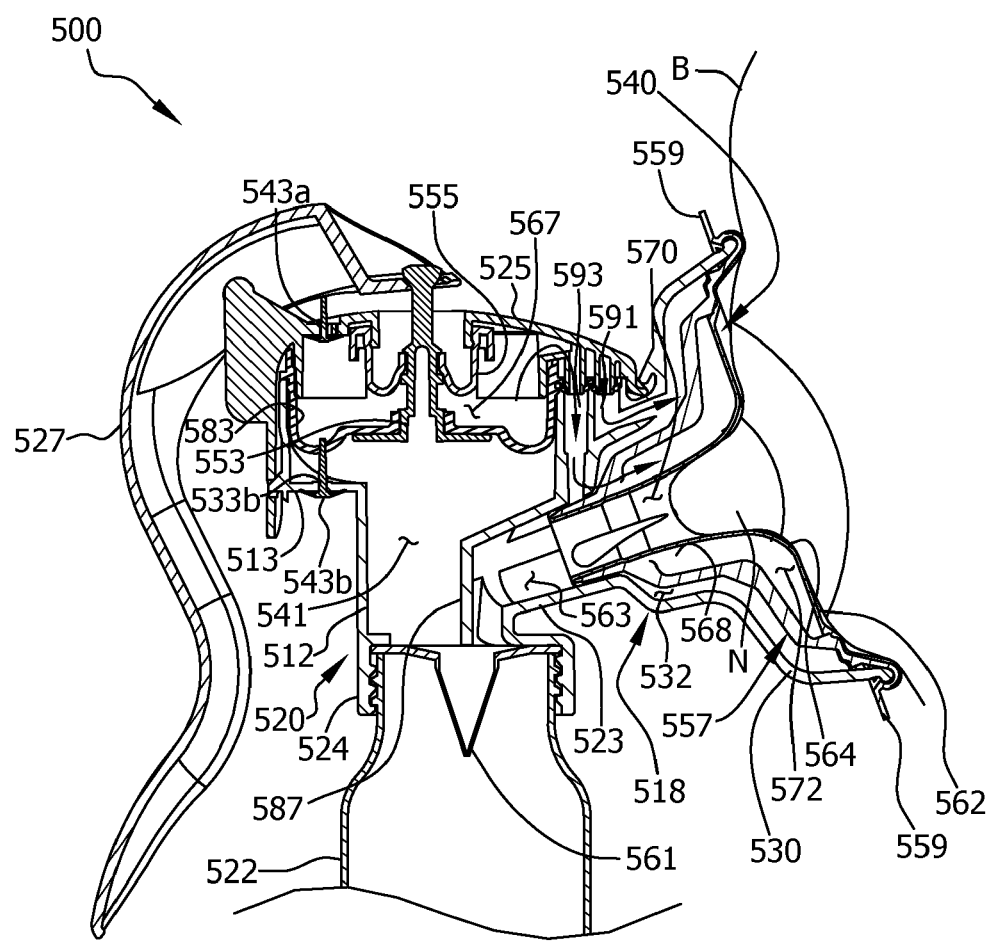
FIG. 57 is a cross-section similar to FIG. 56 but with the pump handle in a partially compressed position.
Figure 58:
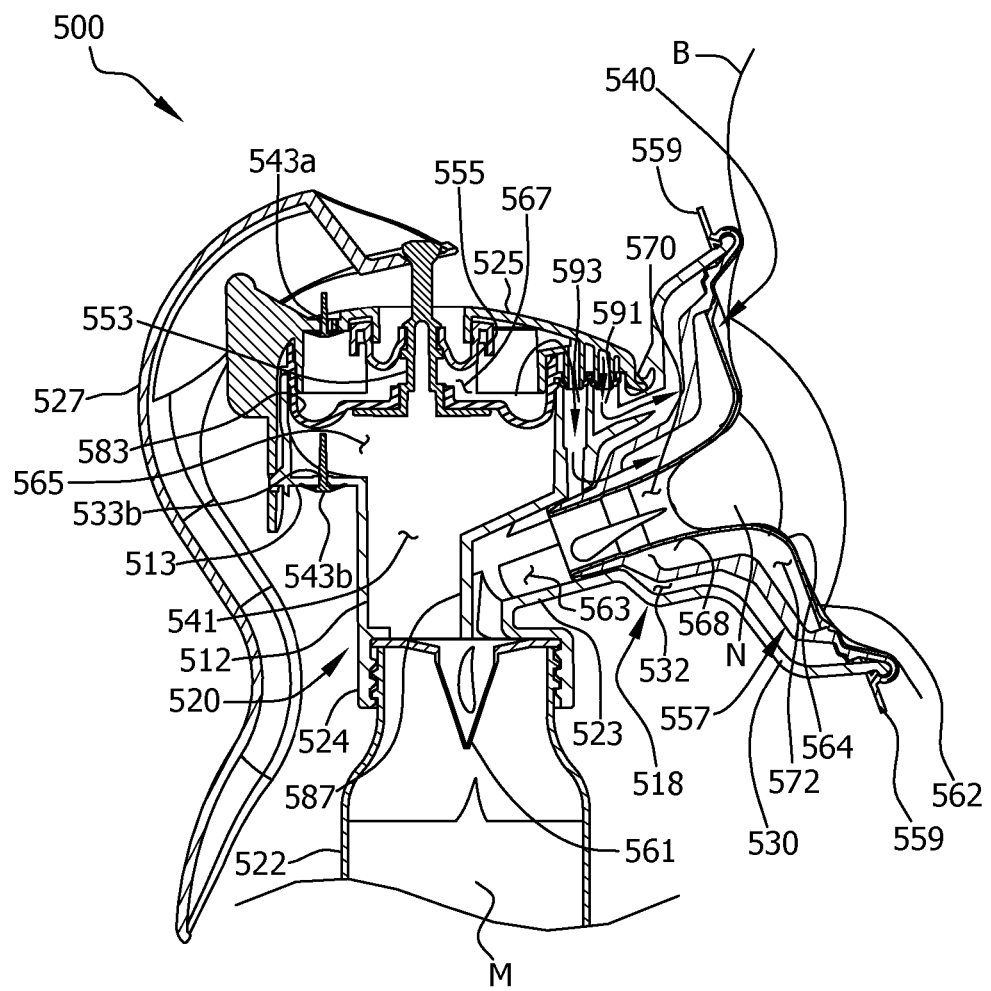
FIG. 58 is a cross-section similar to FIGS. 56 and 57 but with the pump handle in a fully compressed position.

As illustrated in FIGS. 56-58, the coupler 520 has a primary tubular segment 512 defining a primary channel 541 oriented vertically in the drawings (e.g., to simulate the general orientation of the collection assembly in use), and a secondary tubular segment 523 extending outward from the primary segment at an angle relative thereto and defining a secondary channel 563 within the coupler. The coupler 520 includes a threaded lower socket 524, e.g., at the lower end of the primary segment 512, for threaded connection with the container 522 to couple the container to the coupler. The cup assembly 518 is mounted on the coupler 520 at the distal end of the secondary segment 523 to provide pneumatic and fluid communication between the cup assembly and the container 522 via the coupler. It is understood that couplers having other shapes and configurations can be used without departing from the scope of this invention. It is also understood that the coupler 520 may connect to the cup assembly 518, and/or container 522 in any suitable manner, such as, threads, and snap-fits, or other connection.

Figure 50:
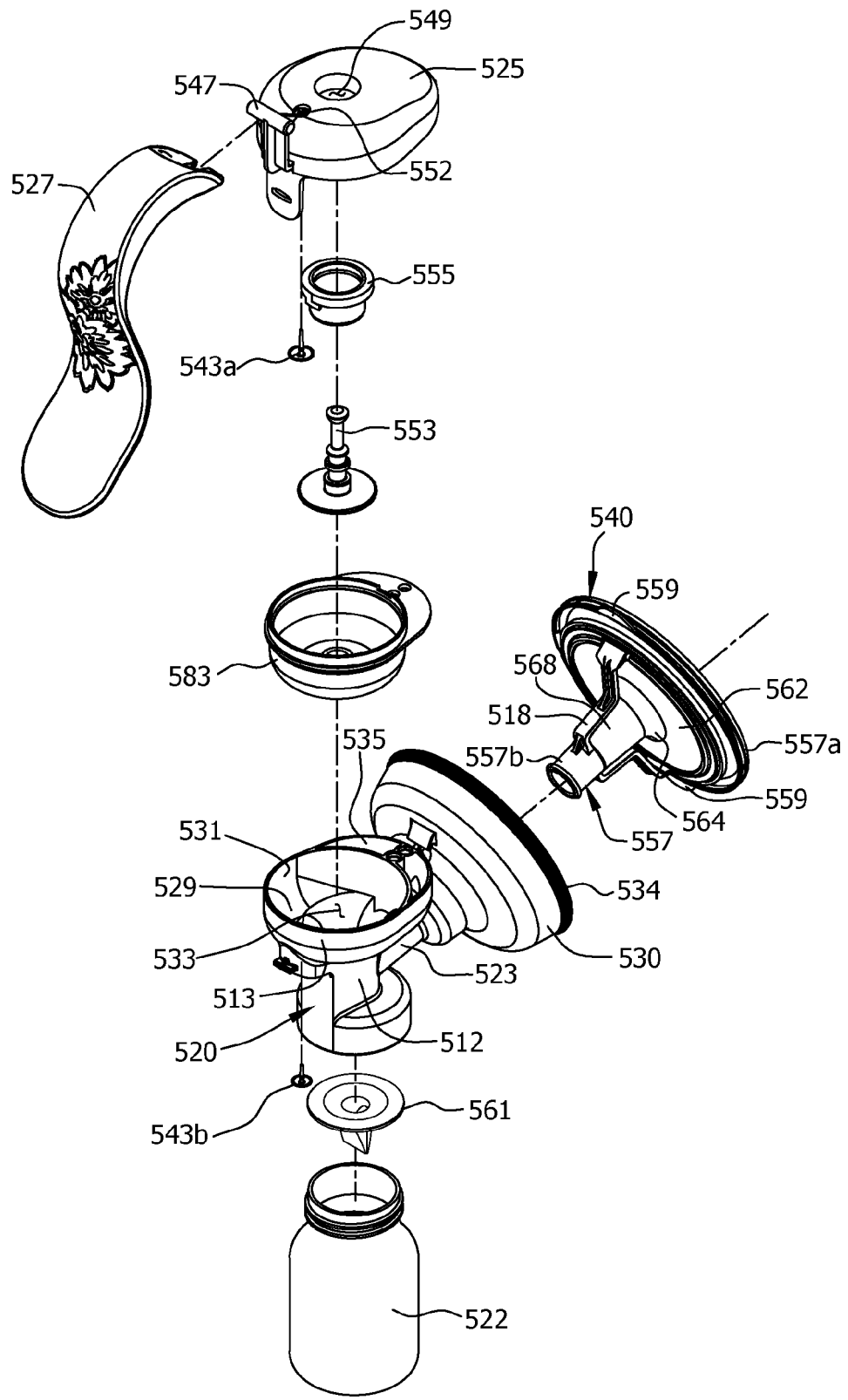
FIG. 50 is an exploded perspective of the manual breast pump with a portion of the container cut away.
Figure 51:
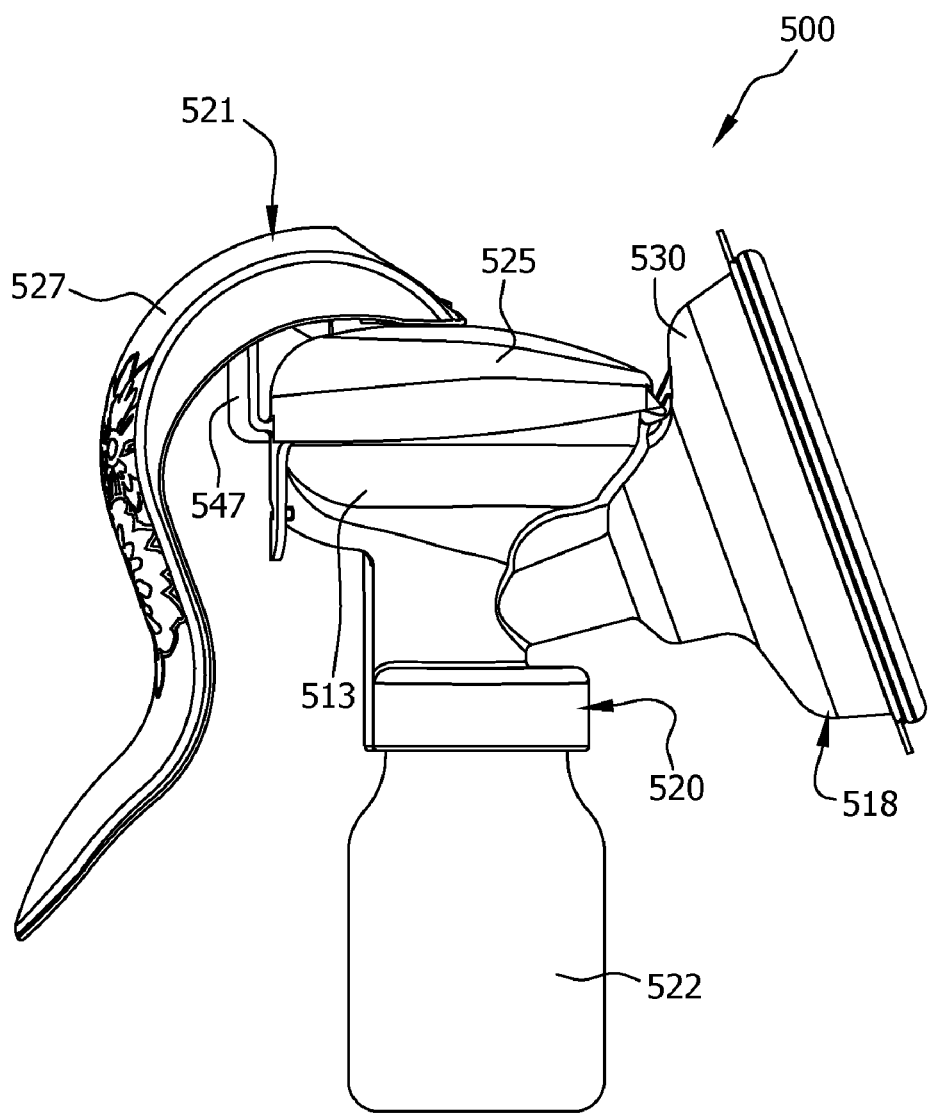
FIG. 51 is a side elevation of the manual breast pump.
Figure 52:
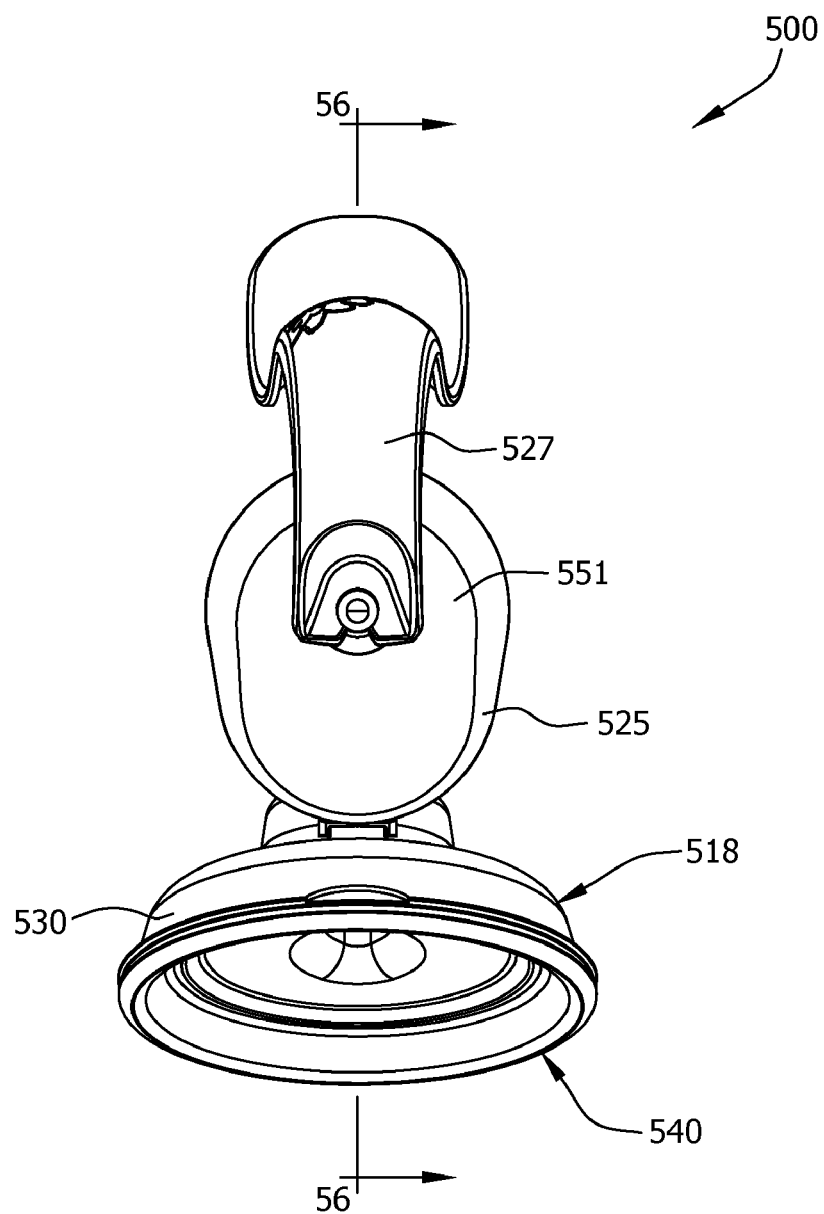
FIG. 52 is a plan view of the manual breast pump.
Figure 53:
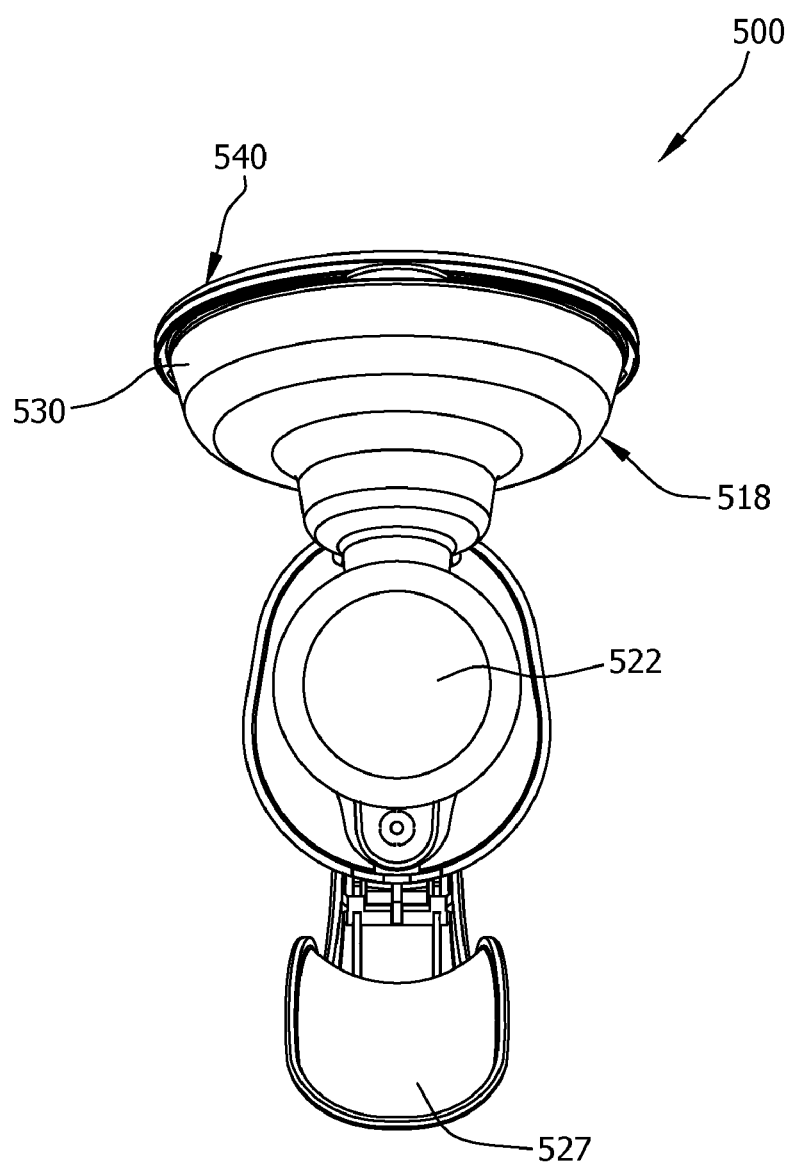
FIG. 53 is a bottom view of the manual breast pump.

As illustrated in FIG. 50, the coupler 520 also includes a pump housing 513 located above the primary segment 512. The pump housing 513 of the illustrated embodiment is generally cup shaped having a bottom 529 and a cylindrical wall 531 extending upward from the bottom. A flange 535 extends at least partially around the periphery of the cylindrical wall 531. The bottom 529 of the pump housing 513 includes a first aperture 533 in pneumatic communication with the primary channel 541 of the coupler 520 and a second aperture 533b in pneumatic communication with the atmosphere (i.e., the area outside of the housing). A relief valve 543b is associated with

| Expressing Mode Pump Cycle Time (seconds) | Positive Pressure in the first interior chamber (mm Hg) | Positive Pressure in the second interior chamber (mm Hg) | Vacuum applied to the Central Passage (mm Hg) |
|---|---|---|---|
| 0 | 70-100 | 0 | 70-175 |
| 0.2 | 70-100 | 70-100 | 70-175 |
| 0.5 | 70-100 | 70-100 | 30 |
| 0.7 | 0 | 0 | 70-175 |
| 1 | 70-100 | 0 | 70-175 |

The breast pump 400 described herein has been designed to more closely mimic the suckling of a nursing infant thereby providing a significantly more efficient and comfortable pump to mothers for expressing breast milk. More particularly, the breast pump 400 operates at a relatively low vacuum pressure as compared to conventional breast pumps, has a cup assembly with an elliptical opening (generally mouth shaped) and capable of hinged movement at the opening, sequentially applies compressive pressure to the mother's breast, and the aperture 533b in the housing 513 for inhibiting pressurization of a vacuum chamber 565 (FIG. 56)

With reference again to FIG. 49, a lid or cap 525 is mounted (e.g., by suitable threading, by snap fit, or other suitable mounting arrangement) on the coupler 520 at its top to sealingly close the coupler. More specifically, the lid 525 is mounted by snap fit on the pump housing 513 of the coupler 520. Referring now to FIG. 50, the lid 525 has a mount 547 for pivotally mounting a handle 527 of the pump 521 thereon.

The lid 525 also includes a generally central opening 549 and a vent opening 552. A check valve 543a is associated with the vent opening 552 in the pump housing 513 for regulating the amount of vacuum that can be created with a pressure chamber 567 (FIG. 58).

With reference still to FIGS. 50 and 56, the handle 527 of the illustrated embodiment of the pump 521 is generally S-shaped and is pivotally mounted on the mount 547 of the lid 525 via a snap-connection therewith. The handle 527 can be manually squeezed and released to operate the pump 521. Thus, the handle 527 can be selectively moved between a relaxed position (FIG. 56) and a fully compressed position (FIG. 58). It is understood that the handle 527 can have other shapes and configurations.

The handle 527 is operatively connected to a lift assembly of the pump 521. As seen in FIGS. 50 and 56, the lift assembly comprises a stem 553, a bellows 555, and a diaphragm 583. The stem 553 extends through the central opening 549 in the lid 525. The stem 553, as illustrated in FIGS. 56-58, includes a tubular wall extending between opened upper and lower ends. The lower end of the stem 553 includes an annular flange extending outward from the tubular wall. A pair of spaced apart ribs is disposed on an exterior surface of the tubular wall of the stem 553. The bellows 555 is a flexible membrane that is disposed within the pump housing 513 and affixed at one of its ends to the lid 525 adjacent the central opening 549 therein. The opposite end of the bellows 555 is affixed to the stem 553 between the pair of ribs. The stem 553 is operatively connected to the handle 527 so that movement of the handle between its relaxed and compressed positions results in corresponding movement of the lift assembly.

As seen in FIGS. 56-58, the diaphragm 583 is received in the pump housing 513 and comprises a flexible membrane. One end of the diaphragm 583 is captured between the lid 525 and the pump housing 513 and is affixed at its opposite end to the flange of the stem 553. As best illustrated in FIG. 58, the diaphragm 583 and the pump housing 513 collectively define the vacuum chamber 565 for inducing a vacuum in the primary channel 541 of the coupler 520. The diaphragm 583, the lid 525, and the bellows 555 collectively define the pressure chamber 567 for pressurizing the cup assembly 518 as will be described in more detail below.

As seen in FIGS. 56-58, the cup assembly 518 is sized and shaped for receiving and forming a seal with one of the nursing mother's breasts, particularly at one of the mother's nipples. Specifically, the cup assembly 518 comprises a generally tubular, and more particularly a generally funnel-shaped, support member 530 having an interior or central passage 532 extending longitudinally therethrough (FIG. 56). As seen in FIG. 50, the support member 530 has a flanged longitudinally outer end 534. In this embodiment, the support member 530 of the cup assembly 518 is formed as a single-piece with the coupler 520 and the pump housing 513. The unitary coupler 520, pump housing 513, and support member 530 may be constructed of any suitable material but in a particularly suitable embodiment is sufficiently resistant to deformation in response to positive or negative pressure applied thereto at the operating pressures of the pump. For example, the unitary coupler 520, pump housing 513, and support member 530 may be suitably constructed of a generally rigid plastic. It is understood that the coupler 520, pump housing 513, and support member 530 can be formed separately and attached together in any suitable manner.

With reference to FIG. 50, the cup assembly 518 further comprises a liner, indicated generally at 540, suitably constructed, in part, of an elastic material to allow the liner to expand or stretch upon the application of pressure thereto, and then return to a less expanded or undeformed condition upon the removal of such pressure. For example, one suitable material from which the liner 540 can be constructed is silicone. It is understood that the liner 540 can be constructed of different materials and remain with the scope of this invention.

Figure 54:
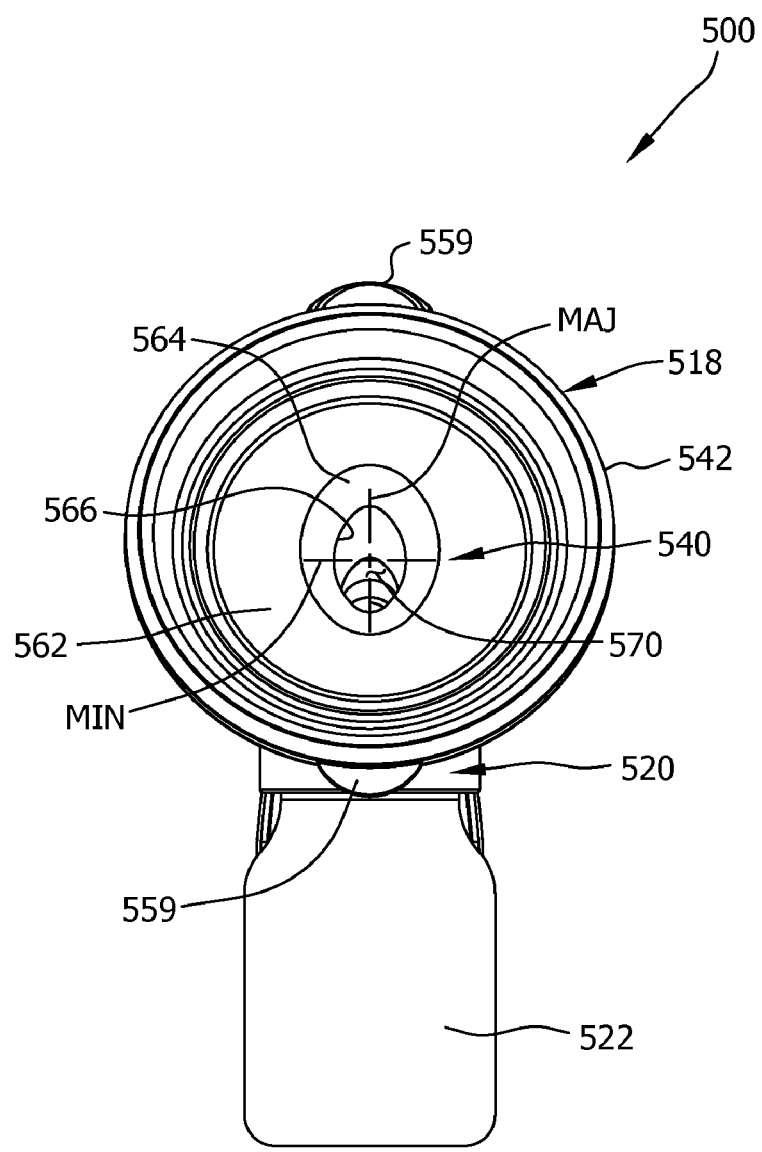
FIG. 54 is a front view of the manual breast pump.
Figure 55:
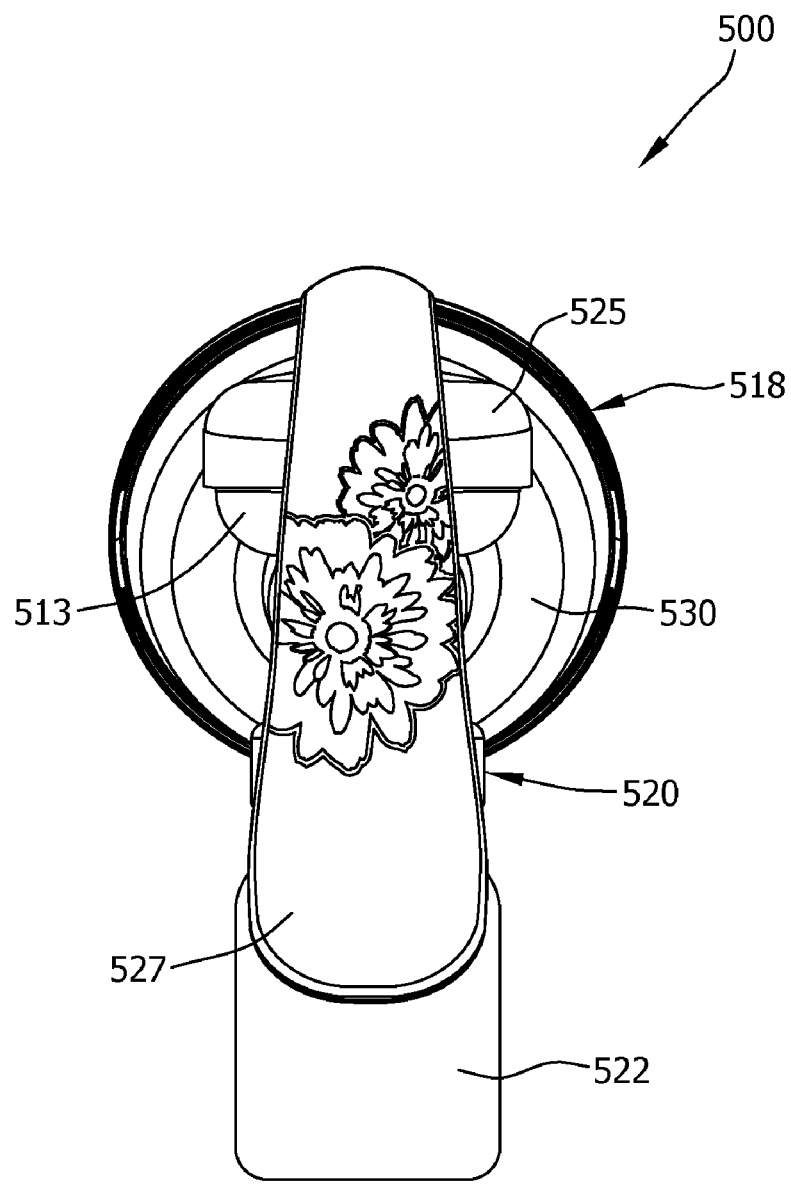
FIG. 55 is a back view of the manual breast pump.

As illustrated in FIGS. 50 and 54, the liner 540 is generally funnel shaped having a planar outer flange portion 562, a tapered central portion 564 extending from the outer flange portion, and a longitudinal portion 568 extending longitudinally within the support member 530 from the tapered central portion of the liner to a terminal inner end of the liner adjacent the inner end of the support member 530. The liner 540 also includes a rigid support frame, indicated generally at 557, having a first annular flange 557a surrounding the outer flange portion 562, a second annular flange 557b circling the longitudinal portion 568 and spaced from the first annular flange, and a pair of opposed support beams 557c extending between and interconnecting the first and second annular flanges. The support frame 557 provides rigidity to and supports the portions of the liner 540 made from the elastic material (e.g., the outer flange portion 562, the longitudinal portion 568, and the tapered web portion 564). In the illustrated embodiment, the support beams 557c are spaced from the outer flange portion 562, the longitudinal portion 568, and the tapered web portion 564. A pair of tabs 559 extends outward from the first annular flange 557a for grasping the liner 540.

As seen in FIG. 54, the liner 540 has a generally elliptical (broadly, "noncircular") entry opening 566 defined by the outer flange portion 562 and tapered central portion 564, and a longitudinal channel 570 defined by the longitudinal portion 568. With reference now to FIG. 56, the longitudinal channel 570 defines a vacuum channel of the cup assembly 518 and is in pneumatic communication with the primary channel 541 of the coupler 520 and thereby the vacuum chamber 565 of the pump 521. The longitudinal channel 570 is also in fluid communication with the container 522. As illustrated in FIG. 56, the liner 540 and the support member 530 cooperatively define a pressure chamber 572 of the cup assembly 518.

As illustrated in FIG. 54, the elliptical opening 566 in the liner 540 has a major axis MAJ and a minor axis MIN. The liner 540 is configured for hinged-like movement generally about the major axis MAJ of the opening 566 between the fully opened configuration, which is illustrated in FIG. 54, and a collapsed configuration, which is illustrated in FIG. 58, in response to pressure applied to the liner (e.g., vacuum pressure in the central passage of the liner and/or positive pressure applied to the interior chamber). This hinged-liked movement more accurately simulates the oral movements applied by a suckling infant to the mother's breast.

In the illustrated embodiment, the outer annular flange 557a of the rigid support frame 557 of the liner 540 has a snap-fit connection with the flanged longitudinally outer end 534 of the support member 530 to thereby releasably secure the liner 540 to the cup assembly 518. As a result, the liner 540 can be removed and individually cleaned. It is understood that the liner 540 can be releasably attached to the cup assembly 518 in other ways.

During operation of the manual breast pump 500, which is illustrated in FIGS. 56-58, the nursing mother grasps the pump and brings the cup assembly 518 into contact with one of her breasts B such that her nipple N is received through the elliptical opening 566 in the liner 540 and into the longitudinal channel 570 of the cup assembly. The planar outer flange portion 562 of the liner 540 contacts the mother's nipple N and portions of her breast B around her nipple. Next, the breast pump 500 is activated by the mother squeezing and releasing the handle 527 to drive the pump 521 through one complete pumping cycle of the pump. The mother will continue squeezing and releasing the handle 527 to drive the pump 521 through as many cycles as desired by the mother. Often, the mother will operate the pump 521 until she stops expressing milk or has collected the desired quantity of milk.

As the mother squeezes the handle 527, the handle moves toward the coupler 520 and pivots about the mount 547 on the lid 525 to lift the stem 553 and thereby the lift assembly upward away from the lid. The stem 553 carries the bellows 555, and diaphragm 583 with it as it moves upward. Upward movement of the diaphragm 583 causes the volume of the vacuum chamber 565 to increase thereby drawing air into the vacuum chamber from the primary chamber 541 of the coupler 520 and the longitudinal channel 570 of the cup assembly 518. Drawing air from the primary chamber 541 and longitudinal channel 570 causes a vacuum to form therein which results in a vacuum being applied to mother's nipple N received in the central passage of the cup assembly 518. In one suitable embodiment, the vacuum applied to the longitudinal channel 570 of the cup assembly 518 and thereby the mother's nipple N is in the range of 70 mm Hg to about 125 mm Hg. It is understood that the vacuum applied to the longitudinal channel 570 of the cup assembly 518 could be greater or less than the valves provided herein.

The volume of the pressure chamber 567 is deceased as the lift assembly is raised during pivotal movement of the handle 527, which causes air to flow out of the pressure chamber and into the pressure chamber 572 of the breast cup via the respective pressure ports 591, 593 collectively formed in the lid 525 and coupler 520. Filling the pressure chamber 572 with air causes it to pressurize. In the illustrated embodiment, pressurization of the pressure chamber 572 results in a compressive force being applied to the mother's nipple N and a portion of the mother' breast B around her nipple N thereby driving milk M within her breast toward her nipple. In one suitable embodiment, the pressure chamber 572 of the cup assembly 518 is pressurized to a pressure between about 70 mm Hg to about 100 mm Hg. The pressure relief valve 543a prevents the pressure within the pressure chamber 567 and thereby the pressure chamber 572 of the cup assembly 518 from exceeding the predetermined pressure. It is understood that the pressure applied to pressure chamber 572 of the cup assembly 518 could be greater or less than the valves provided herein.

As seen in FIGS. 57 and 58, milk M expressed from the mother's breast B flows through the longitudinal channel 570 of the cup assembly 518, through the primary chamber 541 of the coupler 520 and into the container 522 by gravity. A partition 587 is located in the coupler 520 to divert the flow of milk downward toward the container 522 and thereby prevent milk M from flowing toward the pump housing 513. In the illustrated embodiment, a duckbill valve 561 is disposed between the coupler 520 and the container 522 to pneumatically isolate the primary chamber 541 of the couple from the interior of the container. When the handle 527 is squeezed, the vacuum created in the primary chamber 541 of the coupler 520 by the pump 521 causes the duckbill valve 561 to close. When the handle 527 is released, the absence of vacuum in the primary chamber 541 caused the duckbill valve 561 to open and thereby allow the milk M to flow into the container 522.

The pumping cycle is repeated as often as necessary to express as much milk as the mother desires or is able to produce. The total pump cycle time of each pumping cycle is directly dependent on the rate at which the mother squeezes the handle 527. The faster the mother squeezes and releases the handle 527, the faster the pump cycle rate. The breast pump 500 described herein has been designed to more closely mimic the suckling of a nursing infant thereby providing a significantly more efficient and comfortable pump to mothers for expressing breast milk. More particularly, the breast pump 500 operates at a relatively low vacuum pressure as compared to conventional manual breast pumps, has a breast cup with an elliptical opening (generally mouth shaped) for receiving the nipple of the mother's breast and capable of applying a compressive force to the mother's breast around her nipple.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A breast pump comprising:
   at least one collection assembly for engaging at least a portion of a breast surrounding a nipple;
   a vacuum pump for applying a vacuum to the collection assembly and thereby to at least the nipple of the breast;
   a controller that cyclically operates the vacuum pump between a maximum vacuum pressure in the range of about 70 mm Hg to about 150 mm Hg and a minimum latching vacuum pressure of about 30 mm Hg, the latching pressure facilitating retention of the collection assembly on the portion of the breast during use of the breast pump.

2. The breast pump as set forth in claim 1 wherein maximum vacuum pressure is in the range of about 75 mm Hg to about 125 mm Hg.

3. The breast pump as set forth in claim 2 wherein the vacuum pump is operated at the maximum vacuum pressure in the range of about 50 percent to about 80 percent of each cycle.

4. The breast pump as set forth in claim 3 wherein the vacuum pump is operated at the maximum vacuum pressure for about 70 percent of each cycle.

5. The breast pump as set forth in claim 1 wherein the vacuum pump cycles between the maximum vacuum pressure and the minimum latching vacuum pressure between about 50 and about 90 times per minute.

6. The breast pump as set forth in claim 5 wherein the vacuum pump cycles between the maximum vacuum pressure and the minimum latching vacuum pressure between about 60 and about 70 times per minute.

7. The breast pump as set forth in claim 6 wherein the vacuum pump cycles between the maximum vacuum pressure and the minimum latching vacuum pressure about 60 times per minute.

8. The breast pump as set forth in claim 1 wherein the collection assembly comprises a cup assembly, a container for receiving milk expressed from the nipple, and a coupler for fluidly connecting the cup assembly to the container.

9. The breast pump as set forth in claim 1 further comprising a regulator valve for allowing a user to selectively adjust the maximum vacuum pressure between about 70 mm Hg and about 150 mm Hg.

10. The breast pump as set forth in claim 1 wherein the controller is a programmable logic controller.

11. The breast pump as set forth in claim 1 further comprising a valve operatively connected to the controller, the controller being programmed to move the valve between an open position and a closed position, the open position of the valve corresponding to the vacuum pump operating at the minimum latching vacuum pressure and the closed position of the valve corresponding to the vacuum pump operating at the maximum vacuum pressure.

12. A breast pump comprising:
at least one collection assembly including a cup assembly, a container for receiving milk expressed from a nipple of a breast, and a coupler for fluidly connecting the cup assembly to the container, the cup assembly having a support member and an liner mounted on the support member, the liner comprising an outer flange portion and a longitudinal portion extending outward from the flange portion, the outer flange portion of the liner being generally planar and adapted to engage the portion of the breast surrounding the nipple during use of the cup assembly, the longitudinal portion of the liner being generally tubular and adapted to receive the nipple of the breast therein;
a vacuum pump for applying a vacuum to the longitudinal portion of the liner and thereby to the nipple;
a positive pressure pump for pressurizing the outer flange portion of the liner to thereby apply a force against the breast at a location spaced from the nipple.

13. The breast pump as set forth in claim 12 wherein the positive pressure pump is adapted to positively pressurize the longitudinal portion of the liner to compress at least a portion of the longitudinal portion against the nipple.

14. The breast pump as set forth in claim 12 further comprising an inner liner disposed between the liner and support member, the inner liner at least in part defining a first pressure chamber, the first pressure chamber being in communication with the positive pressure pump so that the positive pressure pump can pressurize the first pressure chamber, wherein pressurization of the first pressure chamber by the positive pressure pump causes the longitudinal portion of the outer flange to compress against the breast.

15. The breast pump as set forth in claim 14 wherein the positive pressure pump is operable to pressurize the first pressure chamber to a pressure in the range of about 30 mm Hg to about 100 mm Hg.

16. The breast pump as set forth in claim 15 wherein the positive pressure pump is operable to pressurize the first pressure chamber to a pressure of about 85 mm Hg.

17. The breast pump as set forth in claim 16 wherein the first pressure chamber is cyclically pressurized and depressurized during operation of the breast pump.

18. The breast pump as set forth in claim 12 wherein the liner at least in parts defines a second pressure chamber, the second pressure chamber being adapted for pressurization by the positive pressure pump, wherein pressurization of the second pressure chamber causes outward expansion of the outer flange portion of the liner to thereby apply the force against the breast at a location spaced from the nipple.

19. The breast pump as set forth in claim 18 wherein the positive pressure pump is operable to pressurize the second pressure chamber to a pressure in the range of about 70 mm Hg to about 100 mm Hg.

20. The breast pump as set forth in claim 19 wherein the positive pressure pump is operable to pressurize the second pressure chamber to about 85 mm Hg.

21. The breast pump as set forth in claim 20 wherein the second pressure chamber is cyclically pressurized and depressurized during operation of the breast pump.

22. The breast pump as set forth in claim 12 further includes a controller programmed to operate the breast pump through a pumping cycle, the pumping cycle including a stimulating mode and an expressing mode.

23. The breast pump as set forth in claim 22 wherein the controller is programmed to operate the breast pump at a rate in the range of about 90-120 cycles per minute during the stimulating mode.

24. The breast pump as set forth in claim 12 wherein the breast pump is a manual pump having a moveable handle that is adapted to drive both the positive pressure pump and the vacuum pump.

25. The breast pump as set forth in claim 12 wherein the vacuum pump and the positive pressure pump are defined by a single pump.

26. The breast pump as set forth in claim 12 wherein the vacuum pump and the positive pressure pump are separate, independent pumps.

* * * * *